US008217048B2

(12) United States Patent
Perni et al.

(10) Patent No.: US 8,217,048 B2
(45) Date of Patent: *Jul. 10, 2012

(54) INHIBITORS OF SERINE PROTEASES, PARTICULARLY HCV NS3-NS4A PROTEASE

(75) Inventors: Robert B. Perni, Marlborough, MA (US); John J. Court, Littleton, MA (US); Shawn D. Britt, Andover, MA (US); Janos Pitlik, Westborough, MA (US); John H. van Drie, Andover, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/825,237

(22) Filed: Jun. 28, 2010

(65) Prior Publication Data
US 2011/0104115 A1    May 5, 2011

Related U.S. Application Data

(63) Continuation of application No. 12/082,668, filed on Apr. 10, 2008, now Pat. No. 7,745,444, which is a continuation of application No. 10/936,450, filed on Sep. 7, 2004, now Pat. No. 7,378,422.

(60) Provisional application No. 60/500,670, filed on Sep. 5, 2003.

(51) Int. Cl.
*A61K 31/497* (2006.01)
*C07D 241/24* (2006.01)

(52) U.S. Cl. ............... 514/255.05; 514/255.06; 544/406

(58) Field of Classification Search .......... 514/255.05, 514/255.06, 397, 343; 544/406; 546/278.4; 548/314.7
See application file for complete search history.

(56) References Cited

U.S. PATENT DOCUMENTS

| | | | |
|---|---|---|---|
| 4,499,082 A | 2/1985 | Shenvi | |
| 4,720,484 A | 1/1988 | Vincent et al. | |
| 4,880,780 A | 11/1989 | Trainor et al. | |
| 5,053,519 A | 10/1991 | Teetz et al. | |
| 5,231,084 A | 7/1993 | Hock et al. | |
| 5,371,072 A | 12/1994 | Webb et al. | |
| 5,384,410 A | 1/1995 | Kettner | |
| 5,468,858 A | 11/1995 | Berlin et al. | |
| 5,484,801 A | 1/1996 | Al-Razzak et al. | |
| 5,496,927 A | 3/1996 | Kolb et al. | |
| 5,502,061 A | 3/1996 | Hui | |
| 5,559,158 A | 9/1996 | Al-Razzak et al. | |
| 5,610,193 A | 3/1997 | Al-Razzak et al. | |
| 5,656,600 A | 8/1997 | Abelman et al. | |
| 5,656,627 A | 8/1997 | Bemis et al. | |
| 5,672,582 A | 9/1997 | Veber et al. | |
| 5,716,929 A | 2/1998 | Bermis et al. | |
| 5,725,878 A | 3/1998 | Al-Razzak et al. | |
| 5,736,520 A | 4/1998 | Bey et al. | |
| 5,756,466 A | 5/1998 | Bermis et al. |
| 5,760,029 A | 6/1998 | Jadhay et al. |
| 5,807,876 A | 9/1998 | Armistead et al. |
| 5,847,135 A | 12/1998 | Bermis et al. |
| 5,849,866 A | 12/1998 | Kolb et al. |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bermis et al. |
| 5,990,276 A | 11/1999 | Zhang et al. |
| 6,018,020 A | 1/2000 | Attwood et al. |
| 6,025,147 A | 2/2000 | Bermis et al. |
| 6,025,516 A | 2/2000 | Ramaswamy et al. |
| 6,037,157 A | 3/2000 | Norbeck et al. |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bermis et al. |
| 6,117,639 A | 9/2000 | Germann et al. |
| 6,130,315 A | 10/2000 | Kolb et al. |
| 6,143,715 A | 11/2000 | Llinas-Brunet et al. |
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Macolm |
| 6,225,320 B1 | 5/2001 | Kulagowski et al. |
| 6,251,583 B1 | 6/2001 | Zhang et al. |
| 6,265,380 B1 | 7/2001 | Tung |
| 6,268,207 B1 | 7/2001 | Bailey |

(Continued)

FOREIGN PATENT DOCUMENTS

DE    3211676    10/1983

(Continued)

OTHER PUBLICATIONS

Akahoshi, "Chimase inhibitors and their therapeutic potential," *Drugs of the Future*, 27(8):765-777 (2002).
Alberti et al., "Natural History of Hepatitis C", *J. Hepatology*, 31: 17-24 (1999).
Alter et al., "The Epidemiology of Viral Hepatitis in the United States", *Gastroenterol. Clin. North Am.*, 23:437-455 (1994).
Alter, "Hepatitis C Virus-Infection in the United States", *J. Hepatology*, 31: 88-91 (1999).
Arasappan et al., "Hepatitis C virus-NS3-4A serine protease inhibitors: SAR of P'2 moiety with improved potency," *Bioorganic and Medicinal Chemistry Letters*, 15(19):4180-4194 (2005).

(Continued)

Primary Examiner — Jason M Nolan
(74) Attorney, Agent, or Firm — Ropes & Gray LLP; James F. Haley, Jr.; Yang Xu

(57) ABSTRACT

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention. The invention further relates to processes for preparing these compounds.

38 Claims, No Drawings

U.S. PATENT DOCUMENTS

| | | |
|---|---|---|
| 6,274,613 B1 | 8/2001 | Plant et al. |
| 6,303,287 B1 | 10/2001 | Kim et al. |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet |
| 6,420,522 B1 | 7/2002 | Bermis et al. |
| 6,498,178 B2 | 12/2002 | Stamos et al. |
| 6,528,276 B1 | 3/2003 | Germann et al. |
| 6,534,523 B1 | 3/2003 | Llinas-Brunet et al. |
| 6,541,496 B1 | 4/2003 | Armistead et al. |
| 6,548,555 B1 | 4/2003 | Curatolo et al. |
| 6,602,718 B1 | 8/2003 | Augello et al. |
| 6,608,027 B1 | 8/2003 | Tsantrizos et al. |
| 6,608,067 B1 | 8/2003 | Tung |
| 6,617,309 B2 | 9/2003 | Tung |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,900,238 B1 | 5/2005 | Wong et al. |
| 6,900,434 B2 | 5/2005 | Kuwabara |
| 6,909,000 B2 | 6/2005 | Farmer |
| 6,911,428 B2 | 6/2005 | Zhu et al. |
| 6,914,122 B2 | 7/2005 | Venkatraman |
| 6,919,423 B2 | 7/2005 | Llinas-Brunet |
| 6,939,692 B2 | 9/2005 | Bathe et al. |
| 6,939,854 B2 | 9/2005 | Priestley |
| 7,012,066 B2 | 3/2006 | Saksena et al. |
| 7,034,178 B2 | 4/2006 | Faber et al. |
| 7,091,184 B2 | 8/2006 | Llinas-Brunet et al. |
| 7,105,302 B2 | 9/2006 | Bathe et al. |
| 7,109,172 B2 | 9/2006 | Britt |
| 7,119,073 B2 | 10/2006 | Colarusso et al. |
| 7,122,627 B2 | 10/2006 | Priestley |
| 7,169,760 B2 | 1/2007 | Saksena et al. |
| 7,208,600 B2 | 4/2007 | Cottrell |
| 7,241,796 B2 | 7/2007 | Farmer |
| 7,244,721 B2 | 7/2007 | Saksena et al. |
| 7,250,520 B2 | 7/2007 | Wallace |
| 7,273,885 B2 | 9/2007 | Pitlik |
| 7,288,624 B2 | 10/2007 | Bemis et al. |
| 7,365,092 B2 | 4/2008 | Cottrell |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung |
| 7,494,988 B2 | 2/2009 | Perni |
| 7,504,378 B2 | 3/2009 | Llinas-Brunet et al. |
| 7,592,316 B2 | 9/2009 | Njoroge et al. |
| 7,683,033 B2 | 3/2010 | Cottrell et al. |
| 7,745,444 B2 | 6/2010 | Perni et al. |
| 7,820,671 B2 | 10/2010 | Babine et al. |
| 7,863,274 B2 | 1/2011 | Tung |
| 7,906,550 B2 | 3/2011 | Cottrell et al. |
| 7,964,624 B1 | 6/2011 | Cottrell et al. |
| 7,985,762 B2 | 7/2011 | Cottrell et al. |
| 8,039,623 B2 | 10/2011 | Cottrell et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby et al. |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris |
| 2004/0067901 A1 | 4/2004 | Bhat et al. |
| 2004/0072788 A1 | 4/2004 | Bhat et al. |
| 2004/0077600 A1 | 4/2004 | Tung |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet et al. |
| 2004/0266731 A1 | 12/2004 | Tung et al. |
| 2005/0020503 A1 | 1/2005 | Llinas-Brunet et al. |
| 2005/0049220 A1 | 3/2005 | Stuyver |
| 2005/0059606 A1 | 3/2005 | Saksena et al. |
| 2005/0062522 A1 | 3/2005 | Haider et al. |
| 2005/0080005 A1 | 4/2005 | Llinas-Brunet et al. |
| 2005/0080017 A1 | 4/2005 | Cottrell et al. |
| 2005/0090450 A1 | 4/2005 | Farmer et al. |
| 2005/0107304 A1 | 5/2005 | Britt et al. |
| 2005/0112093 A1 | 5/2005 | Ette et al. |
| 2005/0119189 A1 | 6/2005 | Cottrell |
| 2005/0119318 A1 | 6/2005 | Hudyma et al. |
| 2005/0120398 A1 | 6/2005 | Kalkeri et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine |
| 2005/0197301 A1 | 9/2005 | Njoroge et al. |
| 2005/0215486 A1 | 9/2005 | Cottrell |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui |
| 2006/0105978 A1 | 5/2006 | Chu |
| 2006/0205672 A1 | 9/2006 | Saksena et al. |
| 2006/0211629 A1 | 9/2006 | Britt |
| 2007/0087973 A1 | 4/2007 | Tanoury |

| | | | | | | |
|---|---|---|---|---|---|---|
| 2007/0105781 A1 | 5/2007 | Lyons | | WO | WO 01/07407 | 2/2001 |
| 2007/0161789 A1 | 7/2007 | Cottrell | | WO | WO 01/16300 | 3/2001 |
| 2007/0179167 A1 | 8/2007 | Cottrell | | WO | WO 01/32691 | 5/2001 |
| 2007/0191381 A1 | 8/2007 | Tung | | WO | WO 01/40262 | 6/2001 |
| 2007/0212683 A1 | 9/2007 | Connelly | | WO | WO 01/40266 | 6/2001 |
| 2007/0218012 A1 | 9/2007 | Bittorf et al. | | WO | WO 01/58929 | 8/2001 |
| 2007/0218138 A1 | 9/2007 | Bittorf | | WO | WO 01/64678 | 9/2001 |
| 2007/0225297 A1 | 9/2007 | Perni et al. | | WO | WO 01/74768 | 10/2001 |
| 2007/0231262 A1 | 10/2007 | Lin | | WO | WO 01/77113 | 10/2001 |
| 2007/0243166 A1 | 10/2007 | Llinas-Brunet et al. | | WO | WO 01/81325 | 11/2001 |
| 2007/0244334 A1 | 10/2007 | Tanoury et al. | | WO | WO 02/07761 | 1/2002 |
| 2007/0292933 A1 | 12/2007 | Pitlik | | WO | WO 02/08187 | 1/2002 |
| 2008/0045480 A1 | 2/2008 | Farmer | | WO | WO 02/08198 | 1/2002 |
| 2008/0070972 A1 | 3/2008 | Kadiyala et al. | | WO | WO 02/08244 | 1/2002 |
| 2008/0082155 A1 | 4/2008 | Fischell | | WO | WO 02/08251 | 1/2002 |
| 2008/0106058 A1 | 5/2008 | Demick | | WO | WO 02/08256 | 1/2002 |
| 2008/0125376 A1 | 5/2008 | Cottrell | | WO | WO 02/09588 | 2/2002 |
| 2008/0167480 A1 | 7/2008 | Wallace | | WO | WO 02/18369 | 3/2002 |
| 2008/0267915 A1 | 10/2008 | Lin | | WO | WO 02/22828 | 3/2002 |
| 2008/0311079 A1 | 12/2008 | Perni et al. | | WO | WO 02/48116 | 6/2002 |
| 2009/0022688 A1 | 1/2009 | Farmer | | WO | WO 02/48157 | 6/2002 |
| 2009/0098802 A1 | 4/2009 | Talamo | | WO | WO 02/48172 | 6/2002 |
| 2009/0143312 A1 | 6/2009 | Tung | | WO | WO 02/060926 | 8/2002 |
| 2009/0191555 A1 | 7/2009 | Lin et al. | | WO | WO 02/079234 | 10/2002 |
| 2009/0247468 A1 | 10/2009 | Bittorf et al. | | WO | WO 03/003804 | 1/2003 |
| 2009/0291902 A1 | 11/2009 | Cottrell et al. | | WO | WO 03/006490 | 1/2003 |
| 2010/0137583 A1 | 6/2010 | Babine et al. | | WO | WO 03/020298 | 3/2003 |
| 2010/0173851 A1 | 7/2010 | Pitlik et al. | | WO | WO 03/035060 | 5/2003 |
| 2010/0272681 A1 | 10/2010 | Farmer et al. | | WO | WO 03/053349 | 7/2003 |
| 2010/0330109 A1 | 12/2010 | Cottrell et al. | | WO | WO 03/062228 | 7/2003 |
| 2011/0112114 A1 | 5/2011 | Tung et al. | | WO | WO 03/062265 | 7/2003 |
| 2011/0165120 A1 | 7/2011 | Cottrell et al. | | WO | WO 03/064416 | 8/2003 |
| 2011/0182856 A1 | 7/2011 | Cottrell et al. | | WO | WO 03/064455 | 8/2003 |
| | | | | WO | WO 03/064456 | 8/2003 |
| FOREIGN PATENT DOCUMENTS | | | | WO | WO 03/087092 | 10/2003 |
| DE | 19648793 | 5/1998 | | WO | WO 03/091202 | 11/2003 |
| EP | 0 195 212 | 9/1986 | | WO | WO 03/099274 | 12/2003 |
| EP | 0 275 101 A2 | 7/1988 | | WO | WO 03/099316 | 12/2003 |
| EP | 0 356 595 A1 | 3/1990 | | WO | WO 2004/026896 | 4/2004 |
| EP | 0 363 284 | 4/1990 | | WO | WO 2004/030670 | 4/2004 |
| EP | 0 368 719 A2 | 5/1990 | | WO | WO 2004/032827 | 4/2004 |
| EP | 0 417 721 | 9/1990 | | WO | WO 2004/037855 | 5/2004 |
| EP | 0 675 112 | 3/1995 | | WO | WO 2004/039833 | 5/2004 |
| EP | 1008592 | 6/2000 | | WO | WO 2004/072243 | 8/2004 |
| EP | 1498 411 | 1/2005 | | WO | WO 2004/089974 | 10/2004 |
| JP | 09124691 | 5/1997 | | WO | WO 2004/092161 | 10/2004 |
| JP | 2001-502694 T | 2/2001 | | WO | WO 2004/092162 | 10/2004 |
| JP | 2005-535574 T | 11/2005 | | WO | WO 2004/093798 | 11/2004 |
| WO | WO 92/12140 | 7/1992 | | WO | WO 2004/094452 | 11/2004 |
| WO | WO 93/25574 | 12/1993 | | WO | WO 2004/103996 | 12/2004 |
| WO | WO 94/14436 | 7/1994 | | WO | WO 2004/113365 | 12/2004 |
| WO | WO 95/07696 | 3/1995 | | WO | WO 2005/007681 | 1/2005 |
| WO | WO 95/09614 | 4/1995 | | WO | WO 2005/010029 | 2/2005 |
| WO | WO 95/35308 | 12/1995 | | WO | WO 2005/021584 | 3/2005 |
| WO | WO 96/11697 | 4/1996 | | WO | WO 2005/028501 | 3/2005 |
| WO | WO 96/33209 | 10/1996 | | WO | WO 2005/028502 | 3/2005 |
| WO | WO 97/17364 | 5/1997 | | WO | WO 2005/030796 | 4/2005 |
| WO | WO 97/40028 | 10/1997 | | WO | WO 2005/035525 | 4/2005 |
| WO | WO 97/43310 | 11/1997 | | WO | WO 2005/037214 | 4/2005 |
| WO | WO 98/13365 | 4/1998 | | WO | WO 2005/037860 | 4/2005 |
| WO | WO 98/17679 | 4/1998 | | WO | WO 2005/042570 | 5/2005 |
| WO | WO 98/22496 | 5/1998 | | WO | WO 2005/046712 | 5/2005 |
| WO | WO 98/40381 | 9/1998 | | WO | WO 2005/051410 | 6/2005 |
| WO | WO 98/46630 | 10/1998 | | WO | WO 2005/051980 | 6/2005 |
| WO | WO 99/07733 | 2/1999 | | WO | WO 2005/054430 | 6/2005 |
| WO | WO 99/07734 | 2/1999 | | WO | WO 2005/058821 | 6/2005 |
| WO | WO 99/17775 | 4/1999 | | WO | WO 2005/070955 | 8/2005 |
| WO | WO 99/37666 | 7/1999 | | WO | WO 2005/073195 | 8/2005 |
| WO | WO 99/38888 | 8/1999 | | WO | WO 2005/073216 | 8/2005 |
| WO | WO 99/50230 | 10/1999 | | WO | WO 2005/077969 | 8/2005 |
| WO | WO 99/64442 | 12/1999 | | WO | WO 2005/085242 | 9/2005 |
| WO | WO 00/09543 | 2/2000 | | WO | WO 2005/085275 | 9/2005 |
| WO | WO 00/09558 | 2/2000 | | WO | WO 2005/087721 | 9/2005 |
| WO | WO 00/16767 | 3/2000 | | WO | WO 2005/087725 | 9/2005 |
| WO | WO 00/23421 | 4/2000 | | WO | WO 2005/087731 | 9/2005 |
| WO | WO 00/31129 | 6/2000 | | WO | WO 2005/095403 | 10/2005 |
| WO | WO 00/56331 | 9/2000 | | WO | WO 2005/107745 | 11/2005 |
| WO | WO 00/59929 | 10/2000 | | WO | WO 2005/113581 | 12/2005 |
| WO | WO 01/02424 | 1/2001 | | WO | WO 2005/123076 | 12/2005 |

| WO | WO 2006/000085 | 1/2006 |
| --- | --- | --- |
| WO | WO 2006/002539 | 1/2006 |
| WO | WO 2006/007448 | 1/2006 |
| WO | WO 2006/007700 | 1/2006 |
| WO | WO 2006/007708 | 1/2006 |
| WO | WO 2006/050250 | 5/2006 |
| WO | WO 2007/016589 | 2/2007 |
| WO | WO 2007/022459 | 2/2007 |
| WO | WO 2007/025307 | 3/2007 |
| WO | WO 2007/098270 | 8/2007 |
| WO | WO 2007/109023 | 9/2007 |
| WO | WO 2007/109605 | 9/2007 |
| WO | WO 2008/106058 | 9/2008 |
| WO | WO 2008/106139 | 9/2008 |

OTHER PUBLICATIONS

Bartenschlager et al., "Nonstructural Protein 3 of the Hepatitis C Virus-Encodes a Serine-Type Proteinase Required for Cleavage at the NS3/4 and NS4/5 Junctions", *J. Virol.*, 67: 3835-3844 (1993).

Bastos et al., "Inhibitors of human heart chymase based on a peptide library," *PNAS*, 92(15):6738-6742 (1995).

Beaulieu and Llinàs-Brunet, "Therapies for Hepatitis C Infection: Targeting the Non-Structural Proteins", *Current Medicinal Chemistry-Anti-Infective Agents*, 1: 163-176 (2002).

Burkhart et al., "Preparation of alpha-keto ester enol acetates as potential prodrugs of human neutrophil elastase inhibitors," *Bioorganic and Medicinal Chemistry Letters*, 8(1):63-64 (1998).

Chambers et al., "Evidence that the N-terminal Domain of Nonstructural Protein NS3 From Yellow Fever Virus-Is a Serine Protease Responsible for Site-Specific Cleavages in the Viral Polyprotein", *Proc. Natl. Acad. Sci. USA*, 87: 8898-8902 (1990).

Choo et al., "Genetic Organization and Diversity of the Hepatitis C Virus", *Proc. Natl. Acad. Sci. USA*, 88: 2451-2455 (1991).

Clayette et al., "IFN-τ, A New Type I IFN with Antiretroviral Activity", *Pathol. Biol.* (Paris), 47: 553-559 (1999).

Davis et al., "Future Options for the Management of Hepatitis C.", *Seminars in Liver Disease*, 19: 103-112 (1999).

Di Bisceglie and Hoofnagle, "Optimal Therapy of Hepatitis C", *Hepatology*, 36: S121-S127 (2002).

Dunsdon et al., "Solid Phase Synthesis of Aminoboronic Acids: Potent Inhibitors of the Hepatitis C Virus-NS3 Proteinase", *Bioorg. Med. Chem. Lett.*, 10: 1577-1579 (2000).

Dymock, "Emerging Therapies for Hepatitis C Virus-Infections", *Emerging Drugs*, 6: 13-42 (2001).

Gettins, et al., "Serpin Structure, Mechanism, and Function," *Chem. Rev.*, 102:4751-4803 (2002).

Grakoui et al., "Characterization of the Hepatitis C Virus-Encoded Serine Proteinase: Determination of Proteinase-Dependent Polyprotein Cleavage Sites", *J. Virol.*, 67: 2832-2843 (1993).

Grakoui et al., "Expression and Identification of Hepatitis C Virus-Polyprotein Cleavage Products", *J. Virol.*, 67: 1385-1395 (1993).

Han et al., "α-Ketoamides, α-Ketoesters and α-Diketones as HCV NS3 Protease Inhibitors", *Bioorg. Med. Chem. Lett.*, 10: 711-713 (2000).

Heathcote et al. "Peginterferon Alpha-2a in Patients with Chronic Hepatitis C and Cirrhosis", *New England Journal of Medicine*, 343: 1673-1680 (2000).

Iwarson, "The Natural Course of Chronic Hepatitis", *FEMS Microbiology Reviews*, 14: 201-204 (1994).

Janssen et al., "Suicide Associated with Alfa-Interferon Therapy for Chronic Viral Hepatitis", *J. Hepatol.*, 21: 241-243 (1994).

Johansson et al., "Acyl sulfonamides as potent protease inhibitors of the hepatitis C virus-full-Length NS3 (protease-helicase/NTPase): a comparative study of different C-terminals," *Bioorganic and Medicinal Chemistry*, 11:2551-2568 (2003).

Kao et al., "Efficacy of Consensus-Interferon in the Treatement of Chronic Hepatitis", *J. Gastroenterol. Hepatol.* 15: 1418-1423 (2000).

Kato et al., "Molecular Cloning of the Human Hepatitis C Virus-Genome From Japanese Patients with Non-A, Non-B Hepatitis C", *Proc. Natl. Acad. Sci. USA*, 87: 9524-9528 (1990).

Kew, "Hepatitis C and Hepatocellular Carcinoma", *FEMS Microbiology Reviews*, 14: 211-219 (1994).

LaPlante et al., "NMR Line-Broadening and Transferred NOESY as a Medicinal Chemistry Tool for Studying Inhibitors of the Hepatitis C Virus-NS3 Protease Domain", *Bioorg. Med. Chem. Lett.*, 10: 2271-2274 (2000).

Lavanchy, "Global Surveillance and Control of Hepatitis C", *J. Viral Hepatitis*, 6: 35-47 (1999).

Lehmann et al., "Über die chemischen und biologischen Eigenschaften einiger α-Aminoketone" *Helvetica Chimica Acta*, 33:1217-1226 (1950).

Lin et al., "Hepatitis C Virus-NS3 Serine Proteinase: *Trans*-Cleavage Requirements and Processing Kinetics", *J. Virol.*, 68: 8147-8157 (1994).

Lipinski, "Bioisosteres in Drug Design", *Annual Reports in Medicinal Chemistry*, 21: 286-288 (1986).

Llinàs-Brunet et al., Studies on the C-terminal of hexapeptide inhibitors of the hepatitis C virus-serine protease, *Bioorganic and Medicinal Chemistry Letters*, 8(19):2719-2724 (1998).

Llinàs-Brunet et al., "Highly Potent and Selective Peptide-Based Inhibitors of the Hepatitis C Virus-Serine Protease: Towards Smaller Inhibitors", *Bioorg. Med. Chem. Lett.*, 10: 2267-2270 (2000).

Llinàs-Brunet et al., "Peptide-Based Inhibitors of the Hepatitis C Virus-Serine Protease", *Bioorg. Med. Chem. Lett.*, 8: 1713-1718 (1998).

Markland et al., "Broad-Spectrum Antiviral Activity of the IMP Dehydrogenase Inhibitor VX-497: A Comparison with Ribavirin and Demonstration of Antiviral Additivity with Alpha Interferon", *Antimicrobial & Antiviral Chemotherapy*, 44: 859-866 (2000).

Mehdi et al., "The Inhibition of Human Neutrophil Elastase and Cathepsin C by Peptidyl 1,2-Dicarbonyl Derivatives", *Biochemical and Biophysical Research Communications*, 166(2):595-600 (1990).

Moradpour et al., "Current and Evolving Therapies for Hepatitis C", *Eur. J. Gastroenterol. Hepatol.*, 11: 1199-1202 (1999).

Patani et al., "Bioisosterism: A Rational Approach in Drug Design," *Chemical Reviews*, 96(8):3147-3176 (1996).

Perni et al., "Inhibitors of hepatitis C virus-NS3.4A protease 1. Non-charged tetrapeptide variants," *Bioorganic and Medicinal Chemistry Letters*, 13(22):4059-4063 (2003).

Perni et al., "Inhibitors of hepatitis C virus-NS3.4A protease 2. Warhead SAR and optimization," *Bioorganic and Medicinal Chemistry Letters*, 14(6):1441-1446 (2004).

Perni et al., "Inhibitors of hepatitis C virus-NS3.4A protease. Part 3: P2 proline variants," *Bioorganic and Medicinal Chemistry Letters*, 14(8):1939-1942 (2004).

Poliakov et al., "Structure-activity relationship for the selectivity of hepatitis C virus—NS3 protease inhibitors," *BBA—General Subject*, Elsevier Science Publishers, NL., 1672:51-59 (2004).

Reddy et al. "Efficacy and Safety of Pegylated (40-kd) Interferon α-2a Compared with Interferon α-2a in Noncirrhotic Patients with Chronic Hepatitis C", *Hepatology*, 33: 433-438 (2001).

Renault and Hoofnagle, "Side Effects of Alpha Interferon", *Seminars in Liver Disease*, 9: 273-277 (1989).

Saito et al., "Hepatitis C Virus-Infection Is Associated with the Development of Hepatocellular Carcinoma", *Proc. Natl. Acad. Sci. USA*, 87: 6547-6549 (1990).

Sasaki et al., "A Novel Stereodivergent Synthesis of Optically Pure cis- and trans-3-Substituted Proline Derivatives," *Journal of Organic Chemistry*, 62(3):765-770 (1997).

Sauder "Immunomodulatory and Pharmacologic Properties of Imiquimod", *J. Am. Acad. Dermatol.*, 43: S6-11 (2000).

Schöllkopf et al., "2-Oxazolines from α-Metalated Isocyanides and Carbonyl-Compounds. A New Synthesis for β-Amino Alcohols", *Liebigs Ann. Chem.*: 183-202 (1976).

Semple et al., "New Synthetic Technology for Efficient Construction of α-Hydroxy-β-Amino Amides via the Passerini Reaction", *Org. Letts.*, 2: 2769-2772 (2000).

Takamizawa et al., "Structure and Organization of the Hepatitis C Virus-Genome Isolated From Human Carriers," *J. Virol.*, 65: 1105-1113 (1991).

Tazulakhova et al., "Russian Experience in Screening, Analysis, and Clinical Application of Novel Interferon Inducers", *J. Interferon Cytokine Res.*, 21: 65-73 (2001).

Thornber, "Isosterism and Molecular Modification in Drug Design", *Chemical Society Reviews*, 8: 563-580 (1979).

Tomei et al., "NS3 Is a Serine Protease Required for Processing of Hepatitis C Virus-Polyprotein", *J. Virol.*, 67: 4017-4026 (1993).

Walker et al., "Hepatitis C Virus: An Overview of Current Approaches and Progress", *DDT*, 4: 518-529 (1999).

Weiland, "Interferon Therapy in Chronic Hepatitis C Virus-Infection", *FEMS Microbiol. Rev.*, 14: 279-288 (1994).

Yun et al., "Oxidation of the Antihistaminic Drug Terfenadine in Human Liver Microsomes", *Drug Metabolism & Disposition*, 21: 403-407 (1993).

USPTO Office Action dated Apr. 3, 2009 in U.S. Appl. No. 11/434,008.

USPTO Office Action dated Apr. 4, 2008 in U.S. Appl. No. 11/051,977.

USPTO Office Action dated Dec. 21, 2006 in U.S. Appl. No. 11/051,977.

USPTO Office Action dated Dec. 23, 2008 in U.S. Appl. No. 10/344,112.

USPTO Office Action dated Dec. 3, 2008 in U.S. Appl. No. 11/880,629.

USPTO Office Action dated Dec. 8, 2008 in U.S. Appl. No. 11/716,248.

USPTO Office Action dated Feb. 23, 2009 in U.S. Appl. No. 10/614,432.

USPTO Office Action dated Feb. 28, 2008 in U.S. Appl. No. 11/434,008.

USPTO Office Action dated Jan. 11, 2007 in U.S. Appl. No. 10/943,265.

USPTO Office Action dated Jan. 18, 2006 in U.S. Appl. No. 10/821,793.

USPTO Office Action dated Jan. 21, 2009 in U.S. Appl. No. 11/051,977.

USPTO Office Action dated Jan. 8, 2008 in U.S. Appl. No. 10/821,793.

USPTO Office Action dated Jun. 7, 2007 in U.S. Appl. No. 11/434,008.

USPTO Office Action dated Mar. 6, 2008 in U.S. Appl. No. 10/344,112.

USPTO Office Action dated May 12, 2009 in U.S. Appl. No. 11/511,109.

USPTO Office Action dated May 2, 2006 in U.S. Appl. No. 10/943,265.

USPTO Office Action dated May 5, 2008 in U.S. Appl. No. 10/943,265.

USPTO Office Action dated Nov. 15, 2005 in U.S. Appl. No. 10/943,265.

USPTO Office Action dated Oct. 3, 2006 in U.S. Appl. No. 10/821,793.

USPTO Office Action dated Sep. 12, 2007 in U.S. Appl. No. 10/943,265.

USPTO Office Action dated Sep. 6, 2007 in U.S. Appl. No. 11/051,977.

Anonymous, VPI internet press release Sep. 7, 2004.

Anonymous, newsrx internet article, May 31, 2004.

Avolio, "Inhibitors of hepatitis C virum NS3/4A: a-Ketoamide based macrocyclic inhibitors", Bioorganic & Medicinal Chemistry Letters (2009), 19, pp. 2295-2298.

Beak, "Complex Induced Proximity Effects: Enantioselective Syntheses Based on Asymmetric Deprotonations of N-Boc-Pyrrolidines", J. Amer. Chem. Soc., vol. 116(1994), pp. 3231-3239.

Behrens, "Selective Transformations of 2, 3-Epoxy Alcohols and Related Derivatives. Strategies for Nucleophilic Attack at Carbon-3 or Carbon-2", J. Org. Chem., vol. 50 (1985), pp. 5696-5704.

Bergmeier "Synthesis of Bicyclic Proline Analogs Using a formal [3-2] Intramolecular Aziridine-Allylsilane Cycloaddition Reaction", Tetrahedron, vol. 55, No. 26 (1999), pp. 8025-8038.

Blair, "5th Antiviral Drug Discovery and Development Summit", Expert opinion on investigational drugs (2004), 13(8), pp. 1065-1069.

Blankley, "Synthesis and Structure-Activity Relationships of Potent New Abgiotensin Converting Enzyme Inhibitors Containing Saturated Bicyclic Amino Acids", J. of Medicinal Chem., vol. 30 (1987), pp. 992-998.

Cacciola, "The Synthesis of Lysine a-Ketoamide Thrombin Inhibitors via an Epoxy Amide Ring Opening", Tetrahedron Let., vol. 38, No. 33 (1997), pp. 5741-5744.

Chawla, et al., "Challenges in Polymorphism of Pharmaceuticals", CRIPS vol. 5 No. 1, Jan.-Mar. 2004, 4 pages.

Chen, "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.

Chen, "Discovery of Small-Molecule Inhibitors of HCV NS3-4A Protease as Potential Therapeutic Agents against HCV Infection", Current Medicinal Chemistry (2005), 12(20), pp. 2317-2342.

Chen, "P1 and P1' Optimization of [3,4]-Bicycloproline P2 Incorporated Tetrapeptidyl a-ketoamide Based HCV Protease Inhibitors", Letters in Drug Design and Discovery (2005), 2(2), pp. 118-123.

Cheng et al, "Stereoselective Synthesis of unnatural Spiroisoxazolinoproline-Based Amino Acids and Derivatives," Journal of Organic Chemistry, pp. 5673-5677 (2002).

Collado, "Stereocontrolled Synthesis of 4-Substituted (±)-Kainic Acids", Journal of Organic Chem., vol. 63 (1998), pp. 1995-2001.

Dixon, "A Sprioisoazolinoproline-based Amino Acid Scaffold for Solid Phase and One-Bead-One-Compound Library Synthesis", Journal of Combinatorial Chemistry, 9(2007), pp. 143-157.

Donkor et al., "Design, Synthesis, Molecular Modeling Studies, and Calpain Inhibitory Activity of Novel a-Ketoamides Incorporating Polar Residues at the PY-Position", J. Med. Chem. 2004, 47, 72-79.

Elemes, "Synthesis of enantiopure a-deuteriated Boc-L-amino acids", J. Chem. Soc., Perkin Trans., vol. 1 (1995), pp. 537-540.

Elofsson et al., "Towards subunit-specific proteasome inhibitors: synthesis and evaluation of peptide α', '-epoxyketones," Chemistry & Biology, vol. 6, pp. 811-822 (1999).

Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters in Drug Design and Discovery (2005), 2, pp. 497-502.

Field, L. et al., "Organic disulfides and Related Substances. 42. Synthesis and Properties of Some Tertiary Disulfides, Especially Involving Penicillamine," J. Org. Chem., pp. 2624-2629 (1979).

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Complex-Induced Proximity Effects: Evidence for a Prelifhiation Complex and a Rate-Determining Deprotonation in the Asymmetric Lithiation of Boc-Pyrrolidine by an -PrLi/(−) Sparteine Complex", J. Org. Chem., vol. 60 (1995), pp. 7092-7093.

Gallagher, D., "Chiral Organolifhium Complexes: The Effect of Ligand Structure on the Enantioselective Deprotonation of Boc-Pyrrolidine", J. Org. Chem., vol. 60 (1995), pp. 8148-8154.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1H-Imidazol-1-yl)benzoyl]-7-isopropyl-3,7-diazabicyclo[3.3.1]nonane Dihydroperchlorate", J. Med. Chem, vol. 39, No. 13 (1996), pp. 2559-2570.

Golina, S., "Vulcanisation of Poly(diefhyl-n-butylamino) Phosphazenes", Internat'l Polymer Science & Tech., vol. 18, No. 3 (1991), pp. T20-T22.

Hanada, M. et al, "Epoxomicin, a new anti-tumour agent of microbial origin," The Journal of Antibiotics, vol. 45(11), pp. 1746-1752 (1992).

Holladay, M.W. et al., "Dual Antagonists of Platelet Activiating Factor and Histamine. Identification of Structural Requirements for Dual Activity of N-Acyl-4-(5,6-dihydro-11 H-benzo[5,6]cyclohepta-[1,2-b]pyridin-11-ylidene)piperidines," J. Med. Chem., 34, pp. 457-461 (1991).

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using anYttrium-Biphenyldiol Complex", J. Am. Chem. Soc, vol. 127 (2005), pp. 8962-8963.

Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(1), pp. 281A.

Kamandi, E., "Die Synfhese von β-Phenyl-Isoserinen Durch Ammonolyse von β-Phenyl-Glycidestern, I.", Archiv de Pharmazie, vol. 307 No. 11 (1974), pp. 871-878.

Kanamasa, S. et al., "Highly Diastereoselective Michael Addition of Lithiated Camphor Imines of GLycine Esters to .alpha.,.beta.-Unsaturated Esters. Synthesis of Optically Pure 5-Oxo-2,4-pyrrolidinedicarboxylates of Unnatural Stereochemistry," J. Org. Chem, 56, pp. 2875-2883 (1991).

Kempf, D.J. et al., "Symmetry-Based Inhibitors of HIV Protease. Structure-Activity studirs of Acylated 2,4-Diamino-1,5-diphenyl-3-hydroxypentane and 2,5-Diamino-1,6-diphenylhexane-3,4-diol," J. Med. Chem., pp. 320-330 (1993).

Kerrick, S., "Asymmetric Deprotonations: Enantioselective Syntheses of 2-Substituted (tert-Butoxycarbonyl) pyrrolidines", J. Amer. Chem. Soc, vol. 113 (1991), pp. 9703-9710.

Kieffer, Genetic Heterogeneity in the HCV Ns3 Protease of Untreated Genotype 1 Patients Has Little Effect on the Sensitivity of the VX-950, 12th Internat'l Conf. on Hep. C Virus and Related Viruses, Montreal, Canada, Oct. 2-6, 2005.

Kieffer, T., "Genetic Heterogeneity in the HCV NS3 Protease of Untreated Genotype 1 Patients has Little Effect on the Sensitivity to VX-950", Hepatol, vol. 42 (2005), p. 537A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kieffer, T., "Combination of Telaprevir (VX-950) and Peg-Ifn-Alfa Suppresses both Wild-Type Virus and Resistance Variants in HCV Genotype 1-Infected Patients in a 14-Day Phase IB Study", Hepatol. 44, Supp.2 (2006), p. 222A.

Kim et al., "Development and Characterization of Proteasome Inhibitors," Methods Enzymol., vol. 399, pp. 585-609 (2005).

Kim, et al., "Broad-spectrum antiviral activity of the IMP dehydrogenase inhibitor VX-497: a comparison with ribavirin and demonstration of antiviral additivity with alpha interferon", Antimicrob Agents Chemother., Apr. 2000; 44(4):859-66.

Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.

Kim, J., "Crystal structure of the hepatitis C virus NS3 protease domain complexed with a synthetic NS4A cofactor peptide," Cell, vol. 87, 1996, pp. 343-355 [and Kim, J. "Erratum," Cell, vol. 89, No. 1 (1997), p. 159.

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Kwong, A.D., "Structure and Function of Hepatitis C Virus NS3 Helicase", Top Microbiol. Immunol., vol. 242, (2000), pp. 171-196.

Kwong, A.D., "Erratum to 'Hepatitis C Virus NS3/4A Protease' [Antiviral Res. 41 (1998) 1-18]", Antiviral Res., vol. 41 (1999), pp. 1-18.

Kwong, A.D., "Hepatitis C Virus NS3/4A Protease", Antiviral Res., vol. 41 (1999), pp. 67-84.

Kwong, A.D., "An Orally Bioavailable Inhibitor of the HCV NS3-4a Protease; a Potential HCV Therapeutic", 5th Antivir. Drug Disc. and Devel. Summit, (2004).

Kwong, HCV Protease Inhibitors: Activity and Resistance, 13th Conference on Retroviruses and Opp. Infections (CROI), Denver, Co, Feb. 5-8, 2006.

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "A Novel Hepatitis C Protease Inhibitor", HepDART (2005).

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kintetic Analysis and Inhibitor Mapping", Biochemistry, 36 (1997) pp. 9340-9348.

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Intenat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus NS3-NS4A Protease Inhibitor and Alph Interferon Synergistically Inhibits Viral RNA Replication and Facilitates Viral RNA Clearance in Replicon Cells", Antimicrob. Agents Chemo, vol. 48 (2004), pp. 4784-4792.

Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.

Lin, K., "Vx-950: A Tight-Binding HCV Protease Inhibitor with a Superior Sustained Inhibitory Response in HCV Replicon Cells", Hepatol, vol. 38 (2003), p. 222.

Lin, C., "Discovery and Development of VX-950, a Novel, Covalent and Reversible Inhibitor of Hepatitis C Virus NS3-4A Serine Protease", Infect. disord. Drug Targets, vol. 6, No. 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Lipinski, "Bioisosteres in Drug Design", Annual Reports in Medicinal Chemistry, 21: 283-291 (1986).

Lohmann, F., "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc, vol. 127, No. 19 (2005), pp. 6964-6965.

McIntosh et al., caplus an 1988:187008.

McLaren, R., "Infrared observations of circumstellar ammonia in OH/IR supergiants," Astrophysical Journal (1980), 240 (3, Pt. 2), pp. L159-L163.

Meng et al., "Epoxomicin, a potent and selective proteasome inhibitor, exhibits in vivo antiinflammatory activity," Proc. Natl. Acad. Sci., vol. 96, pp. 10403-10408 (1999).

Monn, J., "A Concise, StereocontrolledThiazoliumYlide Approach to Kainic Acid", J. Organic Chem., vol. 59, No. 10 (1994), pp. 2773-2778.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "VX-950: The Discovery of an Inhibitor of the Hepatitis C NS3-4A Protease and a Potential Hepatitis C Virus Therapeutic", Hepatology, vol. 38 (2003) p. 624A.

Perni, "Inhibitors of hepatitis C virus NS3-4A protease: Effect of P4 capping groups on inhibitory potency and pharmacokinetices," Bioorganic & Medicinal Chemistry Letters (2007), 17, pp. 3406-3411.

Perni, R., "The Design of Inhibitors of the HCV NS3-4A Protease: The Identification of a Clinical Development Candidate, VX-950," ACS National Medicinal Chemistry Symposium, Madison, WI, Jun. 2004.

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Perni, R., "Toward Smaller HCV NS3-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Pippel, D., "Complex-Induced Proximity Effects: Steroselective Carbon-Carbon Bond Formation in Chiral Auxiliary Mediated p-Lithiation-Substitution Sequences of β-Substituted Secondary Carboxamides", J. Org. Chem., vol. 63 (1998), pp. 2-3.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.

Reesink, H., "Rapid Decline of Viral RNA in Hepatitis C Patients Treated with VX-950: A Phase 1b, Placebo-Controlled Randomized Study", Gastroenterol., vol. 131, No. 4 (2006), pp. 997-1002.

Reesink, H., "Final Results of a Phase IB, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I., "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-4039.

Schneider, "Changed Phosphodiesterase Selectivity and Enhanced in vitro Efficacy by Selective Deuteration of Sildenafil", Arzneimittel-Forschung (Drug Res.), vol. 57, No. 6 (2007), pp. 293-298, Editio Cantor Vertag, Aulendorf (Germany).

Schneider, "Enhanced Plasma Concentration by Selective Deuteration of Rofecoxib in Rats", Arzneim.-Forsch., Drug Res., vol. 56, No. 4 (2006), pp. 295-300.

Sugawara et al., "Eponemycin, A New Antibiotic Active Against B16 Melanoma," The Journal of Antibiotics, vol. 43(1), pp. 8-18 (1990).

Spaltenstein et al., "Design and Synthesis of Novel Protease Inhibitors. Tripeptide α', β'-Epoxyketones as Nanomolar Inactivators of the Proteasome," Teirahedron Letters, vol. 37(9), pp. 1343-1346 (1996).

Taber, D., "Asymmetric Nucleophillic Epoxidation", Org. Chem. Highlights, (2004).

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Toom, L., "Microwave-Assisted Raney Nickel Reduction of Bispidinone Thioketals to N,N'-Dialkylbispidines", Synthesis, vol. 12 (2006), pp. 2064-2068.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F., "P1 and P3 optimization of novel bicycloproline P2 bearing tetrapeptidyl alpha-ketoamide based HCV protease inhibitors", Bioorganic & Medicinal Chemistry Letters, 14 (2004) pp. 257-261.

Vishweshwar, P., "Pharmaceutical Co-Crystals", J. Pharm. Sci., vol. 95, No. 3 (2006), pp. 499-516.

Wang, Z., "Asymmetric Epoxidation of trans-β-Mefhylstyrene and 1-Phenylcyclohexene Using a D-Fructose-Derived. Ketone: (R,R)-trans-β-Methylstyrene Oxide and (R,R)-1-Phenylcyclohexene Oxide", Org. Syntheses, vol. 80 (2003), p. 9.

White, P.W., "Blunting the Swiss Army Knife of Hepatitis C Virus. Inhibitors of NS3/4A Protease" Progress in Medicinal Chemistry 44 (2006), pp. 65-107.

Wolff, "Burger's Medicinal Chemistry and Drug Discovery", Wiley-Interscience, 5th Edition, vol. 1: Principles and Practice, 975-977, 1994.

Yao, N., "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. and Pharm. Bulletin (1995), pp. 1318-1324.

Yee, Ying K. et al., "A Novel Series of Selective Leukotriene Antagonists: Exploration and Optimization of the Acidic Region in 1,6-Disubstituted Indoles and Indazoles," J. Med. Che., 33(9), pp. 2437-2451 (1990).

Yip, Y., "Discovery of a Novel Bicycloproline P2 Bearing Peptidyl a-Ketoamide LY514962 as HCV Protease Inhibitor", Bio. & Med. Chem. Let., vol. 14, No. 1 (2005), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Martell et al., "High-Throughput Real-Time Reverse Transcription-PCR Quantitation of Hepatitis C Virus RNA," Journal of Clinical Microbiology, Feb. 1999, pp. 327-332.

INHIBITORS OF SERINE PROTEASES, PARTICULARLY HCV NS3-NS4A PROTEASE

CROSS-REFERENCE TO RELATED APPLICATIONS

This application is a continuation of U.S. patent application Ser. No. 12/082,668, filed Apr. 10, 2008 (now U.S. Pat. No. 7,745,444), which application is a continuation of U.S. patent application Ser. No. 10/936,450, filed Sep. 7, 2004 (now U.S. Pat. No. 7,378,422), which application claims priority to U.S. Provisional Patent Application 60/500,670, filed Sep. 5, 2003. The entire disclosures of these prior applications are incorporated herein by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention also relates to processes for preparing these compounds. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et. al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et. al., "Expression and Identification of Hepatitis C Virus Polyprotein Cleavage Products," *J. Virol.*, 67, pp. 1385-1395 (1993); L. Tomei et. al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described [PCT publication Nos. WO 02/18369, WO 02/08244, WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., *Bioorg. Med. Chem. Lett.*, 8, pp. 1713-18 (1998); W. Han et al., *Bioorg. Med. Chem. Lett.*, 10, 711-13 (2000); R. Dunsdon et al., *Bioorg. Med. Chem. Lett.*, 10, pp. 1571-79 (2000); M. Llinas-Brunet et al., *Bioorg. Med. Chem. Lett.*, 10, pp. 2267-70 (2000); and S. LaPlante et al., *Bioorg. Med. Chem. Lett.*, 10, pp. 2271-74 (2000)].

There are not currently any satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and induce long term remission in only a fraction (~25%) of cases [O. Weiland, "Interferon Therapy in Chronic Hepatitis C Virus Infection", *FEMS*

*Microbiol. Rev.*, 14, pp. 279-288 (1994)]. Moreover, the prospects for effective anti-HCV vaccines remain uncertain.

Thus, there is a need for compounds useful in anti-HCV therapies. Such compounds would have therapeutic potential as protease inhibitors, particularly as serine protease inhibitors, and more particularly as HCV NS3 protease inhibitors. These compounds would be useful as antiviral agents, particularly as anti-HCV agents. There is a particular need for compounds with improved enzyme inhibition or cellular activity.

SUMMARY OF THE INVENTION

The present invention addresses these needs by providing a compound of formula I:

I wherein the variables are as defined herein.

The invention also relates to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

The invention also relates to processes for preparing the compounds of formula I.

DETAILED DESCRIPTION OF THE INVENTION

The present invention provides a compound of formula I:

I wherein:
Ar is a 5- to 10-membered aromatic ring having up to 4 heteroatoms selected from O, S, N(H), SO, and $SO_2$, wherein 1 to 3 ring atoms are optionally and independently substituted with J;
$R^1$ and $R^2$ are independently:
 (C1-C12)-aliphatic-,
 (C3-C10)-cycloalkyl- or -cycloalkenyl-,
 [(C3-C10)-cycloalkyl- or -cycloalkenyl]-(C1-C12)-aliphatic-,
 (C6-C10)-aryl-(C1-C12)aliphatic-,
 (C6-C10)-heteroaryl-(C1-C12)aliphatic-,
  wherein up to 3 aliphatic carbon atoms in $R^1$ and $R^2$ may be replaced by a heteroatom selected from O, N, S, SO, or $SO_2$ in a chemically stable arrangement;
  wherein each of $R^1$ and $R^2$ is independently and optionally substituted with up to 3 substituents independently selected from J;
$R^3$ and $R^{3'}$ are independently hydrogen or (C1-C12)-aliphatic, wherein any hydrogen is optionally replaced with halogen; wherein any terminal carbon atom of $R^3$ is optionally substituted with sulfhydryl or hydroxy; or $R^3$ is phenyl or —$CH_2$-phenyl, wherein said phenyl group is optionally substituted with up to 3 substituents independently selected from J; or
$R^3$ and $R^{3'}$ together with the atom to which they are bound is a 3- to 6-membered ring having up to 2 heteroatoms selected from N, NH, O, SO, or $SO_2$; wherein the ring has up to 2 substituents selected independently from J;
$R^4$ and $R^{4'}$ are independently:
 hydrogen-,
 (C1-C12)-aliphatic-,
 (C3-C10)-cycloalkyl- or -cycloalkenyl-,
 (C3-C10)-cycloalkyl-(C1-C12)-aliphatic-,
 (C6-C10)-aryl-,
 (C3-C10)-heterocyclyl-; or
 (C5-C10)-heteroaryl-;
  wherein up to two aliphatic carbon atoms in $R^4$ and $R^{4'}$ may be replaced by a heteroatom selected from O, N, S, SO, or $SO_2$;
  wherein each of $R^4$ and $R^{4'}$ is independently and optionally substituted with up to 3 substituents independently selected from J;
W is:

wherein each $R_6$ is independently:
 hydrogen-,
 (C1-C12)-aliphatic-,
 (C6-C10)-aryl-,
 (C6-C10)-aryl-(C1-C12)aliphatic-,
 (C3-C10)-cycloalkyl- or cycloalkenyl-,
 [(C3-C10)-cycloalkyl- or cycloalkenyl]-(C1-C12)-aliphatic-,
 (C3-C10)-heterocyclyl-,
 (C3-C10)-heterocyclyl-(C1-C12)-aliphatic-,
 (C5-C10)heteroaryl-, or
 (C5-C10)heteroaryl-(C1-C12)-aliphatic-, or
 two $R_6$ groups, which are bound to the same nitrogen atom, form together with that nitrogen atom, a (C3-C10)-heterocyclic ring;
  wherein $R_6$ is optionally substituted with up to 3 J substituents;

wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;

T is:
  (C1-C12)-aliphatic-;
  (C6-C10)-aryl-,
  (C6-C10)-aryl-(C1-C12)aliphatic-,
  (C5-C10)heteroaryl-, or
  (C5-C10)heteroaryl-(C1-C12)-aliphatic-;
    wherein each T is optionally substituted with up to 3 J substituents;

J is halogen, —OR', —$NO_2$, —CN, —$CF_2$, —$OCF_3$, —R', oxo, thioxo, 1,2-methylenedioxy, 1,2-ethylenedioxy, =N(R'), =N(OR'), —N(R')$_2$, —SR', —SOR', —$SO_2$R', —$SO_2$N(R')$_2$, —$SO_3$R', —C(O)R', —C(O)C(O)R', —C(O)CH$_2$C(O)R', —C(S)R', —C(S)OR', —C(O)OR', —C(O)C(O)OR', —C(O)C(O)N(R')$_2$, —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

R' is independently selected from:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, or
  (C5-C10)-heteroaryl-(C1-C12)-aliphatic-;
    wherein R' is optionally substituted with up to 3 J groups;
    wherein two R' groups bound to the same atom form a 3- to 10-membered aromatic or non-aromatic ring having up to 3 heteroatoms independently selected from N, O, S, SO, or $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J.

These compounds solve the above problems by providing compounds with improved enzyme and/or cell activity. For example, compounds of this invention, particularly the preferred compounds exhibit better enzyme inhibition than the compounds of WO 98/17679. The compounds of this invention also have better cellular data than other reported compounds (see the documents cited herein).

In one embodiment, if $R^1$ is cyclohexyl, $R^2$ is t-butyl, $R^{3'}$ is H, $R^3$ is n-propyl, W is —C(O)C(O)N(H)-cyclopropyl, and T is:

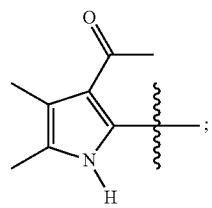

then Ar is 4-quinazoline or 5-chloro-2-pyridyl.

The present invention also provides a compound of formula I:
wherein:

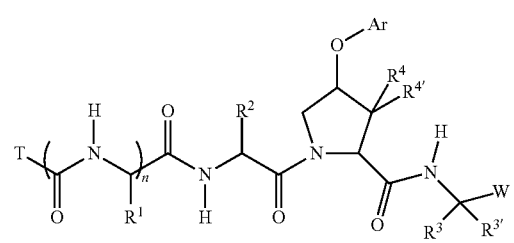

I n is 0 or 1;
Ar is a 5- to 10-membered aromatic ring having up to 4 heteroatoms selected from 0, S, N(H), SO, and $SO_2$, wherein 1 to 3 ring atoms are optionally and independently substituted with J;
$R^1$, $R^2$, $R^{12}$, and $R^{13}$ are independently:
  (C1-C12)-aliphatic-,
  (C3-C10)-cycloalkyl- or -cycloalkenyl-,
  [(C3-C10)-cycloalkyl- or -cycloalkenyl]-(C1-C12)-aliphatic-,
  (C6-C10)-aryl-(C1-C12)aliphatic-,
  (C6-C10)-heteroaryl-(C1-C12)aliphatic-,
    wherein up to 3 aliphatic carbon atoms in $R^1$ and $R^2$ may be replaced by a heteroatom selected from O, N, NH, S, SO, or $SO_2$ in a chemically stable arrangement;
    wherein each of $R^1$ and $R^2$ is independently and optionally substituted at each substitutable position with up to 3 substituents independently selected from J;
$R^3$ and $R^{3'}$ are independently hydrogen or (C1-C12)-aliphatic, wherein any hydrogen is optionally replaced with halogen; wherein any terminal carbon atom of $R^3$ is optionally substituted with sulfhydryl or hydroxy; or $R^3$ is phenyl or —CH$_2$-phenyl, wherein said phenyl group is optionally substituted with up to 3 substituents independently selected from J; or
$R^3$ and $R^{3'}$ together with the atom to which they are bound is a 3- to 6-membered ring having up to 2 heteroatoms selected from N, NH, O, SO, and $SO_2$; wherein the ring has up to 2 substituents selected independently from J;
$R^4$ and $R^{4'}$ are independently:
  hydrogen-,
  (C1-C12)-aliphatic-,
  (C3-C10)-cycloalkyl- or -cycloalkenyl-,
  (C3-C10)-cycloalkyl-(C1-C12)-aliphatic-,
  (C6-C10)-aryl-,
  (C3-C10)-heterocyclyl-; or
  (C5-C10)-heteroaryl-;
    wherein up to two aliphatic carbon atoms in $R^4$ and $R^{4'}$ may be replaced by a heteroatom selected from O, N, S, SO, and $SO_2$;

wherein each of $R^4$ and $R^{4'}$ is independently and optionally substituted with up to 3 substituents independently selected from J;

W is:

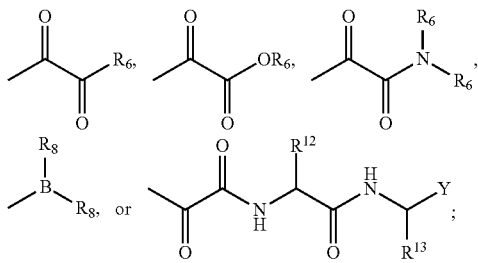

wherein
Y is —$CO_2H$, a derivative of —$CO_2H$, or a bioisostere of —$CO_2H$;
each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)heteroaryl-, or
(C5-C10)heteroaryl-(C1-C12)-aliphatic-, or
two $R_6$ groups, which are bound to the same nitrogen atom, form together with that nitrogen atom, a (C3-C10)-heterocyclic ring;
wherein $R_6$ is optionally substituted with up to 3 J substituents;
wherein each $R_8$ is independently —OR'; or the $R_8$ groups together with the boron atom, is a (C3-C10)-membered heterocyclic ring having in addition to the boron up to 3 additional heteroatoms selected from N, NH, O, SO, and $SO_2$;

T is:
(C1-C12)-aliphatic-;
(C6-C10)-aryl-,
(C6-C10)-aryl-(C1-C12)aliphatic-,
(C5-C10)heteroaryl-, or
(C5-C10)heteroaryl-(C1-C12)-aliphatic-;
wherein each T is optionally substituted with up to 3 J substituents; and
wherein up to 3 aliphatic carbon atoms in T may be replaced by a heteroatom selected from O, N, NH, S, SO, or $SO_2$ in a chemically stable arrangement;
provided that if T is pyrrole, the pyrrole is not substituted at the 3-position with J, with J being —C(O)R', —C(O)C(O)R', —C(O)$CH_2$C(O)R', —C(S)R', —C(S)OR', —C(O)OR', —C(O)C(O)OR', —C(O)C(O)N(R')$_2$, —C(O)N(R')$_2$, —C(S)N(R')$_2$, —C(=NH)N(R')$_2$, —C(O)N(OR')R', or —C(=NOR')R';

J is halogen, —OR', —$NO_2$, —CN, —$CF_3$, —$OCF_3$, —R', oxo, thioxo, 1,2-methylenedioxy, 1,2-ethylenedioxy, =N(R'), =N(OR'), —N(R')$_2$, —SR', —SOR', —$SO_2$R', —$SO_2$N(R')$_2$, —$SO_3$R', —C(O)R', —C(O)C(O)R', —C(O)$CH_2$C(O)R', —C(S)R', —C(S)OR', —C(O)OR', —C(O)C(O)OR', —C(O)C(O)N(R')$_2$, —OC(O)R', —C(O)N(R')$_2$, —OC(O)N(R')$_2$, —C(S)N(R')$_2$, —($CH_2$)$_{0-2}$NHC(O)R', —N(R')N(R')COR', —N(R')N(R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

R' is:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-;
wherein R' is optionally substituted with up to 3 J groups;
wherein two R' groups bound to the same atom form a 3- to 10-membered aromatic or non-aromatic ring having up to 3 heteroatoms independently selected from N, O, S, SO, or $SO_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J.

In one embodiment, if $R^1$ is cyclohexyl, $R^2$ is t-butyl, $R^{3'}$ is H, $R^3$ is n-propyl, W is —C(O)C(O)N(H)— cyclopropyl, and T is:

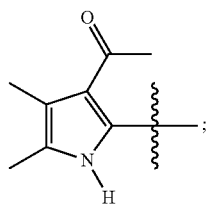

then Ar is not 4-quinazoline or 5-chloro-2-pyridyl.

In another embodiment, if T is pyrrole, the pyrrole is not substituted with J, but is optionally fused to a 5-membered or a 6-membered aryl or heteroaryl ring.

In another embodiment, if T is pyrrole, the pyrrole is not substituted at the 3-position with J, but is optionally fused to a 5-membered or a 6-membered aryl or heteroaryl ring.

In another embodiment, T is not

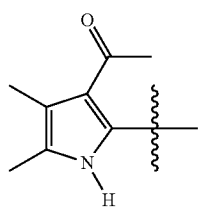

In another embodiment, T is not pyrrole.

In a more specific embodiment, this invention provides a compound wherein n is 0 and the compound has the formula I-A:

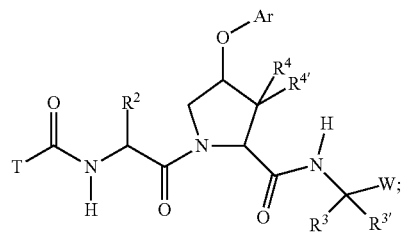

I-A wherein the variable are as defined in any of the embodiments herein. In a compound of formula A, W is preferably:

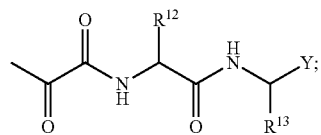

In another specific embodiment, this invention provides a compound wherein n is 1 and the compound has the formula I-B:

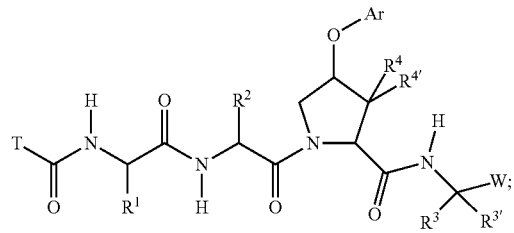

I-B wherein the variable are as defined in any of the embodiments herein. In a compound of formula I-B, W is preferably:

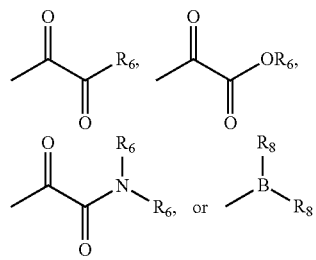

DEFINITIONS

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin.

The term "bioisostere" —$CO_2H$ as used in herein refers to a chemical moiety which may substitute for a carboxylic acid group in a biologically active molecule. Examples of such groups are disclosed in Christopher A. Lipinski, "Bioisosteres in Drug Design" *Annual Reports in Medicinal Chemistry*, 21, pp. 286-88 (1986), and in C. W. Thornber, "Isosterism and Molecular Modification in Drug Design" *Chemical Society Reviews*, pp. 563-580 (1979). Examples of such groups include, but are not limited to, —$COCH_2OH$, —CONHOH, $SO_2NHR'$, —$SO_3H$, —$PO(OH)NH_2$, —CONHCN, —$OSO_3H$, —$CONHSO_2R'$, —$PO(OH)_2$, —PO(OH)(OR'), —PO(OH)(R'), —$OPO(OH)_2$—OPO(OH)(OR'), —OPO(OH)(R'), $HNPO(OH)_2$, —NHPO(OH)(OR'), —NHPO(OH)(R')

The term "heterocyclyl" as used herein means a monocyclic or bicyclic non-aromatic ring system having 1 to 3 heteroatom or heteroatom groups in each ring selected from O, N, NH, S, SO, or $SO_2$ in a chemically stable arrangement. In a bicyclic non-aromatic ring system embodiment of "heterocyclyl" one or both rings may contain said heteroatom or heteroatom groups.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein means a monocyclic or bicyclic aromatic ring system having 1 to 3 heteroatom or heteroatom groups in each ring selected from O, N, NH or S in a chemically stable arrangement. In such a bicyclic aromatic ring system embodiment of "heteroaryl":

one or both rings may be aromatic; and one or both rings may contain said heteroatom or heteroatom groups.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl)-2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "aliphatic" as used herein means a straight chained or branched alkyl, alkenyl or alkynyl. It is understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

Preferred Embodiments

In another embodiment of this invention, Ar is phenyl, pyridyl, quinolinyl, pyrimidinyl, or naphthyl, wherein each group is optionally substituted with 1, 2, or 3 J groups.

In another embodiment of this invention, Ar is

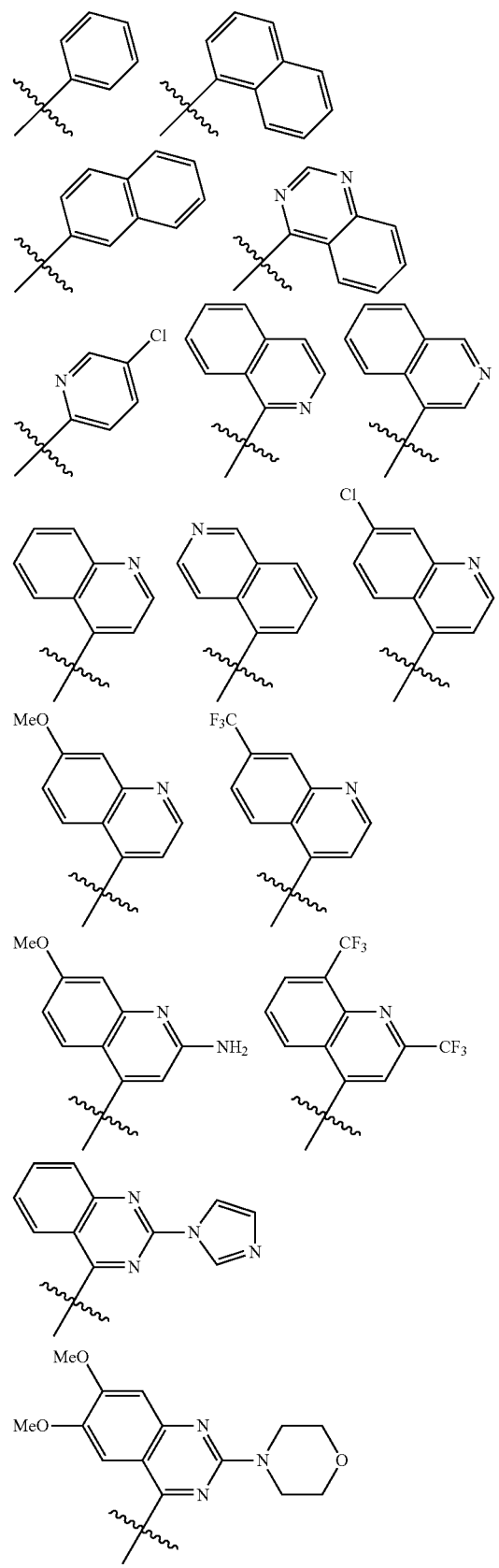

-continued

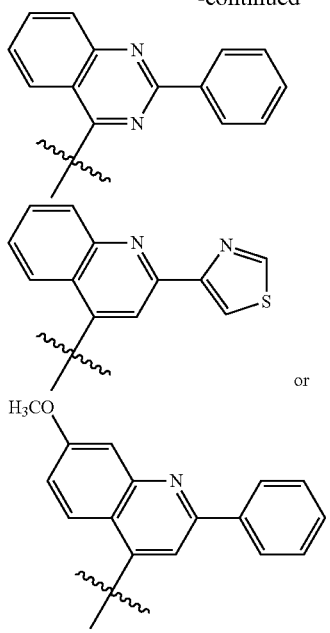

In another embodiment of this invention, Ar is:

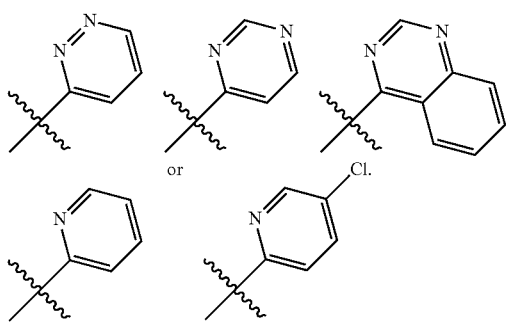

In a particularly favorable embodiment, Ar is:

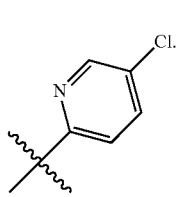

In another embodiment of this invention, Ar is a 6 or a 10-membered aromatic ring having 0, 1, or 2 nitrogen heteroatoms, wherein 1, 2, or 3 ring atoms are optionally and independently substituted with J.

In any of the embodiments of this invention, each J group on Ar is independently OR', NO$_2$, CN, CF$_3$, OCF$_3$, R', COR', C(O)OR', C(O)N(R')$_2$, SO$_2$R', SO$_2$N(R')$_2$, 1,2-methylenedioxy, 1,2-ethylene dioxy, or NR'C(O)OR', NR'SO$_2$R'.

In any of embodiments of this invention, each J group on Ar is preferably, and independently, OR', halogen, CN, CF$_3$, R', or COR'. More preferably, this J is halogen (particularly chloro).

In another embodiments of this invention, each J group on Ar is independently halo, trifluoromethyl, methyl, or NO$_2$.

According to any preferred embodiment, T is (C6-C10)-aryl- or (C5-C10)heteroaryl-, wherein each T is optionally substituted with 1, 2, or 3 J substituents.

In a preferred embodiment, T is a 6-membered or a 10-membered aryl group. In another preferred embodiment, T is a 6-membered heteroaryl group that is optionally fused to another 5- or 6-membered aryl or heteroaryl group.

More preferred embodiments are those wherein T:

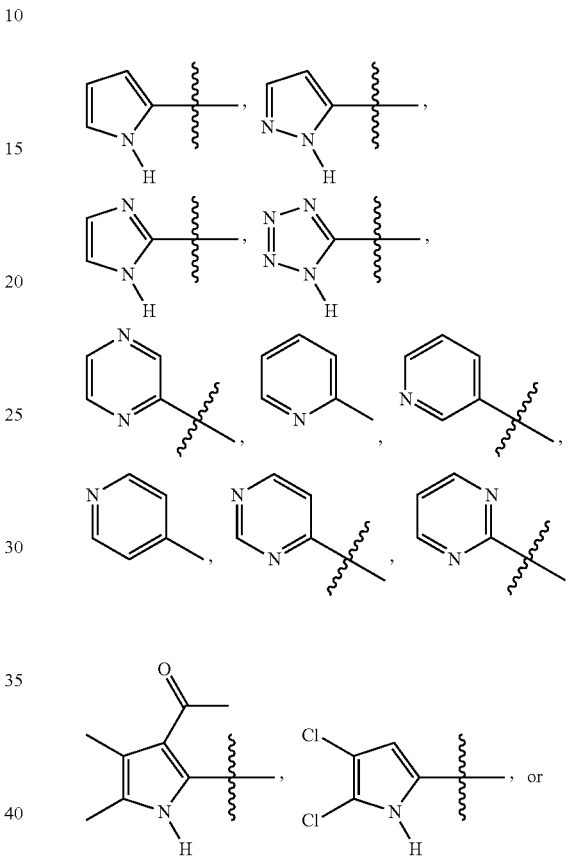

In a more preferred embodiment, T is:

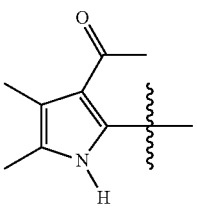

or pyrazine.

In certain embodiments of this invention, any T group is optionally fused to a 5-membered or a 6-membered aryl or heteroaryl group.

Accordingly, one embodiment of this invention provides compounds wherein T is:

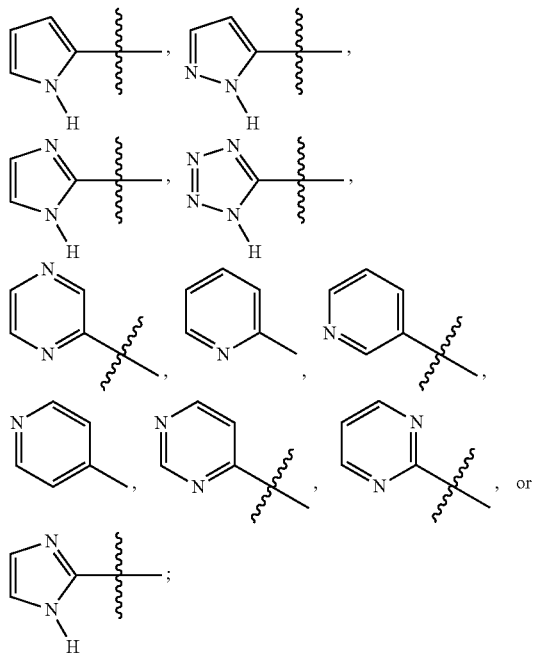

wherein each T group is optionally fused to a 5-membered or a 6-membered aryl or heteroaryl group.

In another embodiment, T is:

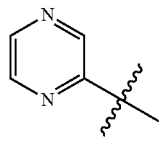

wherein T is optionally fused to a 5-membered or a 6-membered aryl or heteroaryl group.

In certain embodiments, T is not fused to another ring.

In any embodiment of this invention, each aryl or heteroaryl group of T is optionally and independently substituted with 1, 2, or 3 groups selected from —CH₃, —H₂CH₃, halogen, acetyl, —CO₂H, —(C1-C6-alkyl)-CO₂H, or —O₂R'.

In certain embodiments, 1 aliphatic carbon atom in T is replaced by a heteroatom selected from O, N, NH, S, SO, or SO₂ in a chemically stable arrangement. The heteroatom is preferably, O or NH. In an alternative embodiment no aliphatic carbon atom is replaced with T.

In certain compounds of this invention, an aliphatic group links to T to the remainder of the molecule. In general, in these aliphatic linkers replacement of an aliphatic carbon atom is preferred in compounds wherein n is 0. In compounds wherein n is 1, this aliphatic linker group, preferably, has no heteroatom replacements. Furthermore, compounds wherein n is 1, preferably, have no aliphatic linker group.

According to a preferred embodiment, W is —C(O)—C(O)—R₆. Preferably, R₆ is phenyl, pyridyl, (C3-C6)-alkyl, (C3-C6)-cycloalkyl, —OH, —O—(C1-C6)-alkyl, —N(H)—(C3-C6)-cycloalkyl, —N(H)—C(H)(CH₂)—(C6-C10)aryl, —N(H)—C(H)(CH₂)—(C3-C10)-heterocylyl, or —N(H)—C(H)(CH₂)—(C5-C10)-heteroaryl, wherein each aryl, heterocyclyl, and heteroaryl is optionally substituted with halogen. Preferred embodiments are selected from:

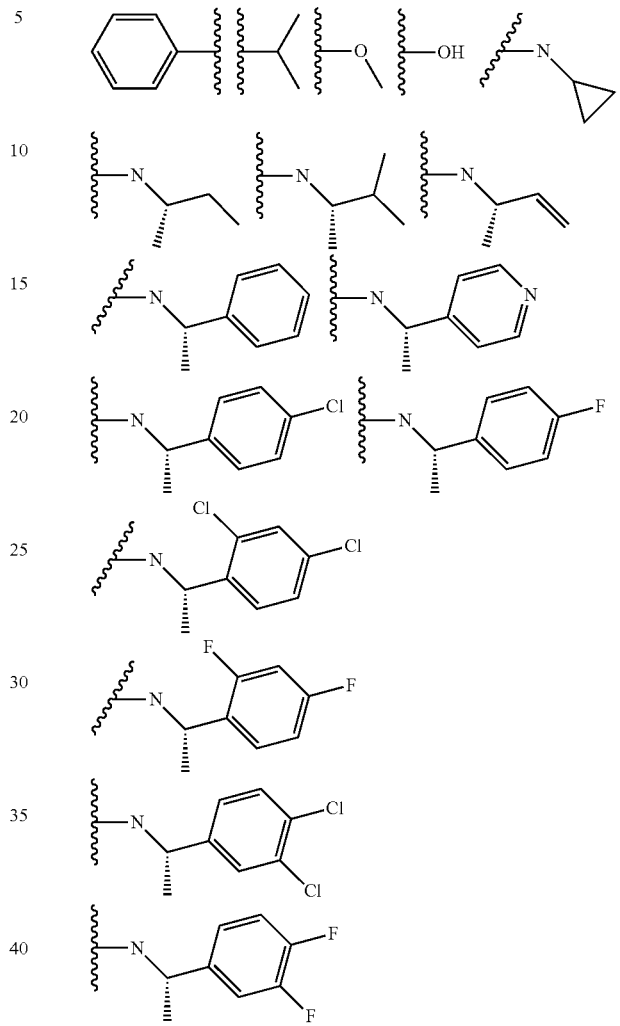

More preferably, R₆ is isopropyl.

According to one embodiment, W is —C(O)—C(O)—OR₆. In this embodiment, R₆ is preferably hydrogen, (C1-C12)-aliphatic (more preferably, C1-C6-alkyl), (C6-C10)-aryl, (C3-C10)-cycloalkyl or -cycloalkenyl, (C3-C10)-heterocyclyl, (C5-C10)heteroaryl, or C3-C6-cycloalkyl-(C1-C3)-alkyl, wherein the cycloalkyl is preferably a cyclopropyl group. The aryl group is optionally substituted with up to 3 J groups, wherein J is halogen, preferably chloro or fluoro. More preferably, R₆ is H or methyl.

According to another embodiment, W is —C(O)—C(O)—N(R₆)₂, wherein R₆ is hydrogen, (C1-C6)-alkyl, (C1-C6)-alkenyl, (C6-C10)-aryl-(C1-C6)-alkyl-, or (C6-C10)-heteroaryl-(C1-C6)-alkyl-, wherein R₆ is optionally substituted with up to 3 J groups. Preferably, R₆ is hydrogen, (C3-C10)-cycloalkyl or -cycloalkenyl, or (C3-C10)-heterocyclyl. Alternatively, one R₆ is hydrogen and the other R₆ is (C6-C10)-aryl-(C1-C3)alkyl-, wherein the alkyl is optionally substituted with CO₂H; (C3-C6)cycloalkyl-; (C5)-heterocyclyl-(C1-C3)alkyl-; (C3-C6)alkenyl-; or each R₆ is (C1-C6)-alkyl-. Alternatively, each R₆ is (C1-C3)-alkyl-.

Most preferably, —NHR$_6$ in W is:

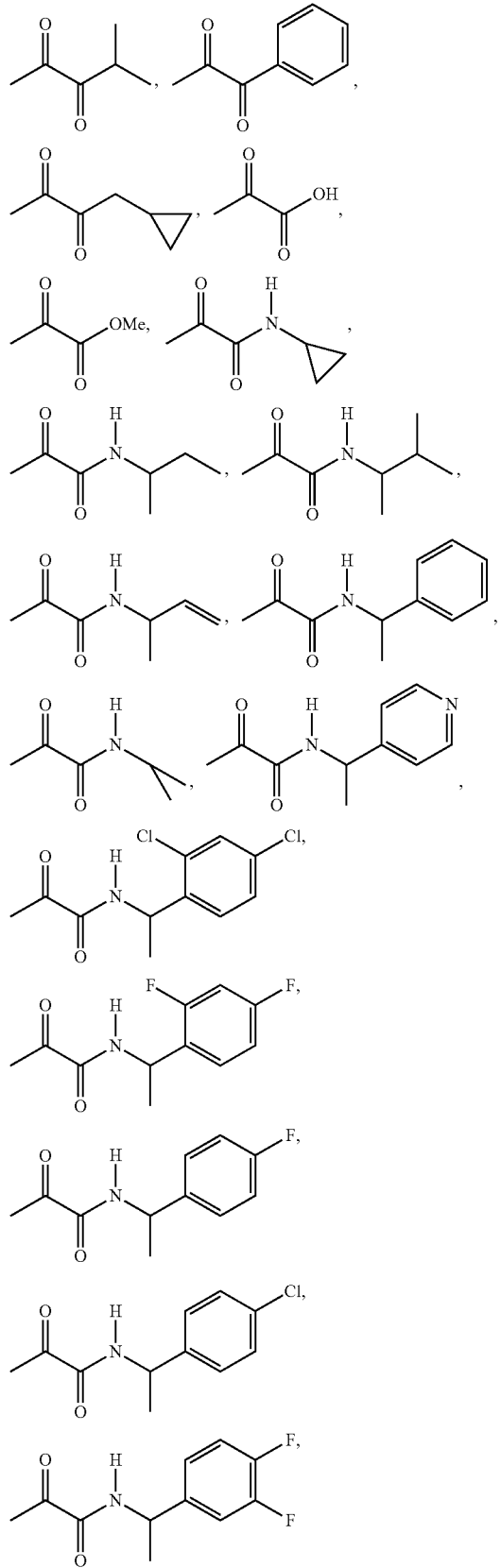

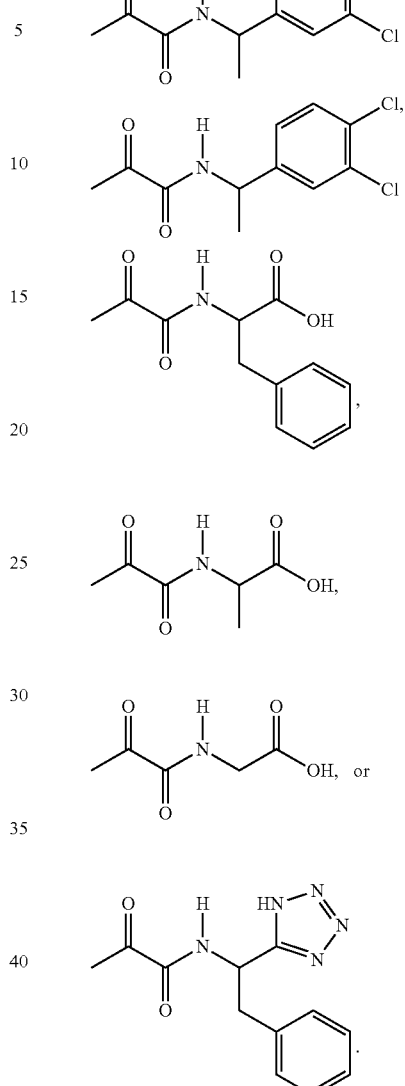

Preferred J substituents on the alkyl and aryl groups in this embodiment are halogen, carboxy, and heteroaryl. More preferred substituents on the aryl groups are halogen (preferably chloro or fluoro) and more preferred J substituents on the alkyl groups are carboxy and heteroaryl.

According to yet other preferred embodiments of formula I, W is:

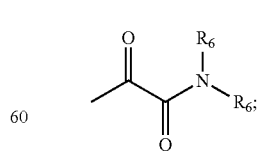

wherein the NR$^6$R$^6$ is —NH—(C1-C6 aliphatic), —NH—(C3-C6 cycloalkyl), —NH—CH(CH$_3$)-aryl, or —NH—CH(CH$_3$)-heteroaryl, wherein said aryl or said heteroaryl is optionally substituted with up to 3 halogens.

In any preferred embodiment of W, the NR⁶R⁶ is:
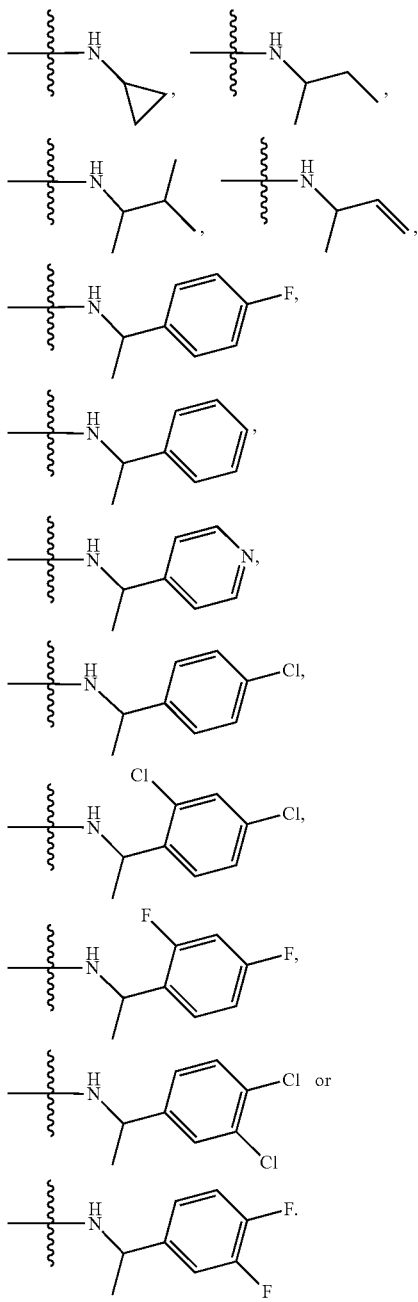
In any preferred embodiment of W, the NR⁶R⁶ is:
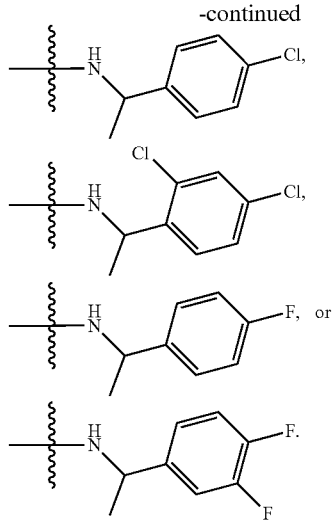
In any more preferred embodiment of W, the NR⁶R⁶ is:
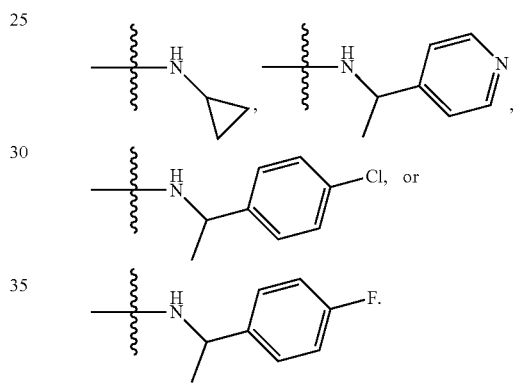
In any more preferred embodiment of W, the NR⁶R⁶ is:
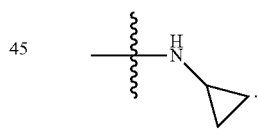
According to one embodiment, R¹ is selected from:
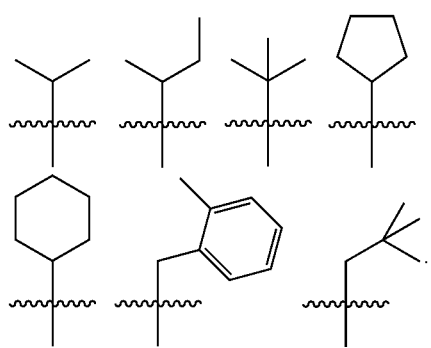

According to a preferred embodiment, $R^1$ is selected from:

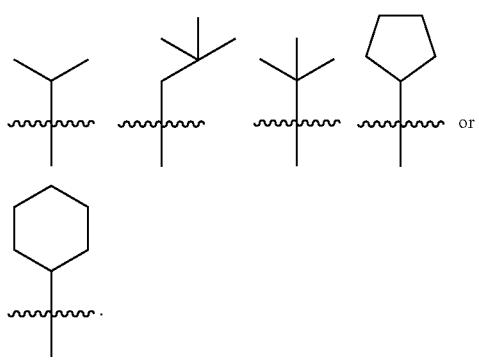

According to another embodiment, $R^1$ is:

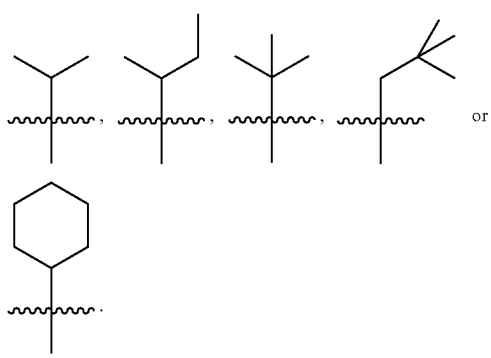

According to another embodiment, $R^1$ is:

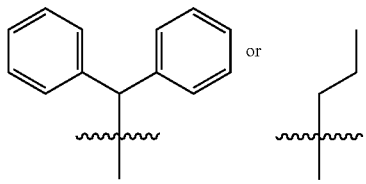

Most preferably, $R^1$ is cyclohexyl.
According to one embodiment, $R^2$ is:

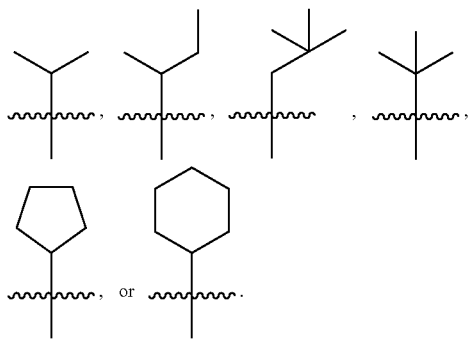

According to another embodiment, $R^2$ is

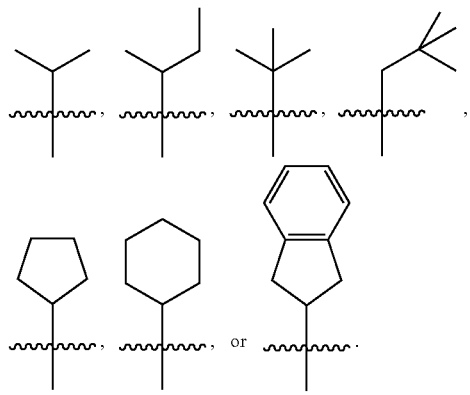

According to any preferred embodiments, $R^2$ is:

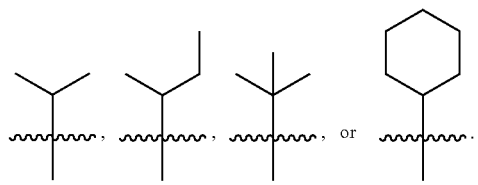

According to any more preferred embodiments, $R^2$ is:

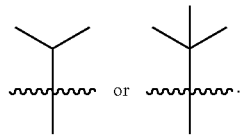

In any most preferred embodiments, $R^2$ is t-butyl.
According to one embodiment, $R^3$ is:

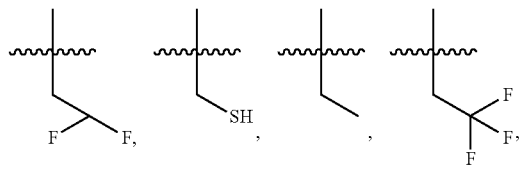

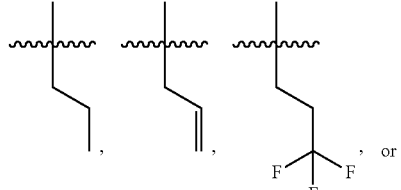

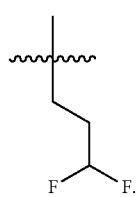

According to a preferred embodiment, R³ is:

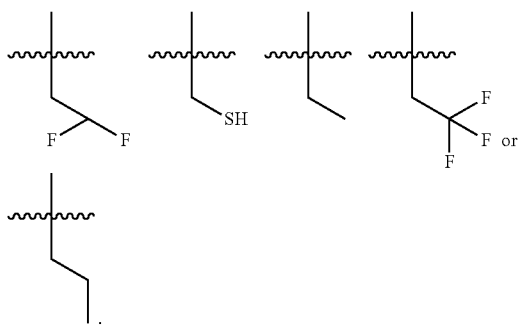

More preferably, R³ is propyl (preferably, n-propyl).

In any preferred embodiment of this invention, R³' is H.

According to another embodiment, R³ and R³' together with the atom to which they are bound form the ring system:

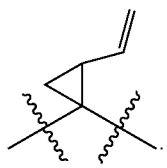

According to another embodiment, R³' is hydrogen and R³ is:

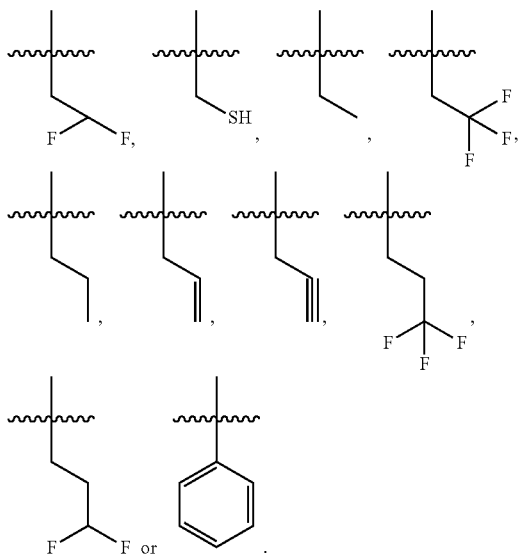

According to preferred embodiments, R³' is hydrogen and R³ is:

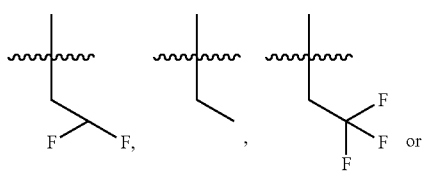

In yet other embodiments of this invention, R³' is hydrogen and R³ is:

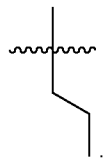

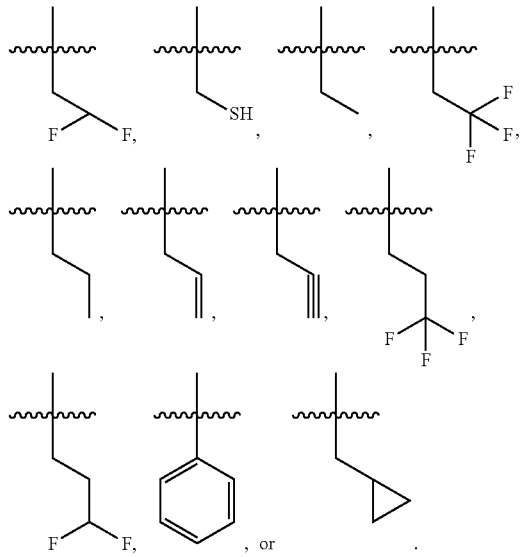

According to one embodiment, one of R⁴ or R⁴' is hydrogen.

According to another embodiment, one of R⁴ or R⁴' (C1-C6)-alkyl.

According to a preferred embodiment, R⁴ and R⁴' is hydrogen.

In certain embodiments, 1 or 2 carbon atoms of $R^1$, $R^2$, $R^3$, or $R^4$, are optionally and independently replaced with N, NH, O, or S.

Accordingly, one embodiment of this invention provides a compound wherein $R^1$ is cyclohexyl, wherein 1 or 2 carbon atoms is optionally replaced with N, NH, O, or S and wherein each atom is optionally and independently substituted with 1, 2, or 3 J groups, wherein J is halogen, OH, OR', NH, N(R')₂ (and R' is, preferably, (C1-C6)-alkyl).

In certain other embodiments no carbon atoms of $R^1$, $R^2$, $R^3$, and $R^4$ are replaced with N, NH, O, or S. In other embodiments these groups have no J substituents.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

Preferably, the compounds of this invention have the structure and stereochemistry depicted in compounds 1-76.

Any of the preferred embodiments recited above, including those embodiments in the above species, may define formula I individually or be combined to produce a preferred embodiment of this invention.

Abbreviations which are used in the schemes, preparations and the examples that follow are:

| | |
|---|---|
| THF: | tetrahydrofuran |
| DMF: | N,N,-dimethylformamide |
| EtOAc: | ethyl acetate |
| AcOH: | acetic acid |
| HOBt: | 1-hydroxybenzotriazolehydrate |
| EDC: | 1-(3-dimethylaminopropyl)-3-ethylcarbodiimide hydrochloride |
| NMM: | N-methylmorpholine |
| NMP: | N-methylpyyrolidinone |
| EtOH: | ethanol |
| t-BuOH: | tert-butanol |
| Et$_2$O: | diethyl ether |
| BOC: | tert-butyloxycarbonyl |
| BOC$_2$O: | di-tert-butyldicarbonate |
| Cbz: | benzyloxycarbonyl |
| Chg: | cyclohexylglycine |
| TbG: | tert-butylglycine |
| Fmoc: | 9-fluorenyl methyloxycarbonyl |
| DMSO: | diemthyl sulfoxide |
| TFA: | trifluoroacetic acid |
| DCCA: | dichloroacetic acid |
| DCE: | dichloroethane |
| DIEA: | diisopropylethylamine |
| MeCN: | acetonitrile |
| PyBrOP: | tris(pyrrolidino)bromophosphonium hexafluorophosphate |
| TBTU or HATU: | 2-(1H-benzotriazole-1-yl)-1,1,3,3-tetramethyluronium tetrafluoroborate |
| DMAP: | 4-aimethylaminopyridine |
| PPTS: | pyridinium p-toluenesulfonate |
| IBX: | periodobenzoic acid |
| AIBN: | 2,2'-azobisisobutyronitrile |
| TEMPO: | 2,2,6,6-tetramethyl-1-piperidinyloxy, free radical) |
| rt or RT: | room temperature |
| ON: | overnight |
| ND: | not determined |
| MS: | mass spectrometry |
| LC: | liquid chromatography |

General Synthetic Methodology:

The compounds of this invention may be prepared in general by methods known to those skilled in the art. Schemes 1-7 below illustrate synthetic routes to the compounds of the present invention. Other equivalent schemes, which will be readily apparent to the ordinary skilled organic chemist, may alternatively be used to synthesize various portions of the molecule as illustrated by the general schemes below, and the preparative examples that follow.

Scheme 1

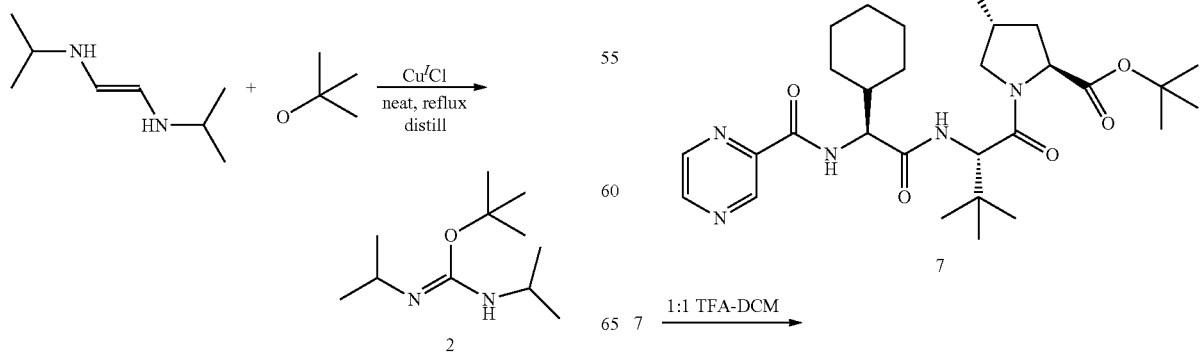

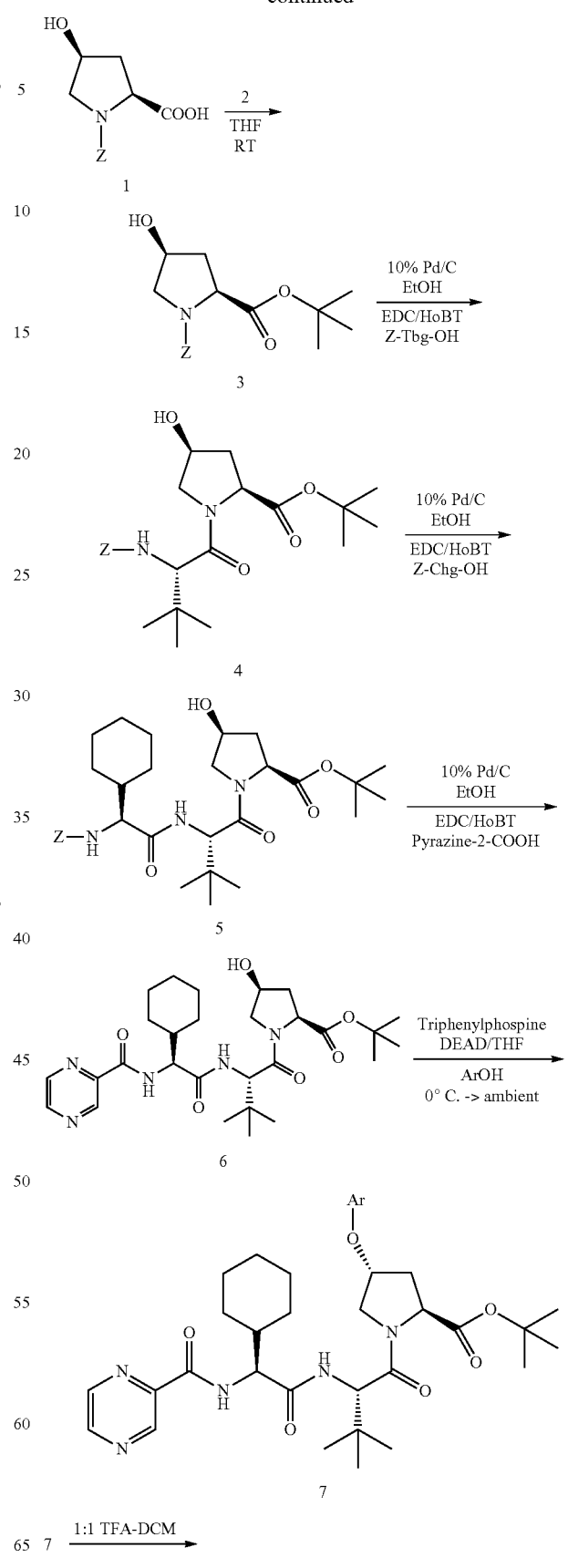

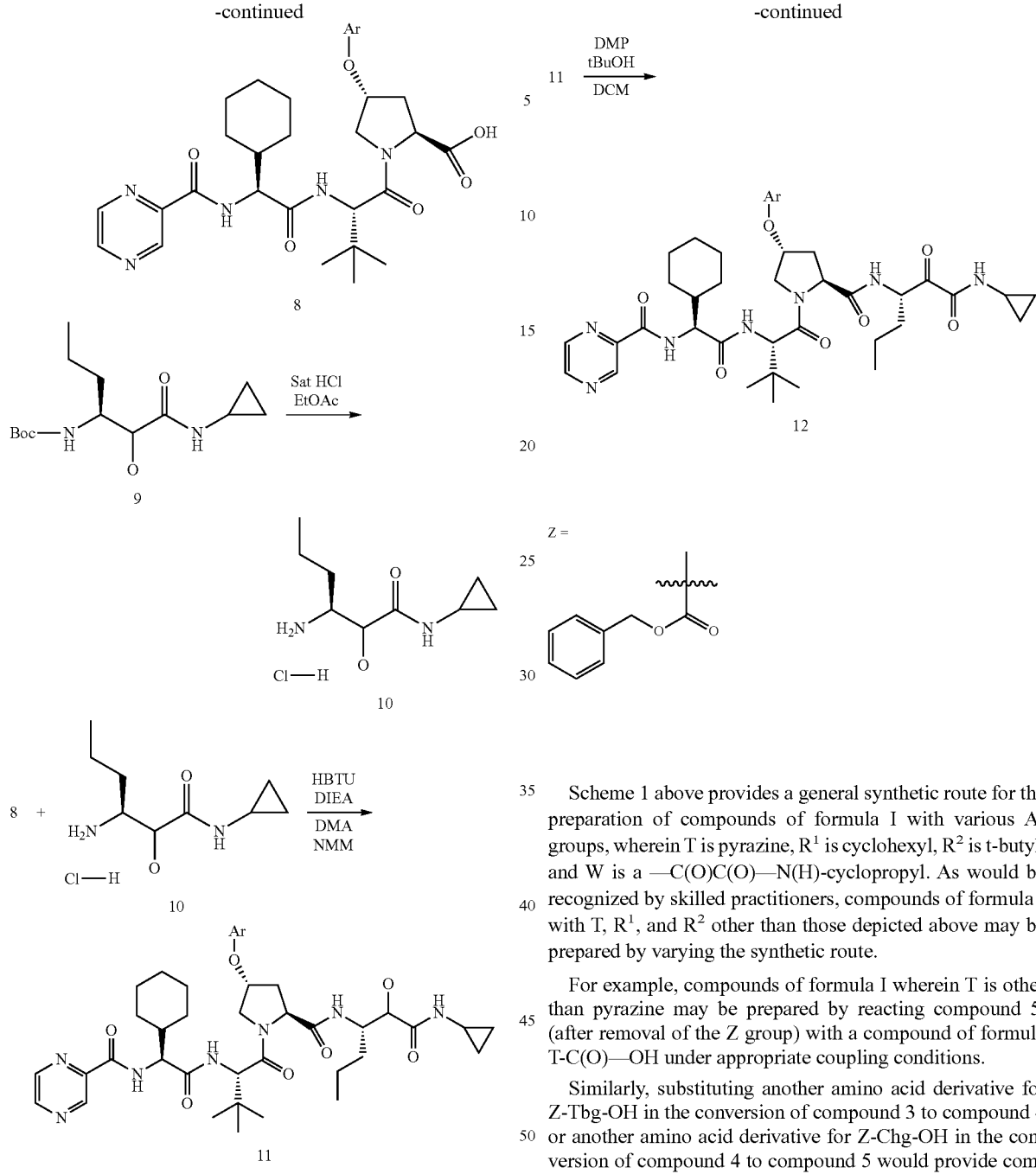

Scheme 1 above provides a general synthetic route for the preparation of compounds of formula I with various Ar groups, wherein T is pyrazine, $R^1$ is cyclohexyl, $R^2$ is t-butyl, and W is a —C(O)C(O)—N(H)-cyclopropyl. As would be recognized by skilled practitioners, compounds of formula I with T, $R^1$, and $R^2$ other than those depicted above may be prepared by varying the synthetic route.

For example, compounds of formula I wherein T is other than pyrazine may be prepared by reacting compound 5, (after removal of the Z group) with a compound of formula T-C(O)—OH under appropriate coupling conditions.

Similarly, substituting another amino acid derivative for Z-Tbg-OH in the conversion of compound 3 to compound 4 or another amino acid derivative for Z-Chg-OH in the conversion of compound 4 to compound 5 would provide compounds with varying $R^2$ and $R^1$ groups, respectively.

Scheme 2

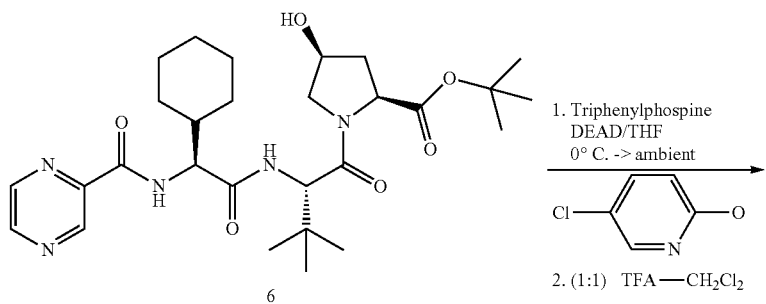

-continued
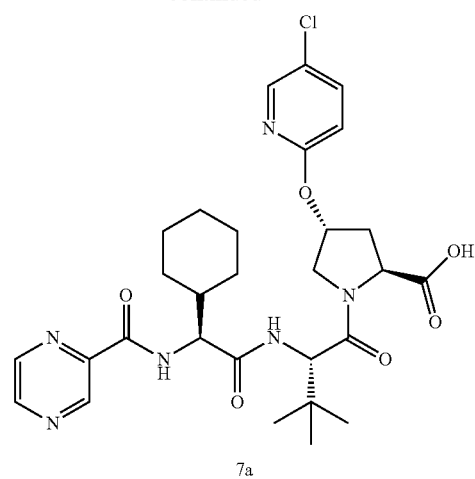
7a
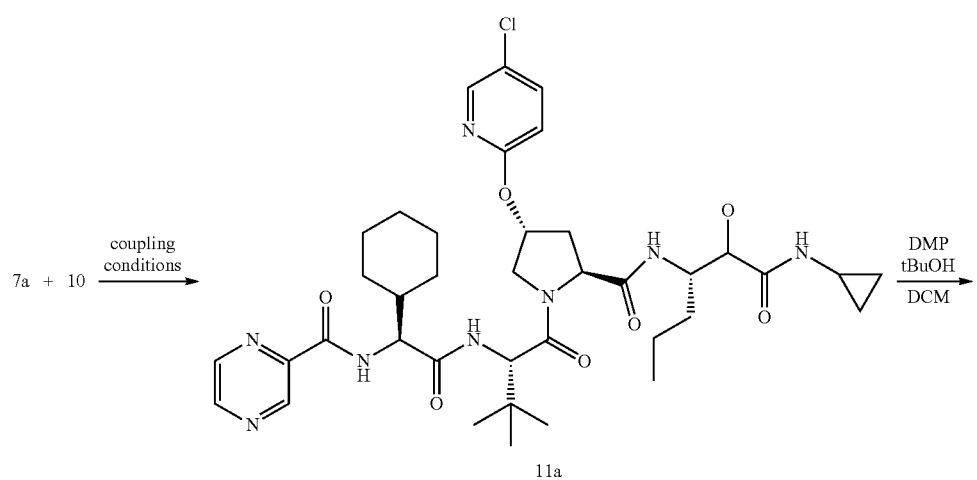
11a
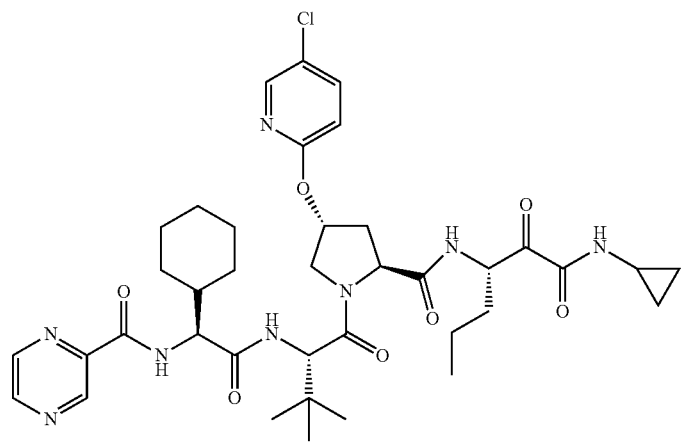
59

Scheme 2 above provides a general synthetic route for the preparation of compound 59.

An alternative approach to preparing compounds of this invention is depicted in Scheme 3. In this approach, a 4-hydroxyproline derivative 13 is reacted with a compound 14 to provide a compound 15. In Scheme 3, $P^1$ is hydrogen or an appropriate amine protecting group, $P^2$ is hydrogen or an appropriate carboxy protecting group, Ar is as defined herein, and X is an appropriate leaving group. In one embodiment set forth below, $P^1$ is t-butoxycarbonyl, $P^2$ is hydrogen, Ar is 4-chloro-2-pyridine, X is Cl, and 13 and 14 are reacted in the presence of tBuOK, DMSO, and THF.

As would be appreciated by skilled practitioners, the compound 15 then may be carried on to compounds of formula I by routine methods. One such method is depicted below in Scheme 4

Scheme 3

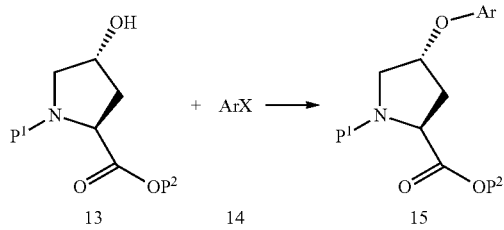

Scheme 4

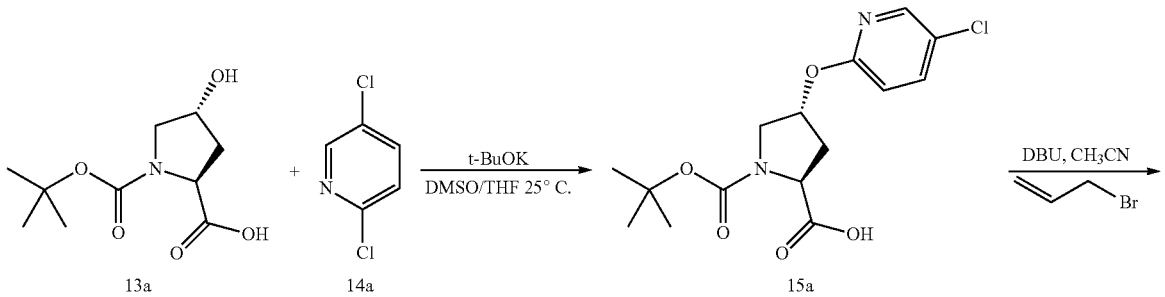

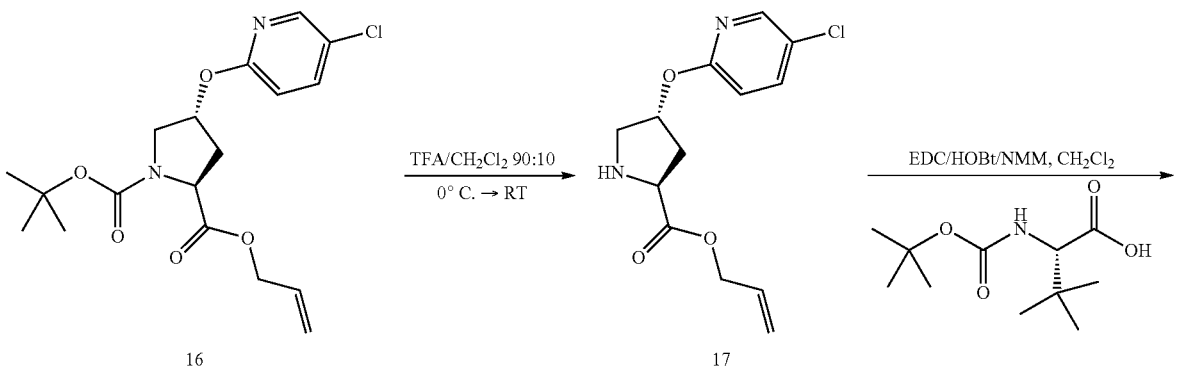

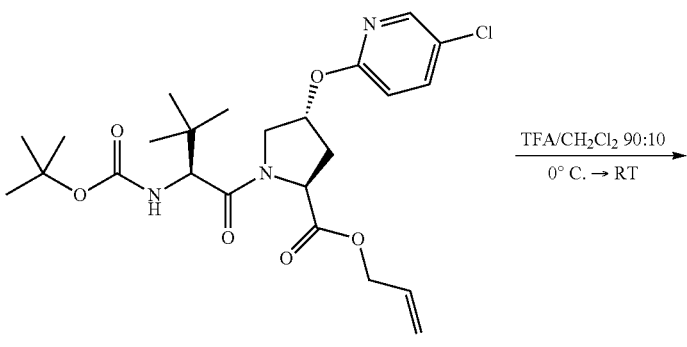

-continued
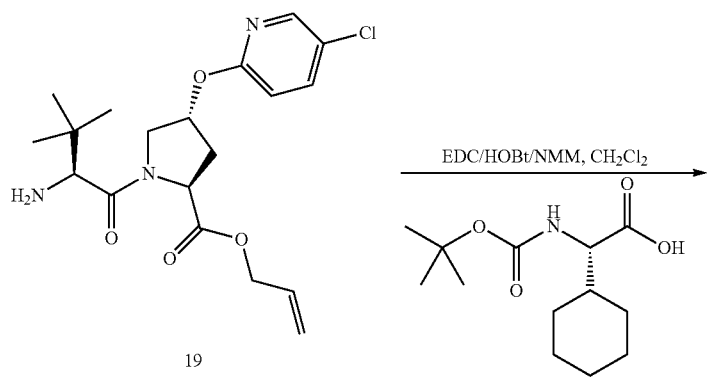
19
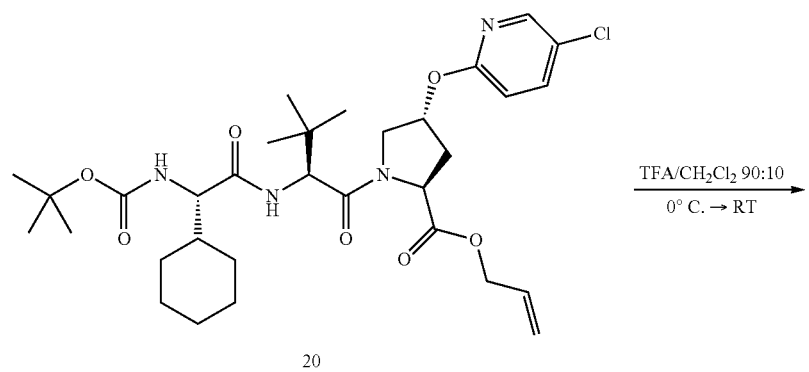
20
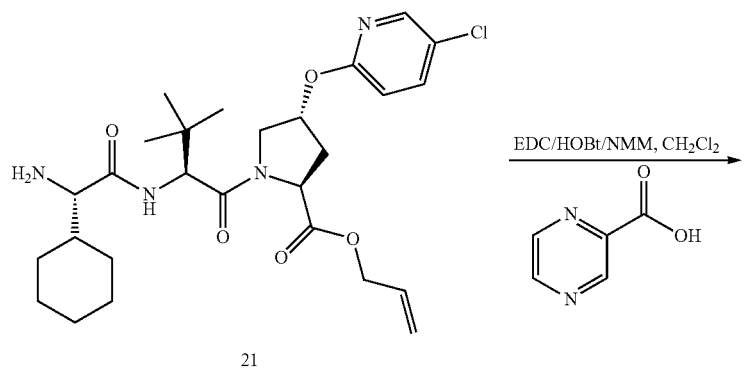
21
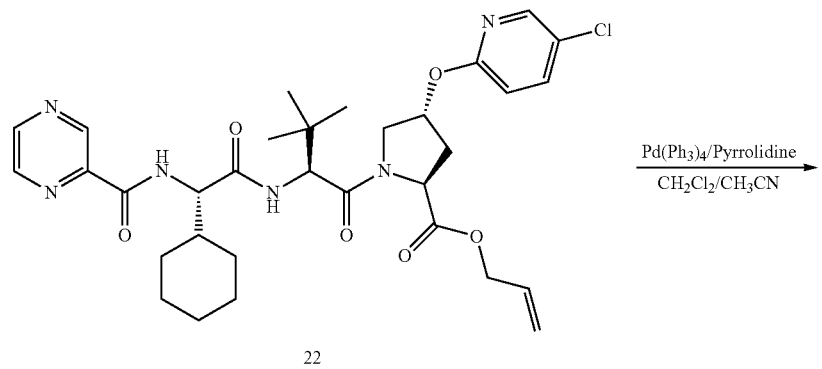
22

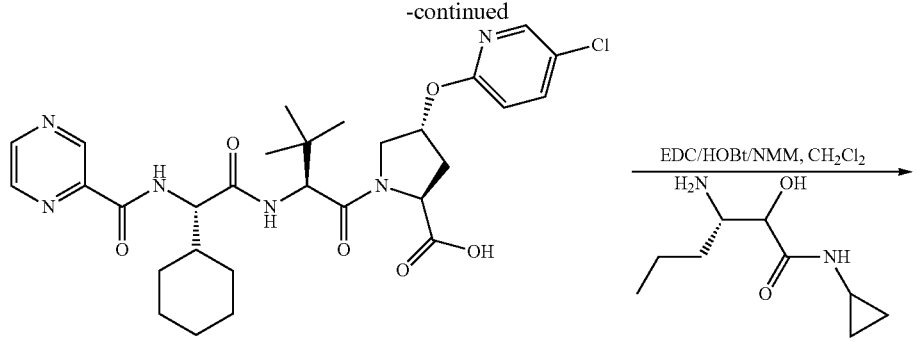

23

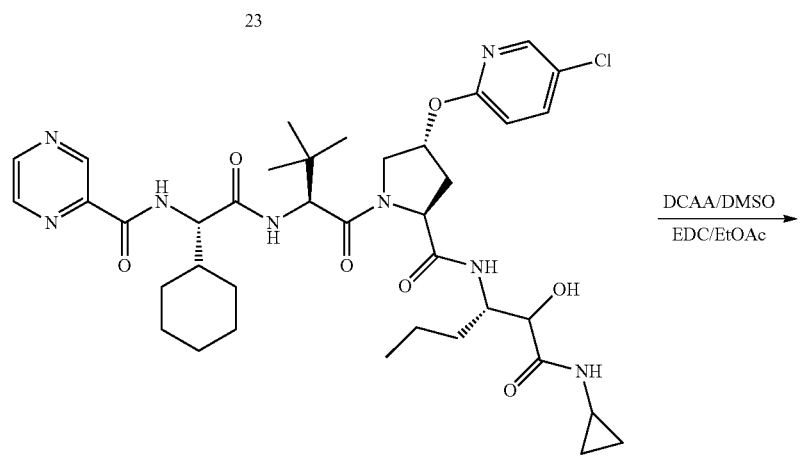

24

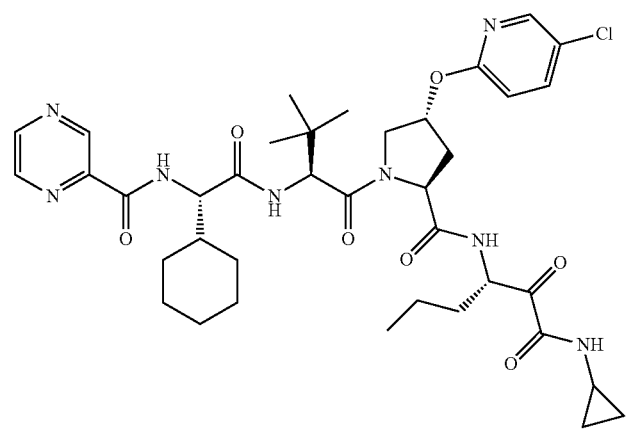

59

Scheme 5 depicts an alternative approach for preparing a compound of this invention (59). The steps used in scheme 5 could be modified by, for example, using different reagents or carrying out the reactions in a different order.

Scheme 6

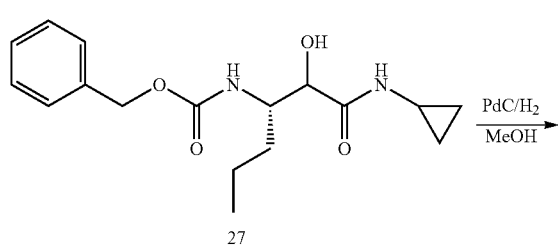

27

-continued

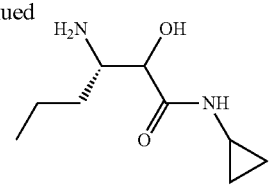

28

Scheme 6 depicts an approach for preparing compound 28. In this embodiment, a compound 27 is converted to compound 28 by removal of the benzyloxy carbonyl protecting group under hydrogenolysis conditions. This scheme 6 could be modified using techniques known to skilled practitioners to arrive at compound 28.

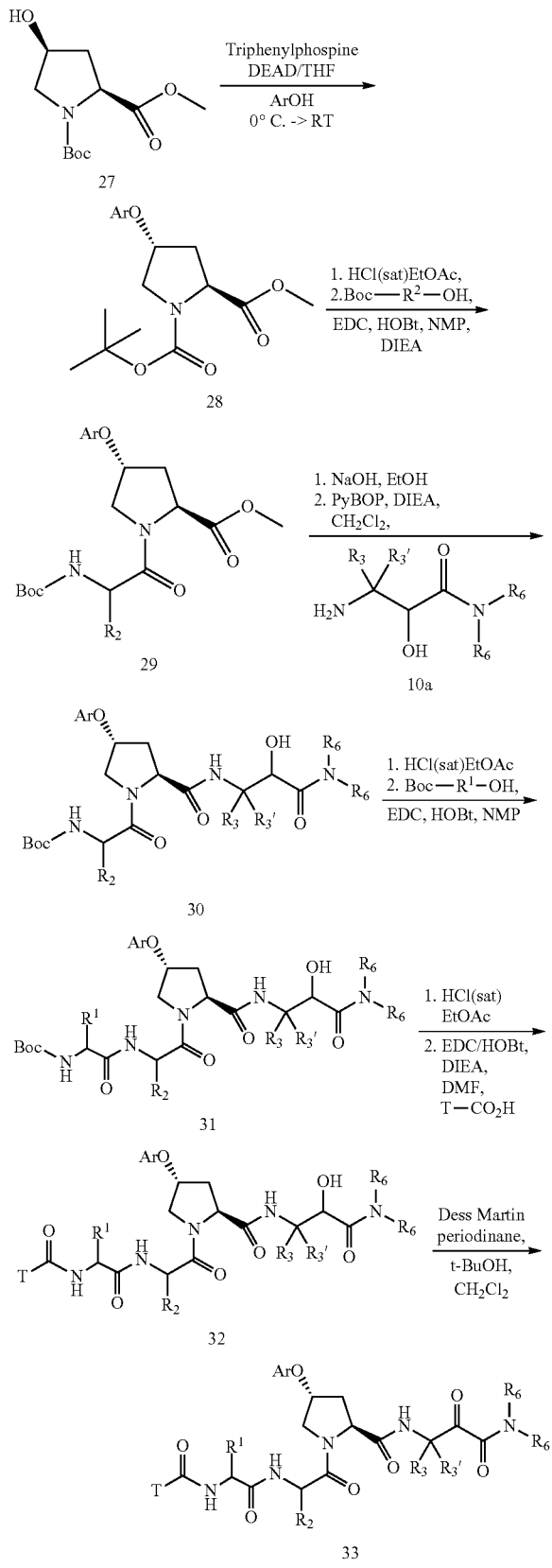

Scheme 7

Scheme 7 depicts an alternative approach to prepare compounds of this invention. In scheme 7, the variables are as described herein.

Accordingly, one embodiment of this invention provides a process for preparing a compound of formula I, as defined in any of the embodiments herein, comprising the step of: reacting a compound of formula II in the presence of a compound of formula III to provide a compound of formula IV:

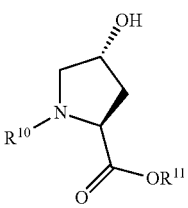

II

ArX

III

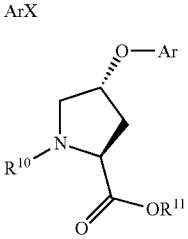

IV wherein:
$R^{10}$ is an amine protecting group, a P3-residue of an HCV protease inhibitor described herein, or a P4-P3-residue of an HCV protease inhibitor as described herein, and wherein the P3 and the P4-P3 residues are optionally protected the an amino-terminal capping group;
$R^{11}$ is a carboxy protecting group or a P1 residue of an HCV protease inhibitor described herein, wherein the P1 residue is optionally protected with a carboxy terminal protecting group or with W. Ar is as define in any of the embodiments herein. X is an appropriate leaving group. As would be appreciated by skilled practitioners, an appropriate leaving group may be generated in situ.

In an alternative embodiment, the 4-hydroxy group in formula II may be converted to a leaving group.

In such an embodiment, X is a nucleophilic oxygen which reacts with II to provide IV.

As used herein, P1, P3, P4 refer to the residues of an HCV protease inhibitor as defined in the art and as are well known to skilled practitioners.

The compound of formula IV may be carried on to a compound of formula I according to the methods described herein.

Although certain exemplary embodiments are depicted and described below, it will be appreciated that compounds of this invention can be prepared according to the methods described generally above using appropriate starting materials generally available to one of ordinary skill in the art.

Another embodiment of this invention provides a composition comprising a compound of formula I or a pharmaceutically acceptable salt thereof. According to a preferred embodiment, the compound of formula I is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound. As recognized by skilled practitioners, dosages of interferon are typically measured in IU (e.g., about 4 million IU to about 12 million IU).

When the compositions of this invention comprise a combination of a compound of formula I and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in, one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In another embodiment, the compositions of this invention additionally comprise another anti-viral agent, preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., *Antimicrobial & Antiviral Chemotherapy*, 44, p. 859 (2000) and U.S. Pat. No. 6,541,496.

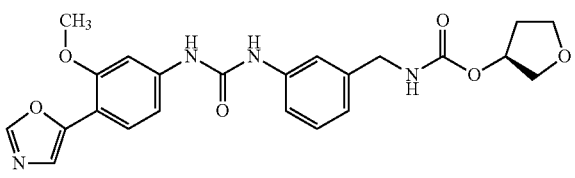

VX-497

The following definitions are used herein (with trademarks referring to products available as of this application's filing date).

"Peg-Intron" means PEG-Intron®, peginteferon alfa-2b, available from Schering Corporation, Kenilworth, N.J.;

"Intron" means Intron-A®, interferon alfa-2b available from Schering Corporation, Kenilworth, N.J.;

"ribavirin" means ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as Rebetol® from Schering Corporation, Kenilworth, N.J., or as Copegus® from Hoffmann-La Roche, Nutley, N.J.;

"Pagasys" means Pegasys®, peginterferon alfa-2a available Hoffmann-La Roche, Nutley, N.J.;

"Roferon" mean Roferon®, recombinant interferon alfa-2a available from Hoffmann-La Roche, Nutley, N.J.;

"Berefor" means Berefor®, interferon alfa 2 available from Boehringer Ingelheim Pharmaceutical, Inc., Ridgefield, Conn.;

Sumiferon®, a purified blend of natural alpha interferons such as Sumiferon available from Sumitomo, Japan;

Wellferon®, interferon alpha n1 available from Glaxo_Wellcome LTd., Great Britain;

Alferon®, a mixture of natural alpha interferons made by Interferon Sciences, and available from Purdue Frederick Co., CT;

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) Intron (interferon-alpha 2B, Schering Plough),
(b) Peg-Intron,
(c) Pegasys,
(d) Roferon,
(e) Berefor,
(f) Sumiferon,
(g) Wellferon,
(h) consensus alpha interferon available from Amgen, Inc., Newbury Park, Calif.,
(i) Alferon;
(j) Viraferon®;
(k) Infergen®.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alph 2B (Intron A, Schering Plough); Rebatron (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C (*Hepatology,* 33, pp. 433-438 (2001); consensus interferon (Kao, J. H., et al., "Efficacy of Consensus Interferon in the Treatment of Chronic Hepatitis" *J. Gastroenterol. Hepatol.* 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity" *Pathol. Biol.* (Paris) 47, pp. 553-559 (1999); interleukin 2 (Davis, G. L. et al., "Future Options for the Management of Hepatitis C." *Seminars in Liver Disease,* 19, pp. 103-112 (1999); Interleukin 6 (Davis et al. "Future Options for the Management of Hepatitis C." *Seminars in Liver Disease* 19, pp. 103-112 (1999); interleukin 12 (Davis, G. L. et al., "Future Options for the Management of Hepatitis C." *Seminars in Liver Disease,* 19, pp. 103-112 (1999); Ribavirin; and compounds that enhance the development of type 1 helper T cell response (Davis et al., "Future Options for the Management of Hepatitis C." *Seminars in Liver Disease,* 19, pp. 103-112 (1999). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers" *J. Interferon Cytokine Res.,* 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" *J. Am. Acad. Dermatol.,* 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P50 monooxygenase activity are known (see U.S. Pat. No. 6,037,157 and Yun, et al. *Drug Metabolism & Disposition,* vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such antiviral agents include, but are not limited to, immunomodulatory agents, such as α-, β-, and γ-interferons, pegylated derivatized interferon-α compounds, and thymosin; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (the IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$ (min)" or "RT" refers to the HPLC retention time, in minutes, associated with the compound. The HPLC retention times listed were obtained from the mass spec. data or using the following method (Method B):
Instrument: Hewlett Packard HP-1050;
Column: YMC $C_{18}$ (Cat. No. 326289C46);
Gradient/Gradient Time: 10-90% $CH_3CN/H2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

Preparation of Compound 59

4-Hydroxy-pyrrolidine-1,2-dicarboxylic acid 1-benzyl ester 2-tert-butyl ester (3)

Commercially available (Sachem) Z-Hydroxy-proline (1) (10 g, 42.51 mmols) was dissolved 90 mls of THF (tetrahydrofuran) and was cooled to 0° C. with an ice water bath. To this was added previously prepared tert-butyl N,N'-diisopropyl-imidocarbamate (2) (27 ml, 135 mmol) via a dropping funnel over 30 minutes. After addition the cooling bath was removed and the reaction stirred at ambient temperature for 24 hours. The volume of the reaction was reduced and then diethyl ether was added prior to washing with saturated sodium bicarbonate, then 0.5M hydrochloric acid, then water, and finally with brine. The organic layer was dried with sodium sulfate and concentrated in vacuo to give 15 g of crude material. Material was run through a plug of SiO2 and eluted with 45% EtOAc-Hexanes to give 4-Hydroxy-pyrrolidine-1,2-dicarboxylic acid 1-benzyl ester 2-tert-butyl ester 3 as a colorless oil 11.0 g (81%)

$^1$H NMR ($CDCl_3$, ppm) δ 7.35 (m, 5H), 5.2 (m, 2H), 4.3 (m, 2H), 4.65 (m, 3H), 2.35 (m, 1H), 2.1 (t, 1H), 1.35, 1.55 (rotomers, 1.45, 9H).

1-(2-{2-Cyclohexyl-2-[(pyrazine-2-carbonyl)-amino]-acetylamino}-3,3-dimethyl-butyryl)-4-hydroxy-pyrrolidine-2-carboxylic acid tert-butyl ester (6)

Mixed (3) in EtOH, and added catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as a yellow solid, which was carried on into the next step. Z-Tbg-OH (8.3 g, 31.1 mmols) was dissolved in NMP and to it was added EDC (6.0 g, 31.1 mmols), HOBT (4.2 g, 31.1 mmols), DMAP (340 mgs, 2.8 mmols), and cooled to 0° C. using and ice-water bath. To this mixture was added the amine as a solution in NMP, and the reaction was stirred for 2 days. The reaction was poured over ice and acidified with 0.5N hydrochloric acid to pH 5, and then extracted with EtOAc. The organic extracts were washed with saturated sodium bicarbonate, then water, and finally with brine. The organic layer was dried with sodium sulfate and concentrated in vacuo to give 14.8 g of crude material. Purification was carried out using chromatography on SiO2, eluting with 50% EtOAc—Hexanes. Concentration of the homogeneous fractions yielded 10.5 grams of 4 as a colorless foam (85%) and used as is in the next step.

To a mixture of 4 (10.5 g, 24.16 mmol) in EtOH, was added a catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as a yellow solid, which was carried on into the next step. Z-Chg-OH (7.7 g, 26.6 mmols) was dissolved in NMP and to it was added EDC (5.1 g, 26.7 mmols), HOBT (3.6 g, 26.6 mmols), and cooled to 0° C. using and ice-water bath. To this mixture was added the previously prepared amine as a solution in NMP, and the reaction was stirred for 2 days. The reaction was poured over ice and brine, and then extracted with EtOAc. The organic extracts were washed with 0.5N hydrochloric acid, saturated sodium bicarbonate, water, and finally with brine. The organic extract was dried with sodium sulfate and concentrated in vacuo to give 15.31 g of 5 as crude material, which was used as is in the next step.

To a solution of 5 (5.6 g, 9.76 mmol) in EtOH, was added a catalytic amount of 10% Pd on carbon, then stirred under 1 atmosphere of hydrogen using a balloon. After 12 hours the reaction was shown to be complete by tlc, and the catalyst was filtered and washed with EtOH. The filtrate was concentrated and dried under high vacuum to give the amine as an amorphous solid, which was carried on into the next step. Pyrazine-2-carboxylic acid (1.45 g, 11.7 mmols) was dissolved in NMP and to it was added EDC (2.24 g, 11.7 mmols), HOBT (1.34 g, 11.7 mmols), and cooled to 0° C. using and ice bath. To this mixture was added the previously prepared amine as a solution in NMP, and the reaction was stirred for 2 days. The reaction was poured over ice and brine, and then extracted with EtOAc. The organic extracts were washed with 0.5N hydrochloric acid, saturated sodium bicarbonate, water, and finally with brine. The organic extract was dried with sodium sulfate and concentrated in vacuo to give 5.3 g (99%) of 6 as a colorless foam, which was used as is in the next step.

Pyrazine-2-carboxylic acid ({1-[4-(5-chloro-pyridin-2-yloxy)-2-(1-cyclopropylaminooxalyl-butylcarbamoyl)-pyrrolidine-1-carbonyl]-2,2-dimethyl-propylcarbamoyl}-cyclohexyl-methyl)-amide (59)

To a solution of 6 (0.15 g, 0.28 mmols) in anhydrous THF was added triphenylphosphine (0.131 g, 0.5 mmols), 2-hydroxy-4-chloro-pyridine (65 mgs, 0.5 mmols), and last was added the diethyl azodicarboxylate (0.100 mL, 1.85 mmols). The reaction was stirred at room temperature for 18 hours or until the reaction showed no 6 remaining by HPLC. THF was removed from the reaction and then the material was taken up in EtOAc, and washed with 0.1N NaOH, 0.5N hydrochloric acid, water, and finally with brine. The organic extract was dried with sodium sulfate and concentrated in vacuo to give the crude tert-butyl ester. The tert-butyl ester group was hydrolyzed to the carboxylic acid by treatment with 50% trifluoroacetic acid in dichloromethane for 3 hours. The solvent was removed under vacuum, and then the residue was taken up with 0.1N NaOH, and washed with EtOAc. The aqueous phase was acidified with 5% citric acid, and then extracted with EtOAc. The resultant organic phase was washed with water and then brine, and then the organic extract was dried with sodium sulfate and concentrated in vacuo to give 4-(5-Chloro-pyridin-2-yloxy)-1-(2-{2-cyclohexyl-2-[(pyrazine-2-carbonyl)-amino]-acetylamino}-3,3-dimethyl-butyryl)-pyrrolidine-2-carboxylic acid 7a as a colorless foam, which was used as is in the next step. To a solution of 7a in 2 mls of dimethylformamide was added TBTU (0.15 g, 0.47 mmols), DIEA (0.15 mL, 1.1 mmols), and the reaction was stirred for 1.5 hours, and then the amine 10 [U. Schoellkogf et al., *Justus Liebigs Ann. Chem. GE, pp.* 183-202 (1976) and J. Semple et al., *Org. Letts.*, 2, pp. 2769-2772 (2000) was added to the mixture followed by 4-methylmorpholine (0.2 mL, 1.82 mmol). The reaction was stirred at ambient temperature for 12 hours, and then was poured over water and extracted EtOAc. The organic extract was dried with sodium sulfate and concentrated in vacuo to give pyrazine-2-carboxylic acid [(1-{4-(5-chloro-pyridin-2-yloxy)-2-[1-(cyclopropylcarbamoyl-hydroxy-methyl)-butylcarbamoyl]-pyrrolidine-1-carbonyl}-2,2-dimethyl-propylcarbamoyl)-cyclohexyl-methyl]-amide 11a (40 mgs) as a colorless foam, which was used as is in the next step. To a solution of 11a (40 mg) in dichloromethane (4 ml) was added tert-butanol 0.1 mL, and Dess-Martin periodinane (40 mgs, 0.086 mmol), and then stirred at ambient temperature for 6 hours. To the reaction was added 1 mL of a 1:1 mixture of 1N sodium thiosulfate and saturated sodium bicarbonate. After 15 minutes the reaction was extracted with EtOAc and then the solvent was removed under vacuum. Purification was carried out using chromatography on SiO2, eluting with 50% EtOAc—Hexanes. Concentration of the homogeneous fractions yielded 0.095 grams of 59 as a colorless foam (4.5% based on 0.28 mmols of 6). $^1$H NMR (CDCl$_3$, ppm) δ 9.39 (s, 1H), 8.76 (s, 1H), 8.56 (s, 1H), 8.24 (d, 1H, J=9.6 Hz), 8.08 (s, 1H), 7.8 (d, 1H, 6.4 Hz), 7.69 (s, 1H), 7.47-7.40 (m, 2H), 7.47 (d, 1H, J=8.75 Hz), 5.63 (s, 1H), 5.60-5.50 (m, 1H), 4.90 (m, 1H), 4.70 (m, 1H), 4.11 (d, 1H, J=11.6 Hz), 4.0 (m, 1H), 2.90 (m, 1H) 2.60 (m, 1H), 2.25 (m, 1H), 2.0 (m, 1.90-1.4 (m, 1H), 1.25-0.8 (m, 18H), (0.73 (m, 2H); LC/MS: RT=3.61 min, 4.15 min (10-90% CH3CN/7 min); MH+=767.3, M-=765.5.

Example 2

Alternative Preparation of Compound 59

Boc-Pro(4(R)-5-Chloro-pyridin-2-yloxy)-OH (15a)

Boc-Hyp-OH (130 g, 562.16 mmol) was dissolved in anhydrous DMSO (1.6 L) and to this solution was added 1M potassium tert-butoxide in THF (1.4 L, 140 mmol) maintaining the internal temperature under 25° C. After stirring the solution for 1.5 h at RT, 2,5-Dichloro-pyridine (90.0 g, 608.15 mmol) was added and the reaction mixture was stirred for 18 h at RT. The mixture was poured into water (2.5 L) and extracted with Ethyl Ether (1 L) to remove excess 2,5-Dichloro-pyridine. The aqueous layer was then acidified with 1N HCL (0.8 L) and extracted two times with Ethyl Acetate (2.5 L). The organic layers were combined and washed with Brine. The Ethyl Acetate was dried with magnesium sulfate, filtered and concentrated under reduced pressure to give a brown oil ~210 g crude material.

Boc-Pro (4(R)-5-Chloro-pyridin-2-yloxy)-allyl ester (16)

Boc-Pro (4(R)-5-Chloro-pyridin-2-yloxy)-OH (15a) (~210 g, 557 mmol) was dissolved in anhydrous acetonitrile (1.5 L) 2,3,4,6,7,8,9,10-Octahydro-pyrimido[1,2-a]azepine (DBU) (0.13 L, 869.28 mmol) and allyl bromide (81.5 g, 673.66 mmol) were added successively and the reaction mixture was stirred for 18 h at RT. The mixture was concentrated, the resulting oil was diluted with Ethyl Acetate (2 L) and washed successively with water two times 500 mL and Brine 500 mL. The Ethyl Acetate layer was dried with magnesium sulfate, filtered and concentrated under reduced pressure to give a brown oil which was applied to a silica column with methylene chloride and eluted with 25% ethyl acetate in hexane to yield a yellow oil, 181 g, 472.77 mmol, 84% for two steps.

Pro (4(R)-5-Chloro-pyridin-2-yloxy)-allyl ester (17)

Boc-Pro (4(R)-5-Chloro-pyridin-2-yloxy)-allyl ester (16) (181 g, 427.77 mmol) was treated with cold 0° C. (440 mL) 90:10 Trifluoroacetic acid, Methylene Chloride. The mixture was allowed to come to RT and stirred for 3 h. After 3 h 400 mL Toluene was added to the mixture and it was concentrated under reduced pressure to yield the crude Trifluoroacetic acid salt of (17).

Boc-Tbg-Pro (4(R)-5-Chloro-pyridin-2-yloxy)-allyl ester (18)

Pro (4(R)-5-Chloro-pyridin-2-yloxy)-allyl ester (17) (187 g, theor.), the crude trifluoroacetic acid salt was coupled to a cooled 0° C. solution of Boc-Tbg-OH (110 g, 475.56 mmols), NMM (155 mL, 1.410 mmol), EDC (99 g, 518.32 mmols), HOBt (70 g, 518.32 mmols) in 400 mL Methylene Chloride. The mixture was allowed to come to RT and stirred for 18 h. The mixture was concentrated, the resulting oil was diluted with Ethyl Acetate (2 L) and washed successively with 0.5N HCL two times 500 mL, and water 500 mL, Brine 500 mL. The Ethyl Acetate layer was dried with magnesium sulfate, filtered and concentrated under reduced pressure to give a brown oil which was applied to a silica column with methylene chloride and eluted with 15% ethyl acetate in hexane to yield a pale yellow foam, 180 g, 362.83 mmol, 77%.

Tbg-Pro (4(R)-5-Chloro-pyridin-2-yloxy)-allyl ester (19)

Boc-Tbg-Pro (4(R)-5-Chloro-pyridin-2-yloxy)-allyl ester (18) (180 g, 362.83 mmol), was treated with cold 0° C. (330 mL) 90:10 Trifluoroacetic acid, Methylene Chloride. The mixture was allowed to come to RT and stirred for 3 h. After 3 h Toluene (200 mL) was added to the mixture and it was concentrated under reduced pressure to yield a yellow oil to which methylene chloride (100 mL), ethyl ether (1.5 L) were added successively. The mixture was stirred and 4N HCL dioxane was added (50 mL) stirring was continued for 1 h and the crude HCL dipeptide salt was filtered and washed with cold ethyl ether 0° C. to yield 142.5 g, 323.86 mmol 91%.

Boc-Chg-Tbg-Pro (4(R)-5-Chloro-pyridin-2-yloxy)-allyl ester (20)

Tbg-Pro (4(R)-5-Chloro-pyridin-2-yloxy)-allyl ester (19) (142.5 g, 323.86 mmol) was coupled to a cooled 0° C. solution of Boc-Chg-OH (94 g, 365.29 mmol), NMM (109 mL, 994.18 mmol), EDC (69 g, 361.26 mmol), HOBt (48.77 g, 361.26 mmol) in 400 mL Methylene Chloride. The mixture was allowed to come to RT and stirred for 18 h. The mixture was concentrated, the resulting oil was diluted with Ethyl Acetate (2 L) and washed successively with 0.5N HCL two times 500 mL, and water 500 mL, Brine 500 mL. The Ethyl Acetate layer was dried with magnesium sulfate, filtered and concentrated under reduced pressure to give a brown oil which was applied to a silica column with methylene chloride and eluted with 25% ethyl acetate in hexane to yield a pale yellow foam, 180 g, 362.83 mmol, 77%.

Chg-Tbg-Pro (4(R)-5-Chloro-pyridin-2-yloxy)-allyl ester (21)

Boc-Chg-Tbg-Pro (4(R)-5-Chloro-pyridin-2-yloxy)-allyl ester (20) (65 g, 102.33 mmol) was treated with cold 0° C. (250 mL) 90:10 Trifluoroacetic acid, Methylene Chloride. The mixture was allowed to come to RT and stirred for 3 h. After 3 h Toluene (200 mL) was added to the mixture and it was concentrated under reduced pressure to yield a yellow oil to which methylene chloride (200 mL) was added the mixture was stirred and, ethyl ether (1.5 L) were added successively and the crude TFA tripeptide salt was filtered and washed with cold ethyl ether 0° C. to yield 66 g, 101.53 mmol 98%.

Pyrazine-2-carbonyl-Chg-Tbg-Pro (4(R)-5-Chloro-pyridin-2-yloxy)-allyl ester (22)

Chg-Tbg-Pro (4(R)-5-Chloro-pyridin-2-yloxy)-allyl ester (21) (66 g, 101.53 mmol), the crude TFA salt was coupled to a cooled 0° C. solution of Pyrazine-2-carboxylic acid (13.6 g, 109.69 mmol), NMM (44 mL, 400.19 mmol), EDC (21 g, 109.95 mmol), HOBt (14.85 g, 109.95 mmol) in 500 mL Methylene Chloride. The mixture was allowed to come to RT and stirred for 18 h. The mixture was concentrated, the resulting oil was diluted with Ethyl Acetate (2 L) and washed successively with 0.5N HCL two times 500 mL, and water 500 mL, Brine 500 mL. The Ethyl Acetate layer was dried with magnesium sulfate, filtered and concentrated under reduced pressure to give a brown oil which was applied to a silica column with methylene chloride and eluted with 45% ethyl acetate in hexane to yield a pale yellow foam, 64.66 g, 100.85 mmol, 99%.

Pyrazine-2-carbonyl-Chg-Tbg-Pro (4(R)-5-Chloro-pyridin-2-yloxy)-OH (23)

Pyrazine-2-carbonyl-Chg-Tbg-Pro (4(R)-5-Chloro-pyridin-2-yloxy)-allyl ester (22) (64.66 g, 100.85 mmol) was dissolved in an anhydrous mixture (250 mL) 50:50 Acetonitrile, Methylene Chloride. Tetrakis (triphenylphosphine)-palladium (0) catalyst (1.5 g, 1.30 mmol) was added followed by pyrrolidine (8.55 mL, 102.44 mmol). The reaction mixture was stirred at RT for 18 h. After 18 h the solvent was evaporated. The oil was dissolved in Ethyl Acetate (2 L) and extracted with 10% citric acid (250 mL) two times, Brine (250 mL). The Ethyl Acetate layer was dried with magnesium sulfate, filtered and concentrated under reduced pressure to give a pale yellow solid 58.5 g, 97.32 mmol 96%.

3-Amino-2-hydroxy-hexanoic acid cyclopropylamide (24)

[1-(Cyclopropylcarbamoyl-hydroxy-methyl)-butyl]-carbamic acid benzyl ester (48 g, 149.82 mmol) was dissolved in Methanol (1 L) and degassed with nitrogen for five minutes, palladium, 10 wt. % on activated carbon (2.5 g) was added, hydrogen was then added for 18 h. After 18 h the hydrogen was removed and the reaction was degassed with nitrogen and filtered the resulting filtrate was evaporated and dried under high vacuum to give a white solid 26.9 g, 144.42 mmol 97%.

Pyrazine-2-carbonyl-Chg-Tbg-Pro (4(R)-5-Chloro-pyridin-2-yloxy)-Nva-hydroxy cyclopropylamide (25)

3-Amino-2-hydroxy-hexanoic acid cyclopropylamide (24) 20 g, 107.37 mmol, was coupled to Pyrazine-2-carbonyl-Chg-Tbg-Pro (4(R)-5-Chloro-pyridin-2-yloxy)-OH (23) 58.5 g, 97.32 mmol, NMM (11.76 mL, 106.96 mmol), EDC (20.45 g, 107.07 mmol), HOBt (14.45 g, 107.07 mmol) in 250 mL Methylene Chloride. The mixture was stirred for 18 h. The mixture was concentrated, the resulting oil was diluted with Ethyl Acetate (2 L) and washed successively with 0.5N HCL two times 500 mL, and water 500 mL, Brine 500 mL. The Ethyl Acetate layer was dried with magnesium sulfate, filtered and concentrated under reduced pressure to give a brown oil which was applied to a silica column with methylene chloride and eluted with 2% Methanol in Ethyl Acetate to yield a pale yellow foam, 61.5 g, 79.94 mmol, 74%.

Pyrazine-2-carboxylic acid ({1-[4-(5-chloro-pyridin-2-yloxy)-2-(1-cyclopropylaminooxalyl-butylcarbamoyl)-pyrrolidine-1-carbonyl]-2,2-dimethyl-propylcarbamoyl}-cyclohexyl-methyl)-amide (59)

To a 4 L round bottom equipped with an overhead stirrer a thermocouple and an active nitrogen inlet was added EDC (229.0 g, 151.83 mmol), followed by anhydrous Ethyl Acetate 1230 mL, Stirring was started to effect a thick slurry. To this was added Pyrazine-2-carbonyl-Chg-Tbg-Pro (4(R)-5-Chloro-pyridin-2-yloxy)-Nva-hydroxy cyclopropylamide (25). 61.5 g, 79.94 mmol, dissolved Ethyl Acetate (250 mL) then anhydrous DMSO (460 mL) was added. A cooling bath was applied to bring the internal temperature to 7° C. A cooled 7° C. solution Dichloroacetic acid (65.94 mL, 787.20 mmol) in Ethyl Acetate (100 mL) was added such that the internal temperature was maintained between 12 and 25° C. The cooling bath removed and the thin slurry was stirred for 1 h. A cooling bath was applied and the reaction was quenched with 1N HCL (1,230 mL) while maintaining the temperature between 15 and 25° C. The organic layer was separated and washed with water (200 mL) three times, brine (200 mL). The Ethyl Acetate layer was dried with magnesium sulfate, filtered and concentrated under reduced pressure to with a bath temperature of not more than 40° C. to give a brown oil which was applied to a silica column with methylene chloride and eluted with 90% Ethyl Acetate in hexane to yield a pale yellow foam, 44.0 g, 57.34 mmol, 72%. $^1$H NMR (CDCl$_3$) 9.39 1H(s), 8.76 1H(s), 8.55 1H(s), 8.22 1H(d), 8.08 1H(s), 7.47 1H(NH), 7.45 1H(d) 7.35 1H(NH), 7.01 1H(NH), 6.49 1H(d), 5.63 1H(m), 5.53 1H(m), 4.88 1H(m), 4.70 1H(d), 4.67 1H(m), 4.11 1H(m), 4.01 1H(m), 2.86 1H(m), 2.57 1H(m), 2.25 1H(m), 1.96 1H(m), 1.80 1H(m), 1.70 6H(m), 1.60 2H(m), 1.50 2H(m), 1.25 3H(m), 0.96 12H(m), 0.91 2H(m), 0.72 2H(m).

Example 3

Compounds 1-72 and 74-76 have been prepared substantially as described herein. Analytical data for these compounds were consistent with the disclosed structures of the compounds. Further selected data is provided below:

| Cmpd no. | Method | MASS+ | RT |
|---|---|---|---|
| 1 | A | 801.81 | 1.54 |
| 2 | A | 800.83 | 1.68 |
| 3 | A | 800.51 | 1.77 |
| 4 | A | 750.54 | 1.63 |
| 5 | A | 800.31 | 1.50 |
| 6 | A | 800.43 | 1.61 |
| 7 | A | 768.27 | 1.93 |
| 8 | A | 768.31 | 1.91 |
| 9 | A | 816.26 | 2.07 |
| 10 | A | 768.28 | 1.99 |
| 11 | A | 868.27 | 2.18 |
| 12 | A | 800.26 | 2.16 |
| 13 | A | 800.17 | 2.03 |
| 14 | A | 816.14 | 2.07 |
| 15 | A | 808.16 | 2.17 |
| 16 | A | 816.12 | 2.25 |
| 17 | A | 808.41 | 2.09 |
| 18 | A | 750.39 | 1.97 |
| 19 | A | 808.40 | 2.17 |
| 20 | A | 766.34 | 1.99 |
| 21 | A | 762.43 | 1.94 |
| 22 | A | 800.38 | 2.08 |
| 23 | A | 792.30 | 1.87 |
| 24 | A | 792.30 | 1.97 |
| 25 | A | 767.67 | 1.43 |
| 26 | A | 778.00 | 1.48 |
| 27 | A | (M + Na$^+$)/824.58 | 1.48 |
| 28 | A | (M + Na$^+$)/832.65 | 1.46 |
| 29 | A | (M + Na$^+$)/824.61 | 1.52 |
| 30 | A | (M + Na$^+$)/824.61 | 1.51 |
| 31 | A | (M + Na$^+$)/856.67 | 1.58 |
| 32 | A | (M + Na$^+$)/774.63 | 1.39 |
| 33 | A | (M + Na$^+$)/800.62 | 1.48 |
| 34 | B | 734.10 | 3.73 |
| 52 | B | 790.30 | 3.86 |
| 53 | B | 800.10 | 4.48 |
| 54 | B | 768.20 | 4.13 |
| 55 | B | 768.90 | 4.51 |
| 56 | B | 766.80 | 4.61 |
| 57 | B | 778.40 | 3.98 |
| 58 | B | 733.40 | 3.71 |
| 59 | B | 767.30 | 4.02 |
| 60 | B | 852.90 | 4.70 |
| 61 | B | 818.40 | 4.21 |
| 62 | B | 767.22 | 1.68 |
| 63 | B | 767.29 | 4.21 |
| 66 | B | 766.30 | 4.26 |
| 67 | B | 851.30 | 3.43 |
| 68 | B | 768.30 | 4.10 |
| 69 | B | 789.90 | 3.94 |
| 70 | B | 978.00 | 4.14 |
| 71 | B | 844.40 | 2.50 |
| 72 | B | 797.14 | 4.77 |
| 74 | A | 802.62 | 1.52 |
| 75 | B | 768.30 | 5.20 |
| 76 | B | 766.30 | 5.02 |

RT—retention time.
Method A: Hypersil BDS C18 column 5um, 2.1 × 50 mm Flow rate: 1.0 ml/min Run time: 2.39 min Solvents: 0-95% MeCN.
Method B: see above.

| No. | Structure |
|---|---|
| 1 | 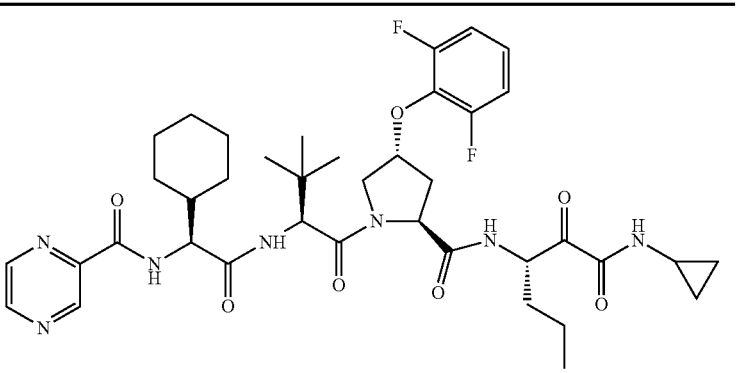 |

| No. | Structure |
|---|---|
| 2 | 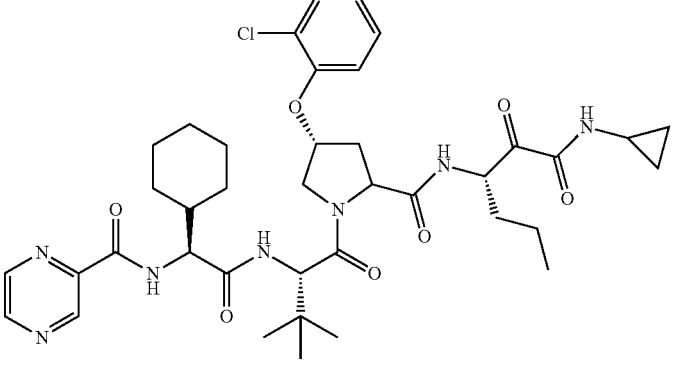 |
| 3 | 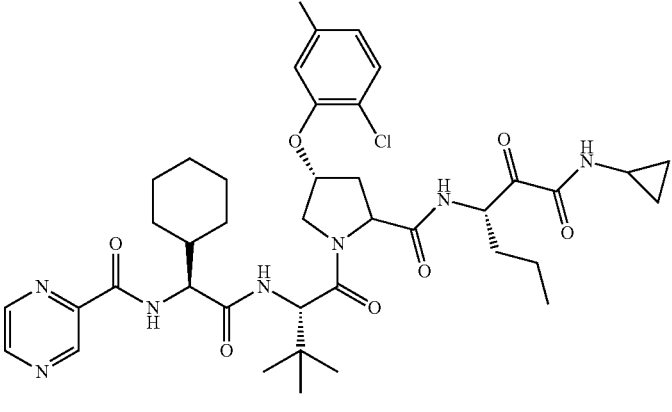 |
| 4 | 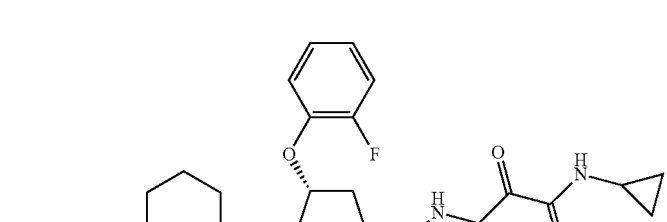 |

-continued

| No. | Structure |
|---|---|
| 5 | 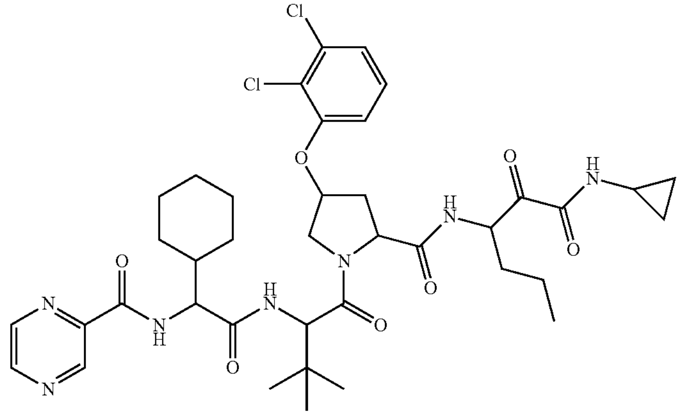 |
| 6 | 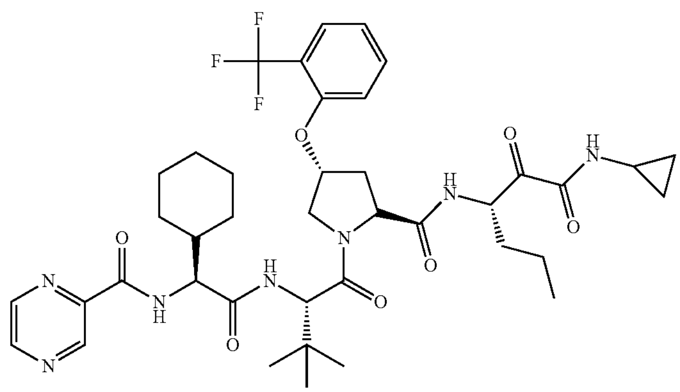 |
| 7 | 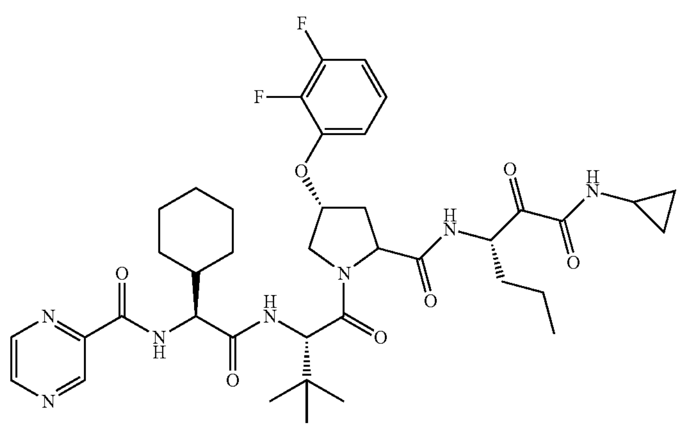 |
| 8 | 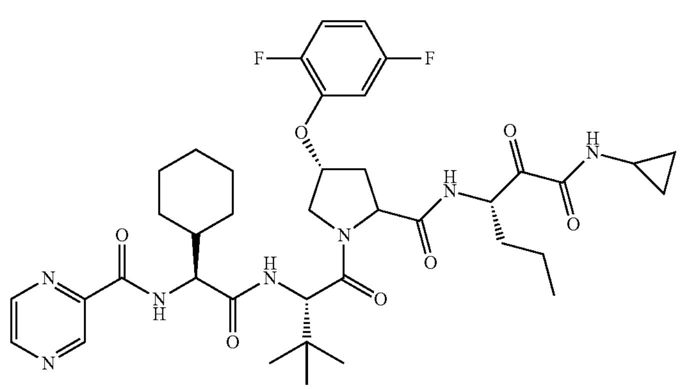 |

| No. | Structure |
|---|---|
| 9 | 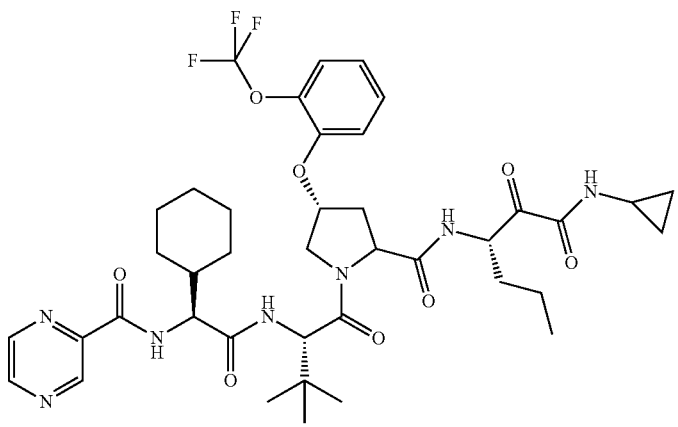 |
| 10 | 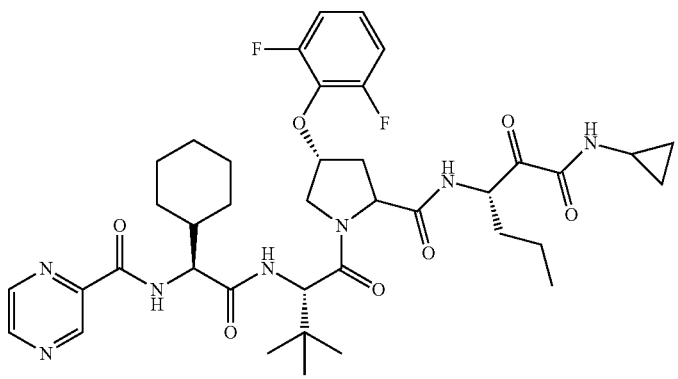 |
| 11 | 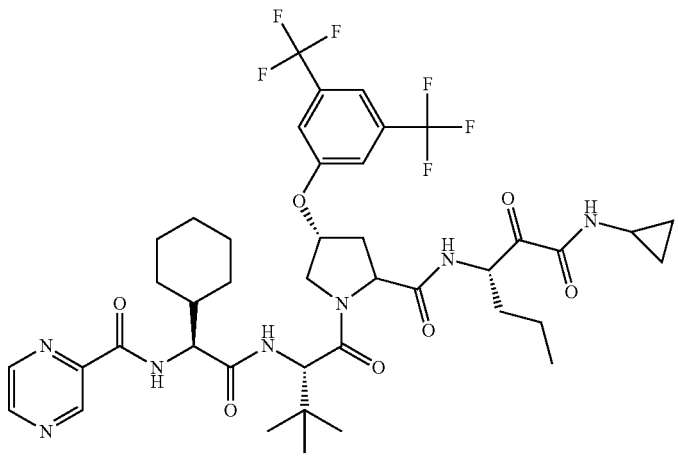 |

-continued

| No. | Structure |
|---|---|
| 12 | 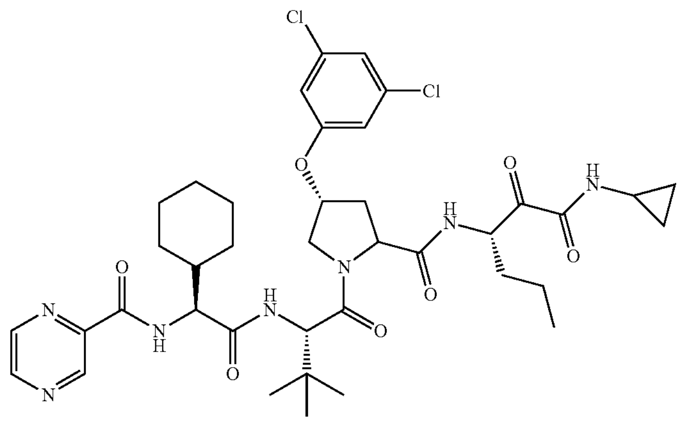 |
| 13 | 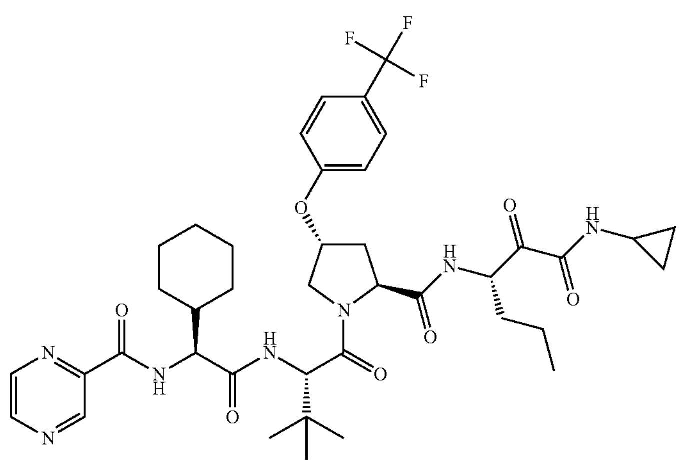 |
| 14 | 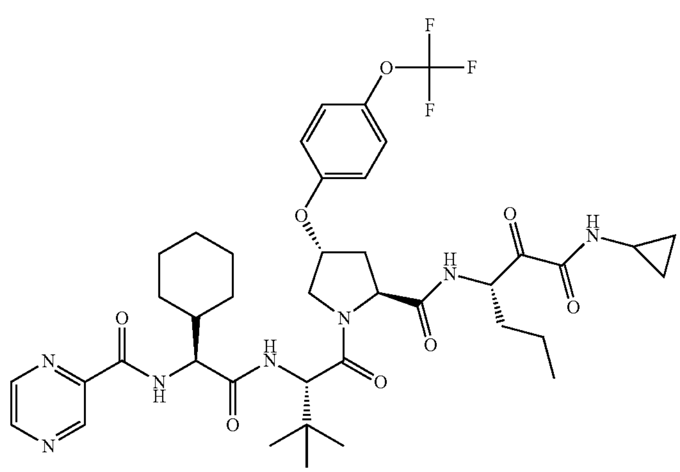 |

-continued
| No. | Structure |
|---|---|
| 15 | 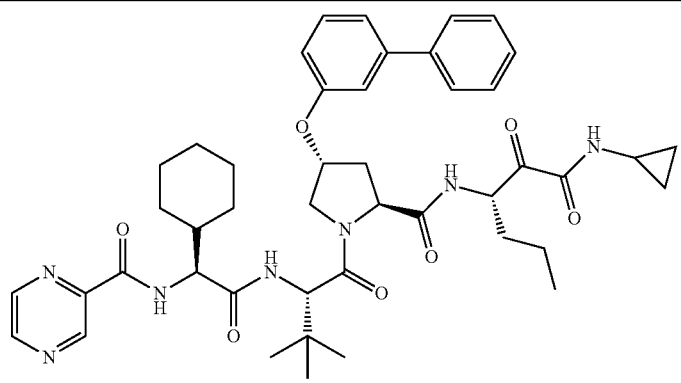 |
| 16 | 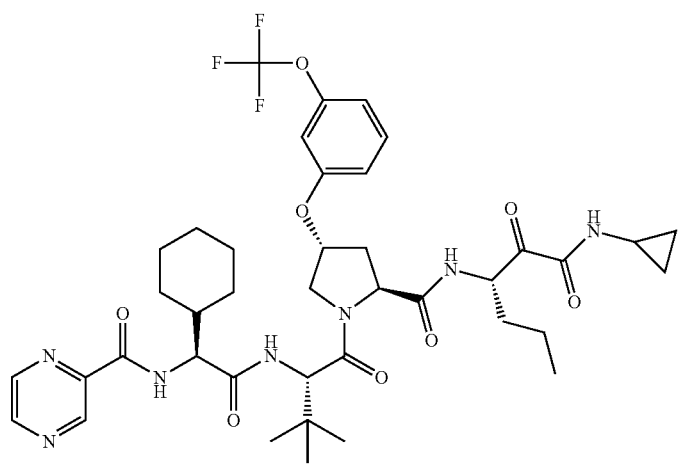 |
| 17 | 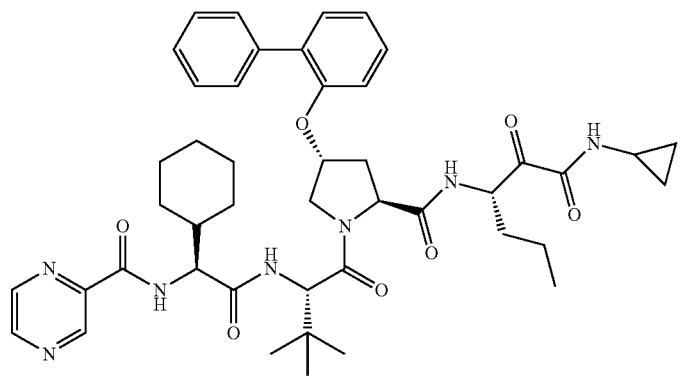 |
| 18 | 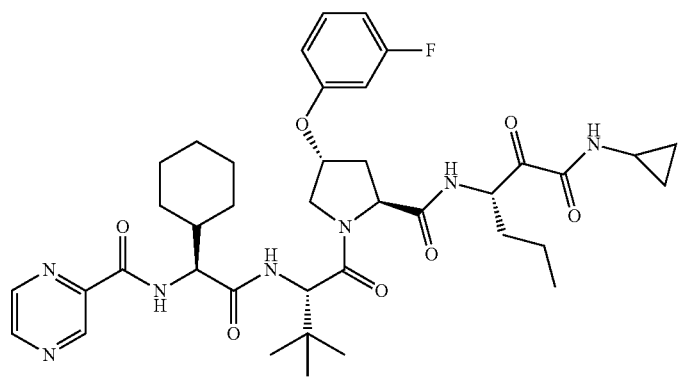 |

| No. | Structure |
|---|---|
| 19 | 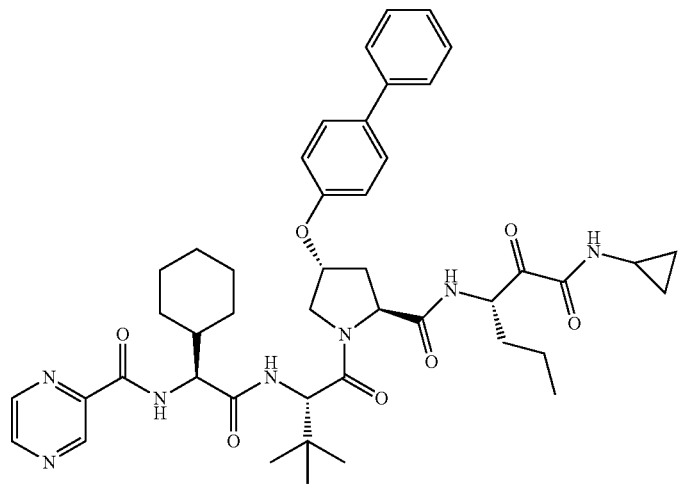 |
| 20 | 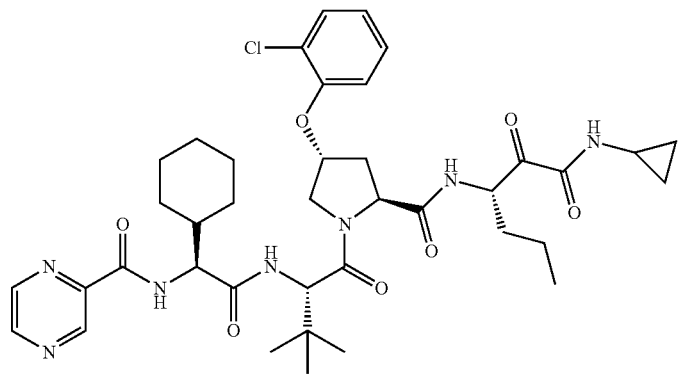 |
| 21 | 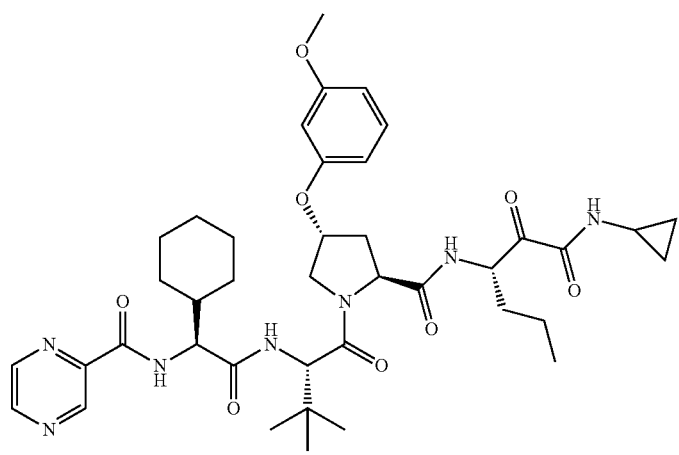 |

-continued
| No. | Structure |
|---|---|
| 22 | 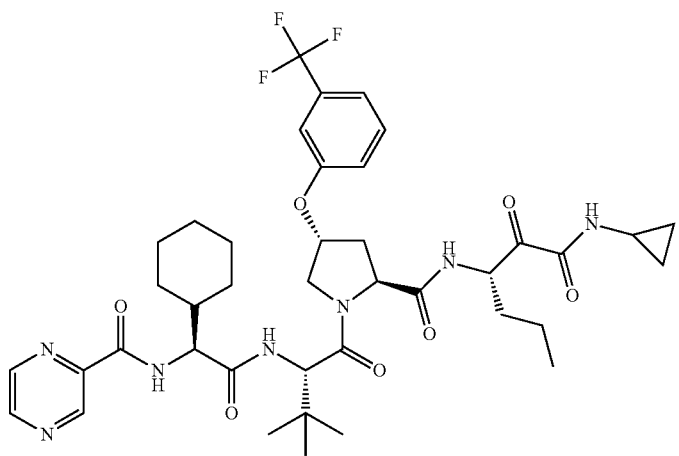 |
| 23 | 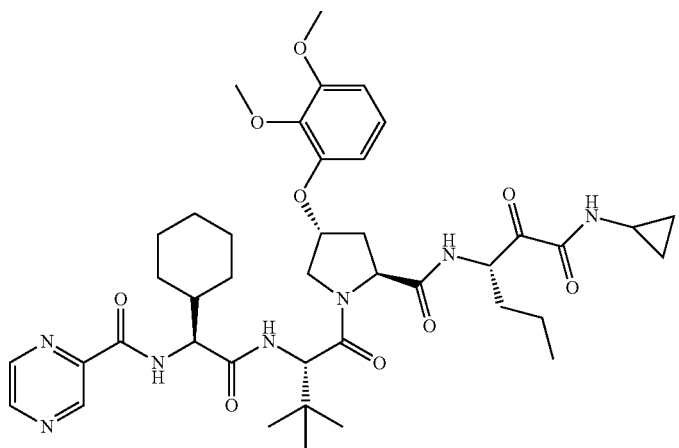 |
| 24 | 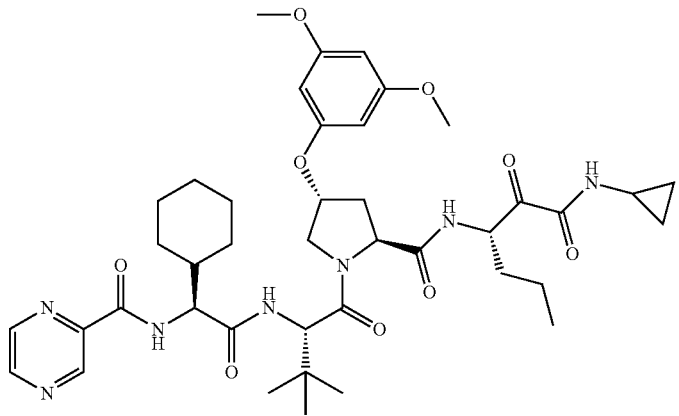 |

| No. | Structure |
|---|---|
| 25 | 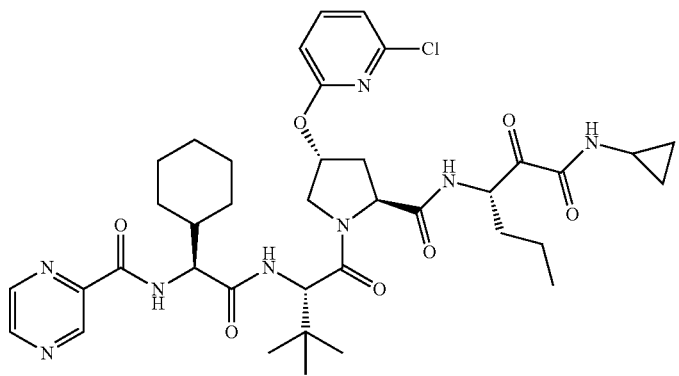 |
| 26 | 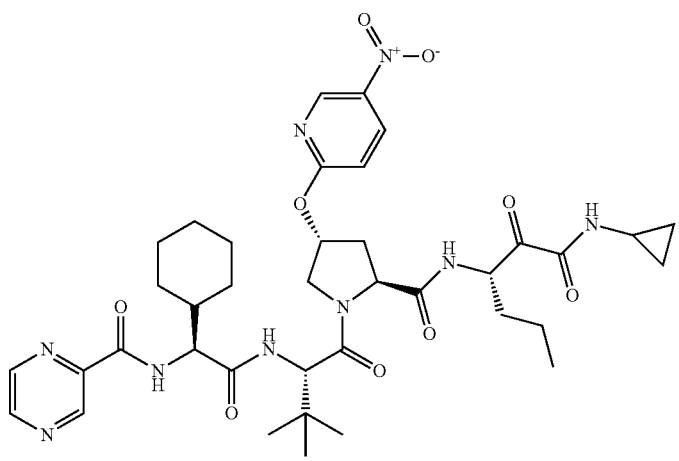 |
| 27 | 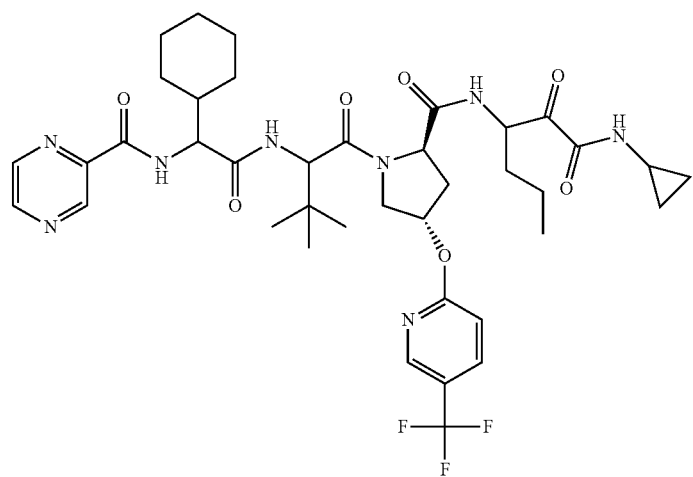 |

| No. | Structure |
|---|---|
| 28 | 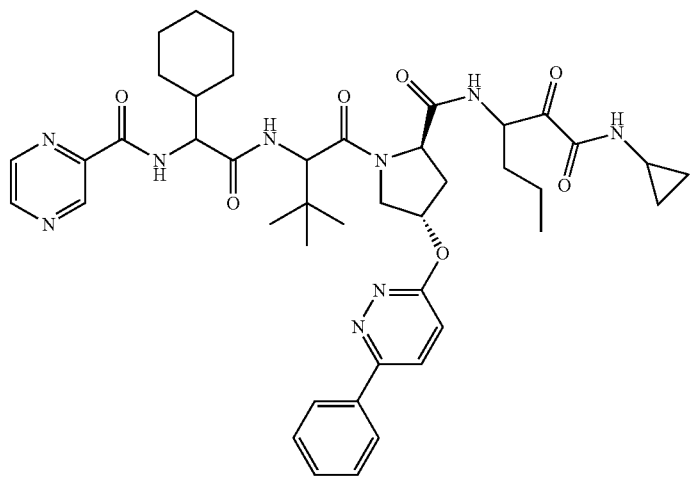 |
| 29 | 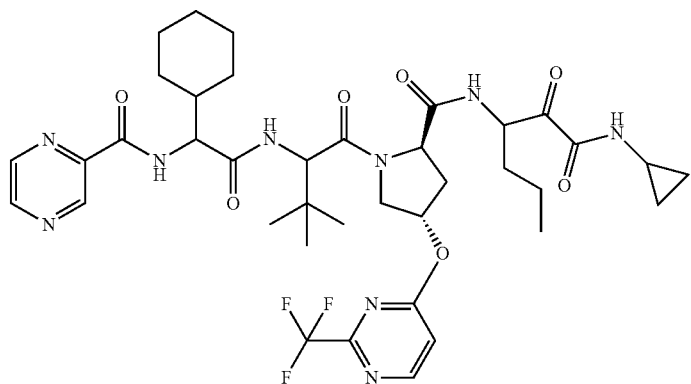 |
| 30 | 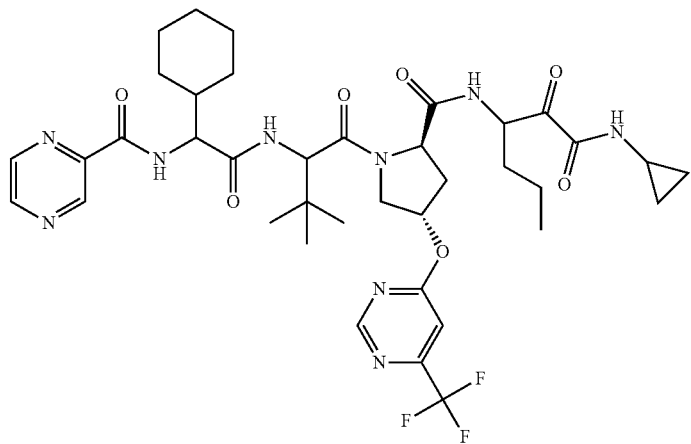 |

-continued
| No. | Structure |
|---|---|
| 31 | 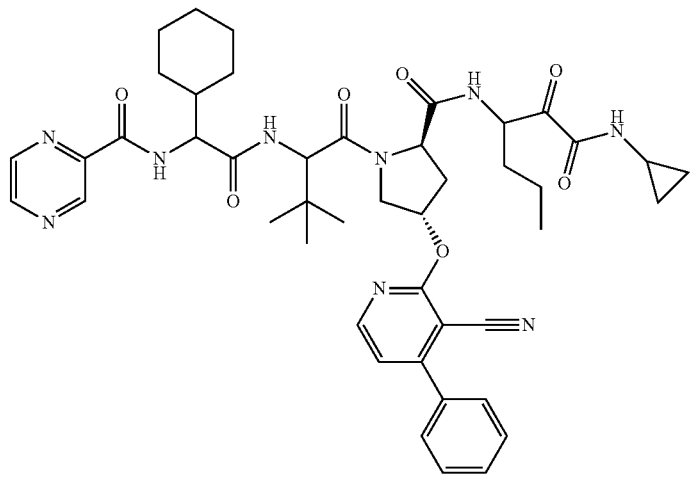 |
| 32 | 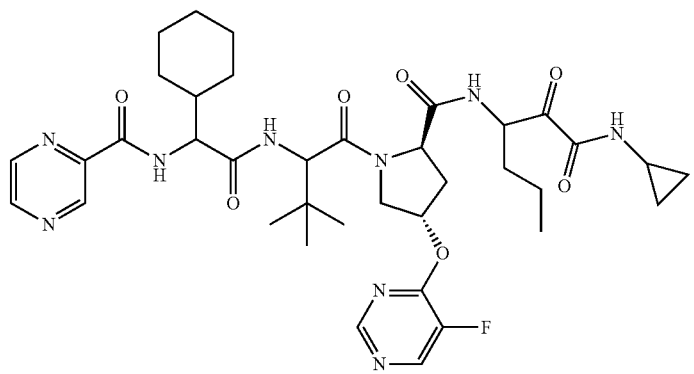 |
| 33 | 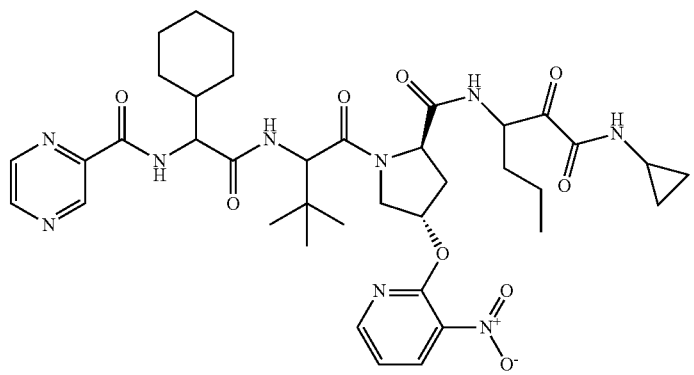 |

| No. | Structure |
|---|---|
| 34 | 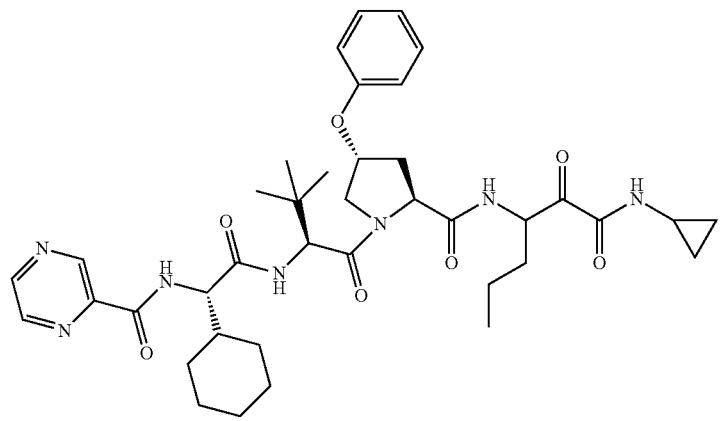 |
| 35 | 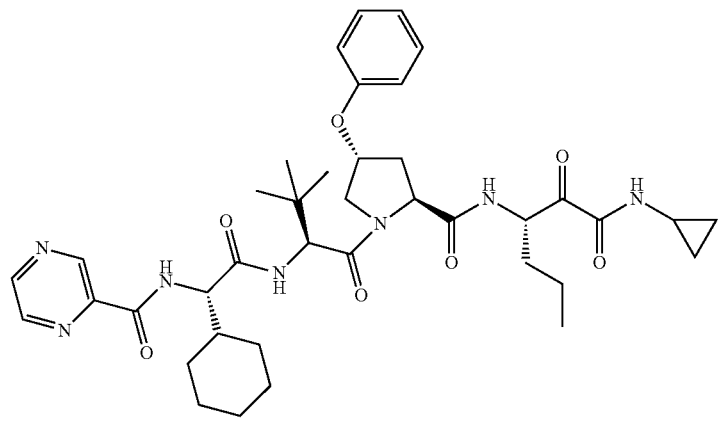 |
| 36 | 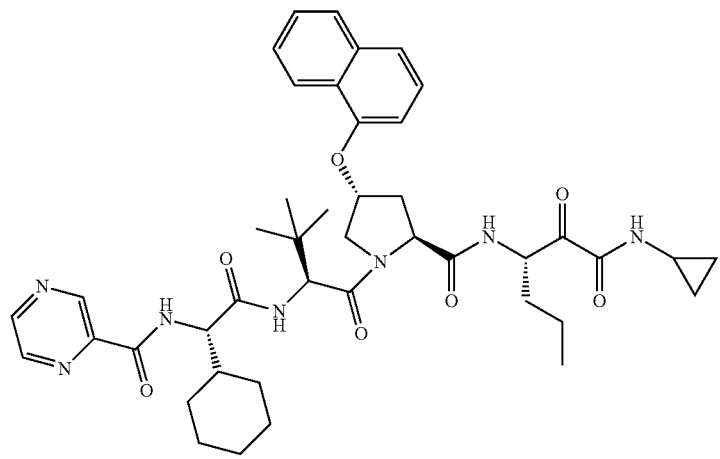 |

| No. | Structure |
|---|---|
| 37 | 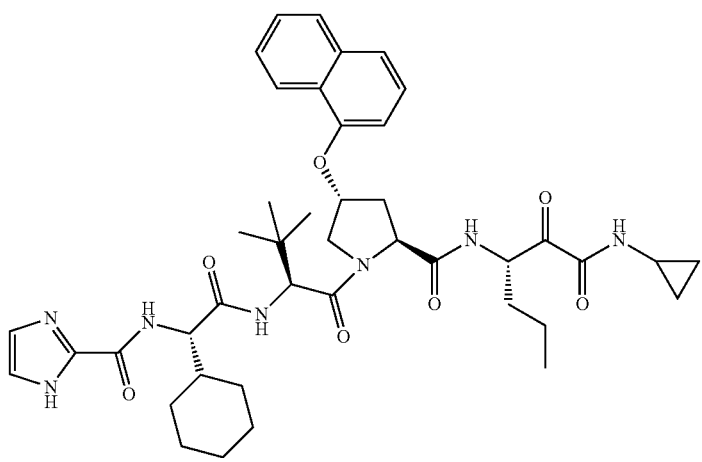 |
| 38 | 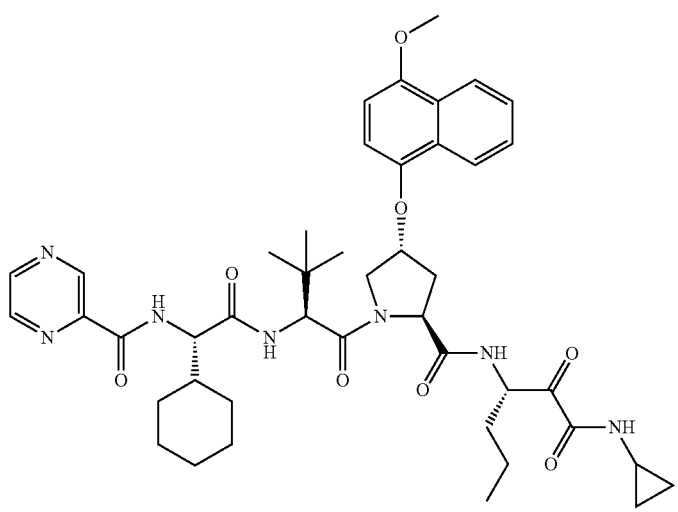 |
| 39 | 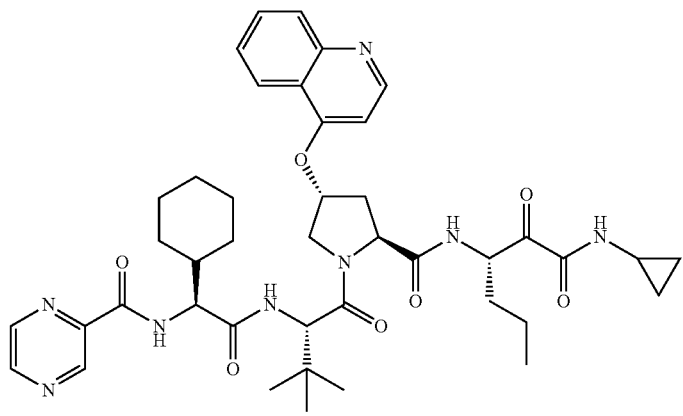 |

| No. | Structure |
|---|---|
| 40 | 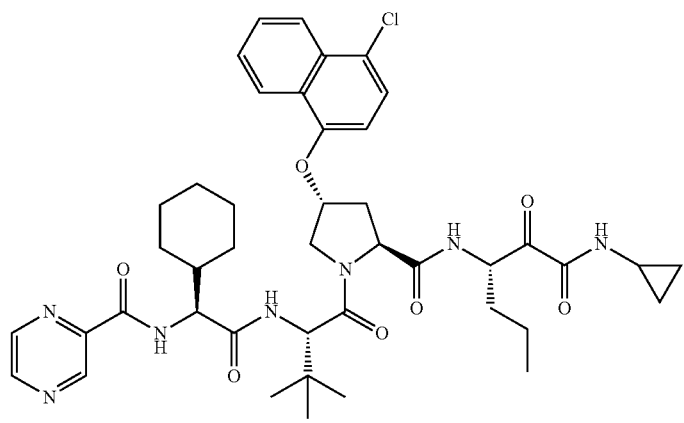 |
| 41 | 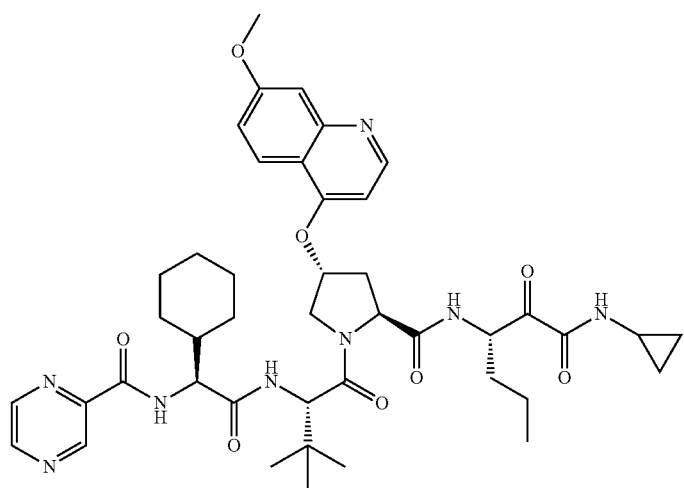 |
| 42 | 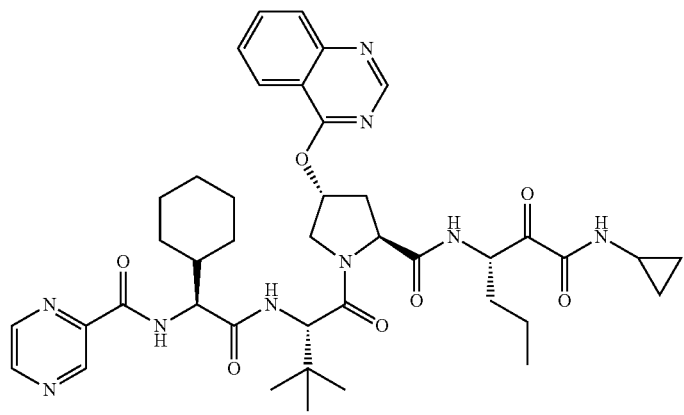 |

-continued
| No. | Structure |
|---|---|
| 43 | 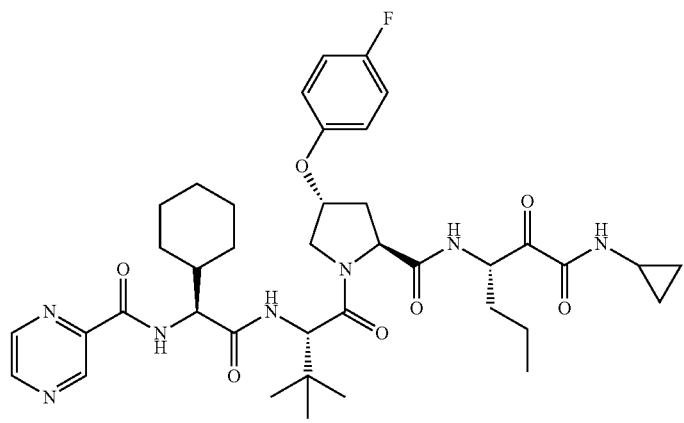 |
| 44 | 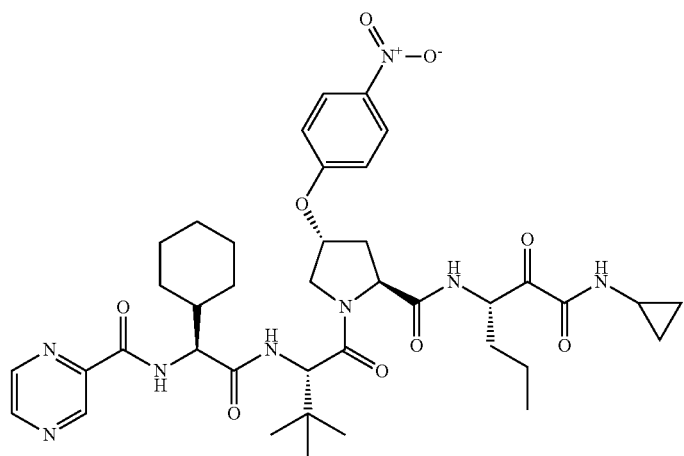 |
| 45 | 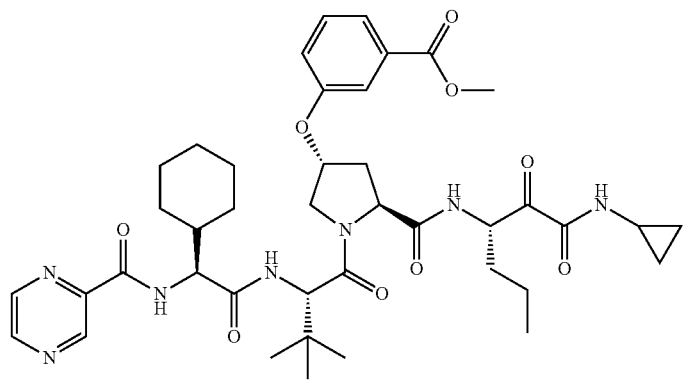 |

| No. | Structure |
|---|---|
| 46 | 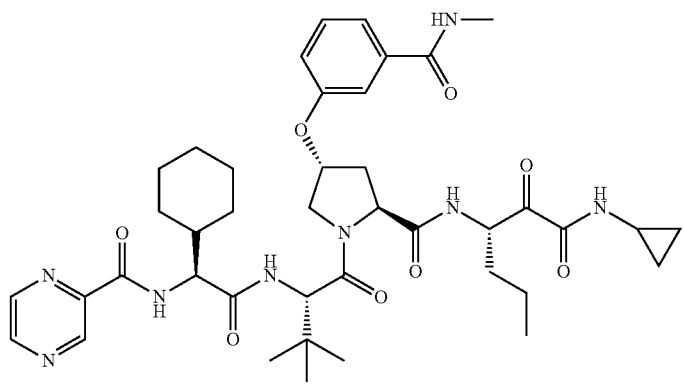 |
| 47 | 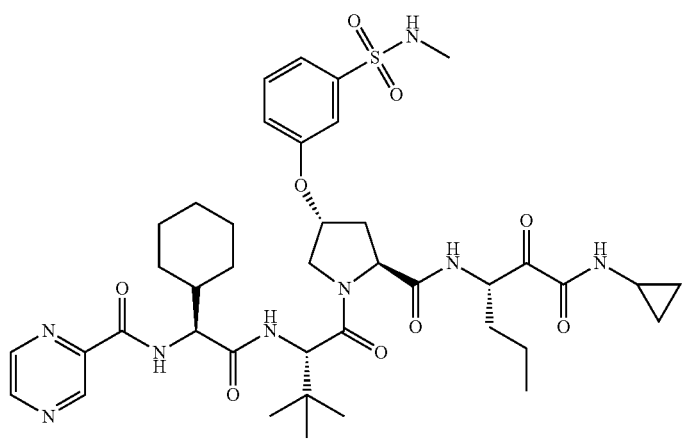 |
| 48 | 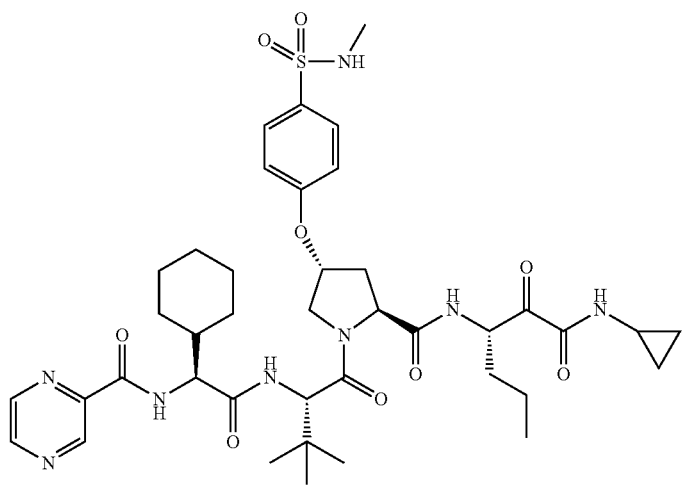 |

| No. | Structure |
|---|---|
| 49 | 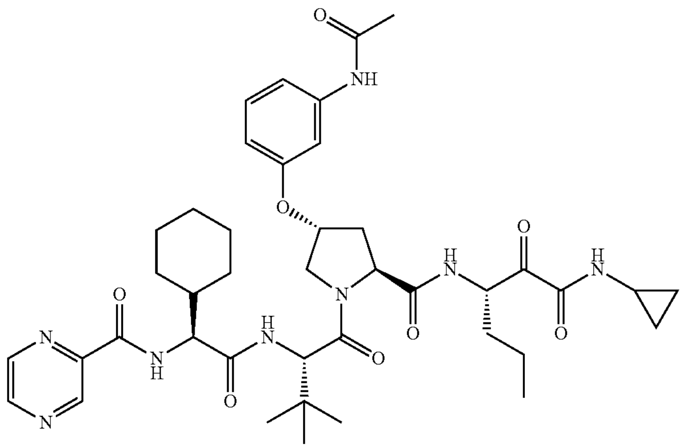 |
| 50 | 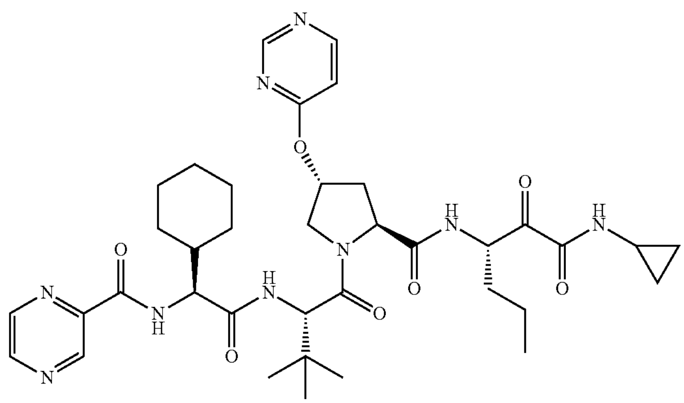 |
| 51 | 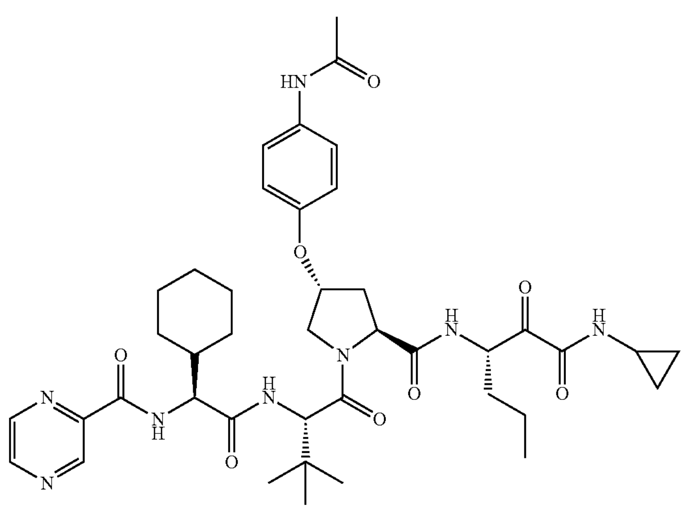 |

| No. | Structure |
|---|---|
| 52 | 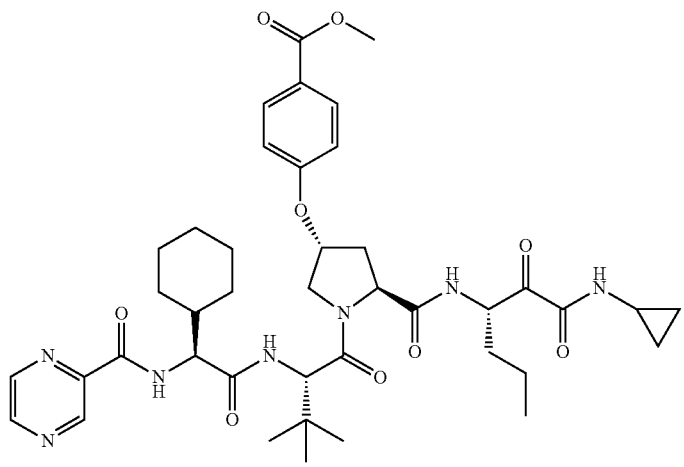 |
| 53 | 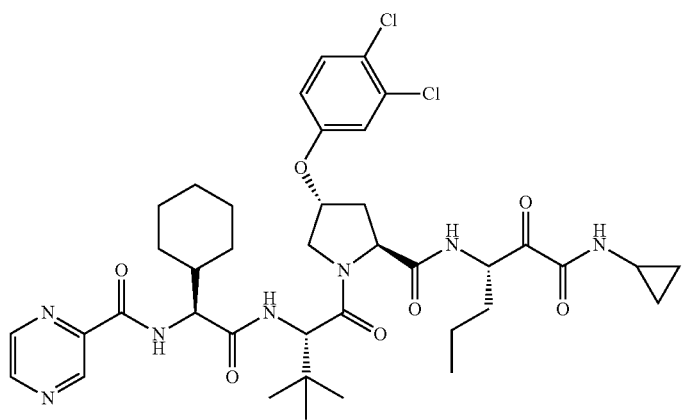 |
| 54 | 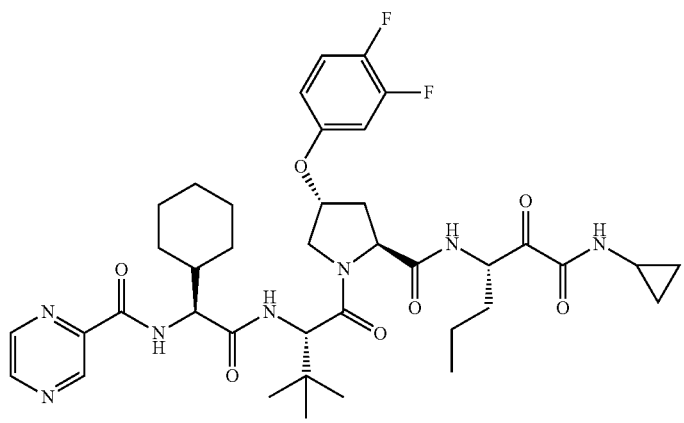 |

| No. | Structure |
|---|---|
| 55 | 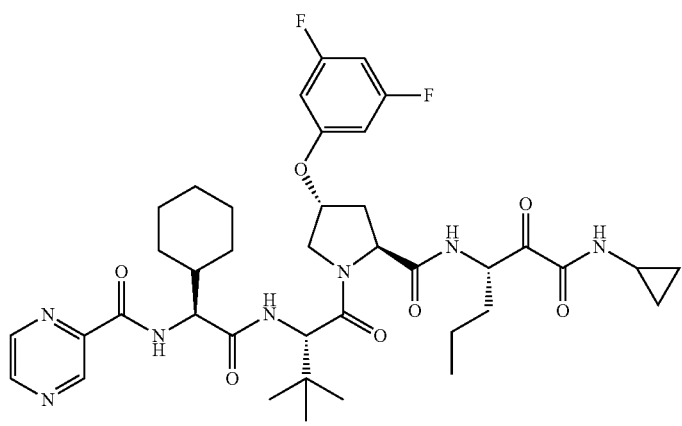 |
| 56 | 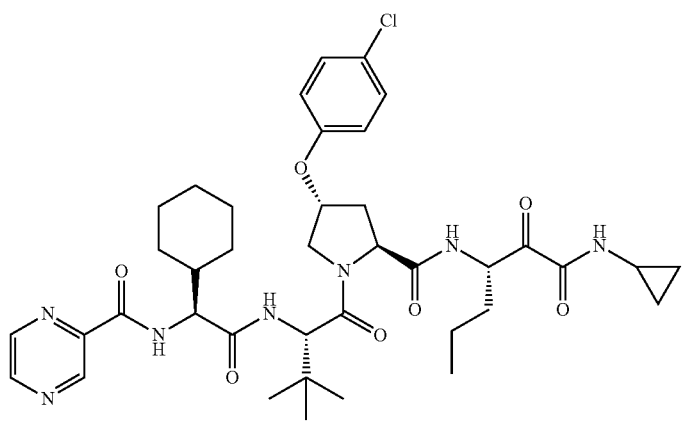 |
| 57 | 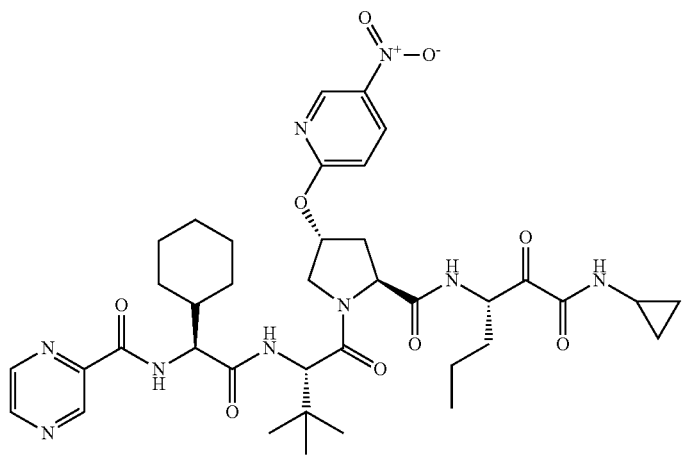 |

| No. | Structure |
|---|---|
| 58 | 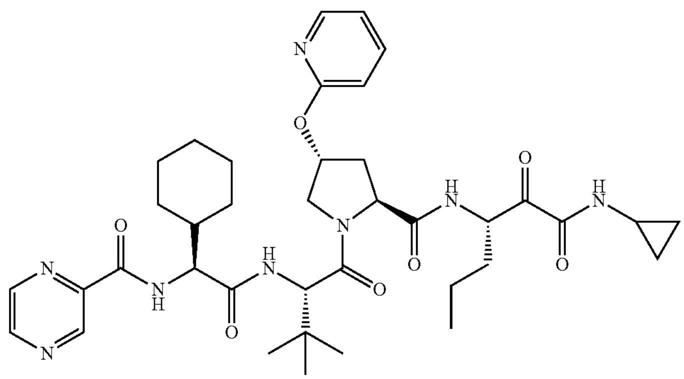 |
| 59 | 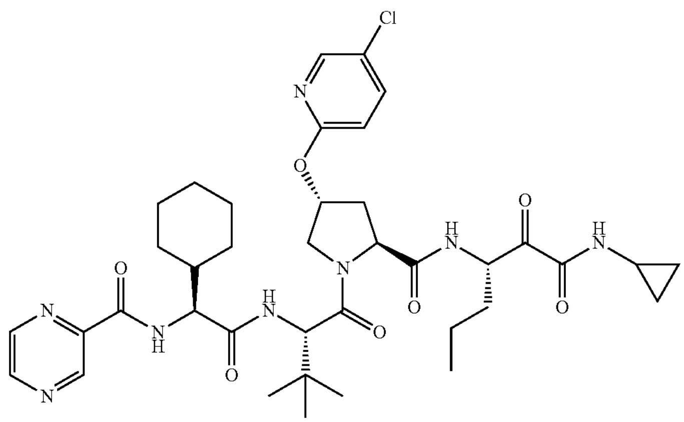 |
| 60 | 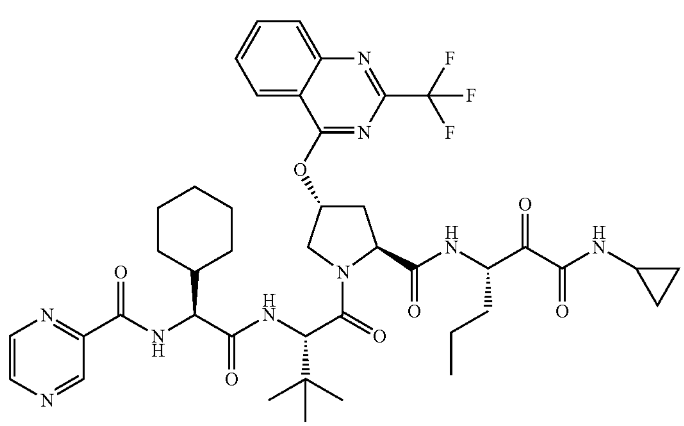 |

-continued
| No. | Structure |
|---|---|
| 61 | 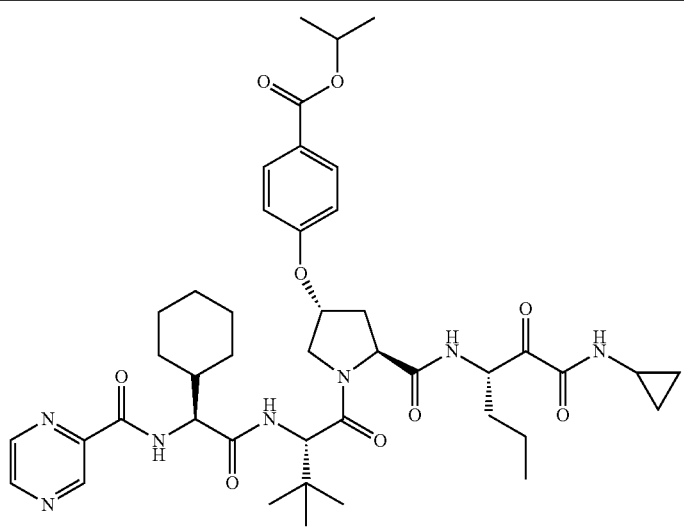 |
| 62 | 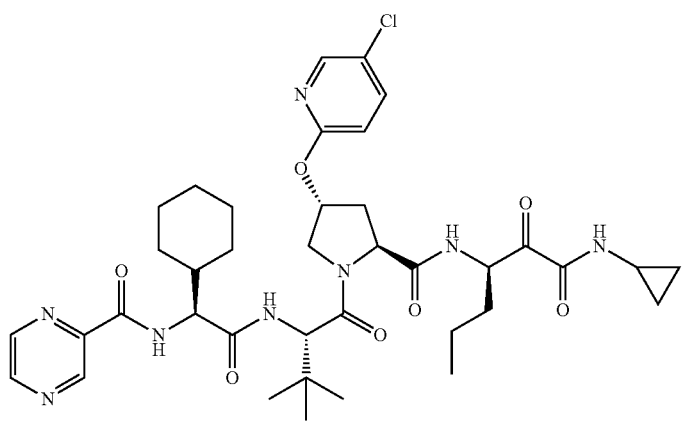 |
| 63 | 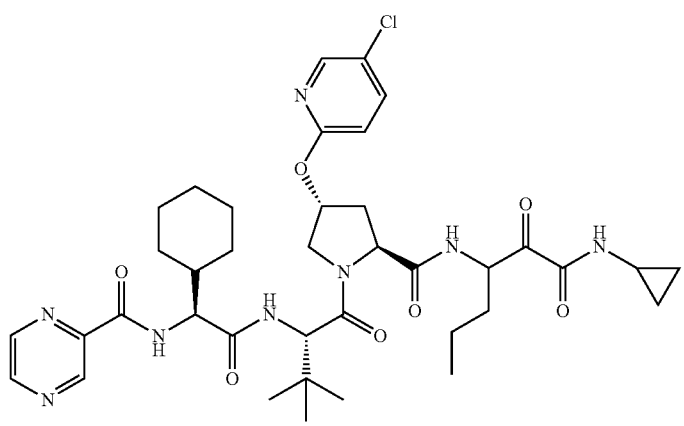 |

| No. | Structure |
|---|---|
| 64 | 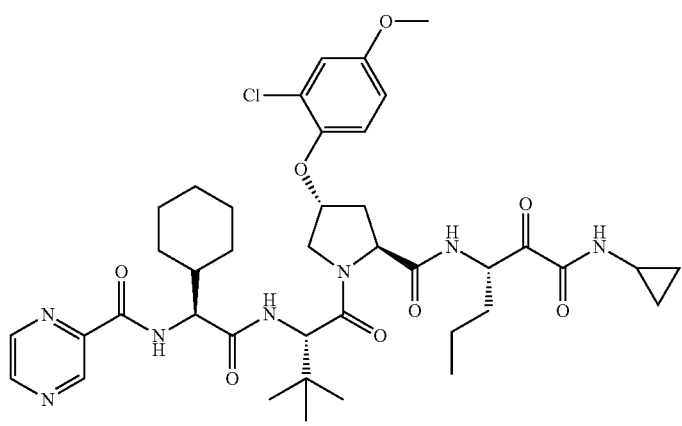 |
| 65 | 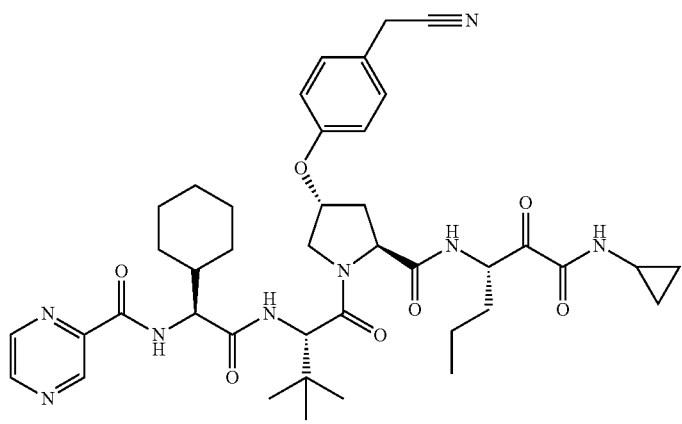 |
| 66 | 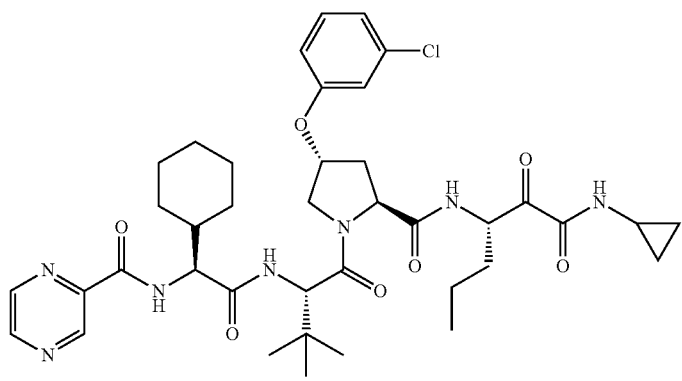 |

-continued
| No. | Structure |
|---|---|
| 67 | 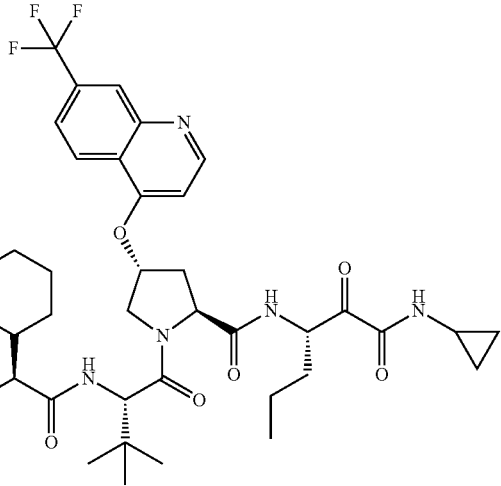 |
| 68 | 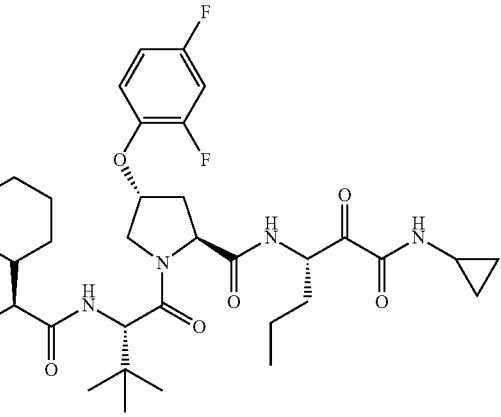 |
| 69 | 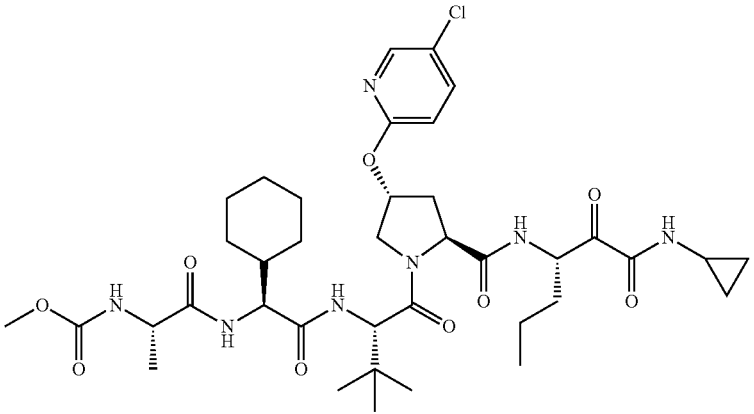 |

-continued
| No. | Structure |
|---|---|
| 70 | 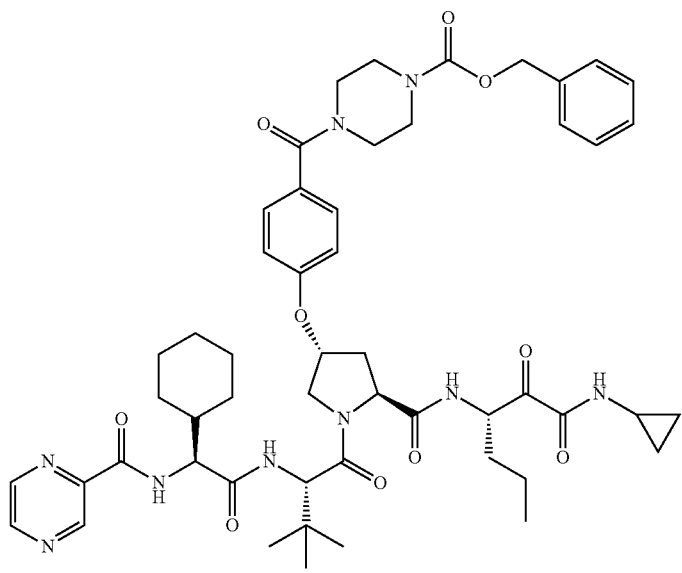 |
| 71 | 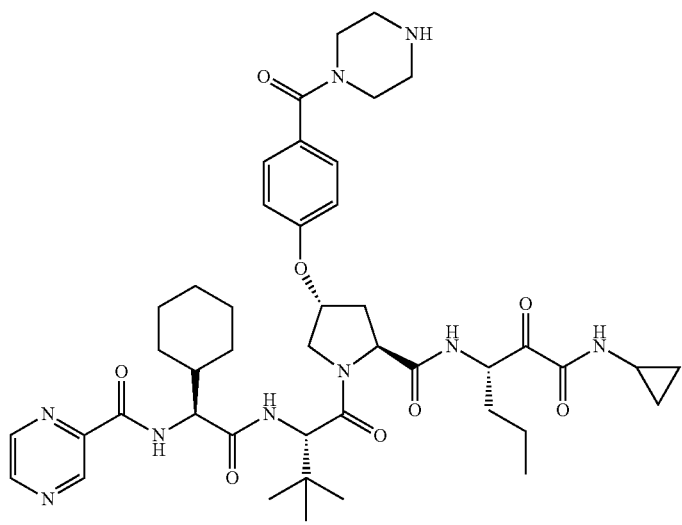 |
| 72 | 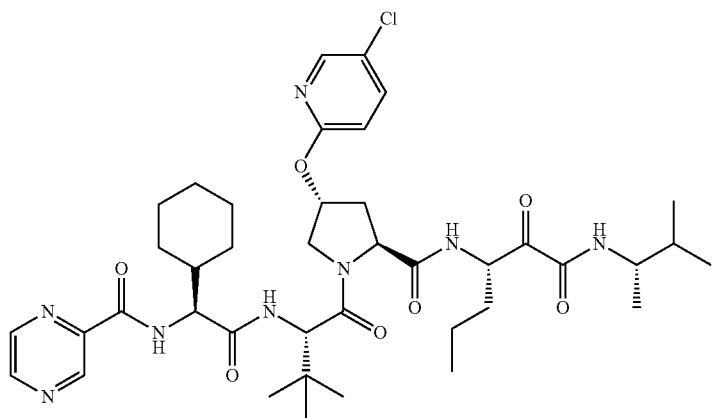 |

| No. | Structure |
|---|---|
| 73 | 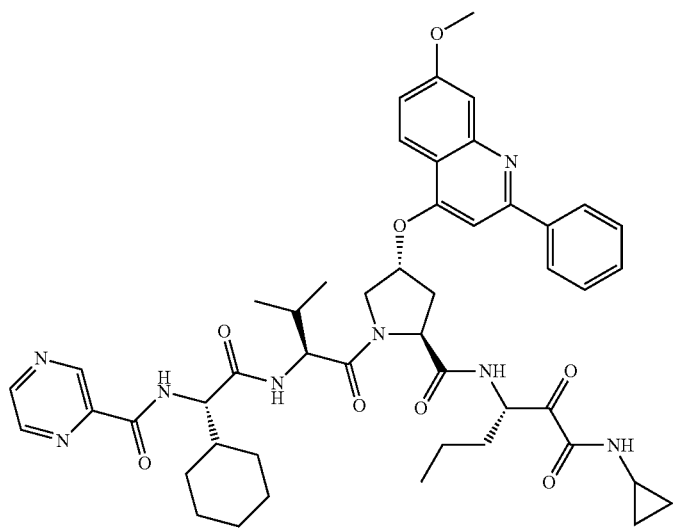 |
| 74 | 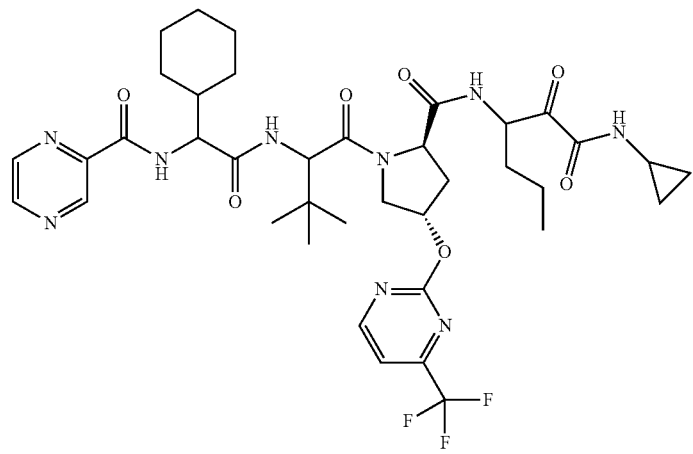 |
| 75 | 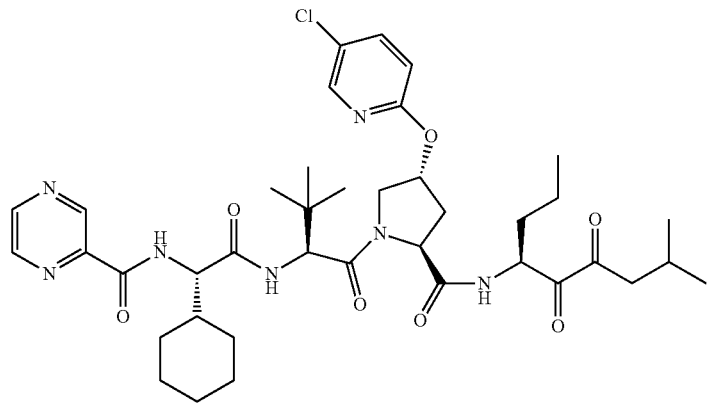 |

| No. | Structure |
|---|---|
| 76 | 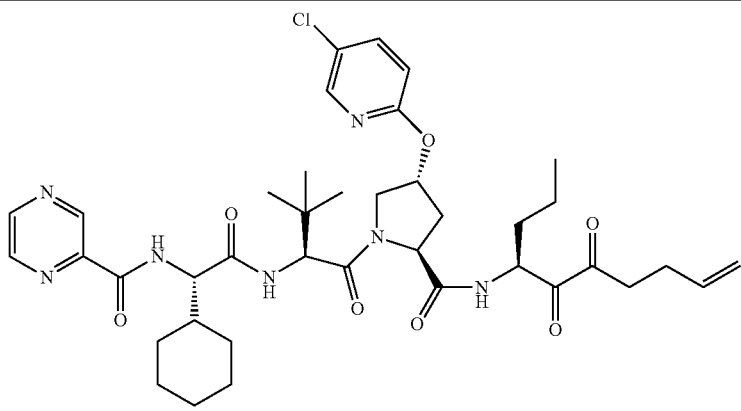 |

Example 4

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well, RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

Example 5

HCV Ki Assay Protocol

HPLC Microbore Method for Separation of 5AB Substrate and Products

Substrate:

$NH_2$-Glu-Asp-Val-Val-(alpha)Abu-Cys-Ser-Met-Ser-Tyr-COOH

A stock solution of 20 mM 5AB (or concentration of your choice) was made in DMSO w/0.2M DTT. This was stored in aliquots at −20 C.

Buffer: 50 mM HEPES, pH 7.8; 20% glycerol; 100 mM NaCl

Total assay volume was 100 μL

|  | X1 (μL) | conc. in assay |
|---|---|---|
| Buffer | 86.5 | see above |
| 5 mM KK4A | 0.5 | 25 μM |
| 1M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB).

Incubated for 20 min at 30 C.
Terminated reaction by addition of 25 μL of 10% TFA
Transferred 120 μL aliquots to HPLC vials
Separated SMSY product from substrate and KK4A by the following method:
Microbore Separation Method:
Instrumentation: Agilent 1100
Degasser G1322A
Binary pump G1312A
Autosampler G1313A
Column thermostated chamber G1316A
Diode array detector G1315A
Column:
Phenomenex Jupiter; 5 micron C18; 300 angstroms; 150×2 mm; P/O 00E-4053-B0
Column thermostat: 40 C
Injection volume: 100
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Compounds of this invention have been tested in either the Example 4 and/or the Example 5 assays and have been shown to have HCV NS3-NS4A protease inhibition activity. Certain preferred compounds of this invention have comparable cell (Example 4) and enzymology (Example 5) data. Compounds 2, 7, 12, 13, 14, 18, 22, 24, 26, 34, 45, 50, 53, 54, 55, 57, 59, 61, 65, and 66, have comparable cell and enzyme data. More preferred compounds are 24, 45, 53, 54, 59, and 61 having comparable enzyme and cell data and both types of data falling within Category A.

Compounds of this invention were tested according to Example 5 (enzyme) and found to have Ki values of <0.1 μM (Category A); 0.1-0.3 μM (Category B); and >0.3 μM (Category C) as follows.
Category A: 15, 19, 20, 24, 32, 35, 36, 37, 38, 39, 40, 41, 42, 43, 44, 45, 46, 49, 51, 52, 53, 54, 56, 58, 59, 61, 64, 67, and 69.
Category B: 1, 2, 3, 4, 5, 7, 8, 10, 12, 13, 14, 16, 18, 22, 23, 25, 30, 31, 33, 26, 34, 48, 50, 55, 57, 60, 65, 66, 70, 71, and 76.
Category C: 6, 9, 11, 17, 21, 27, 28, 29, 47 74, 75, and 76.

Compounds of this invention were tested according to Example 4 (cell) and found to have IC50 values of <0.5 μM (Category A); 0.5-1.0 μM (Category B); and >1.0 μM (Category C) as follows.
Category A: 7, 12, 13, 14, 15, 18, 19, 22, 24, 34, 35, 36, 38, 39, 40, 42, 43, 44, 45, 46, 47, 48, 50, 53, 54, 55, 56, 26, 57, 58, 59, 61, 64, 65, 66, and 67.
Category B: 1, 2, 3, 4, 5, 8, 10, 16, 20, and 70.
Category C: 6, 11, 41, 46, 47, 48, 49, 51, 60, and 71.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above. All cited documents are incorporated herein by reference.

We claim:
1. A compound of formula I:

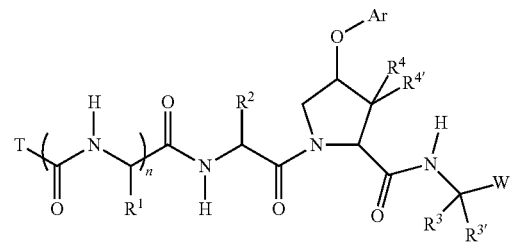

wherein:
n is 0 or 1;
Ar is a 5- to 10-membered aromatic ring having up to 4 heteroatoms selected from O, S, N(H), SO, and $SO_2$, wherein 1 to 3 ring atoms are optionally and independently substituted with J;
$R^1$, $R^2$, $R^{12}$, and $R^{13}$ are independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-,
(C6-C10)-heteroaryl-(C1-C12)aliphatic-,
wherein up to 3 aliphatic carbon atoms in $R^1$ and $R^2$ may be replaced by a heteroatom selected from O, N, NH, S, SO, or $SO_2$ in a chemically stable arrangement;
wherein each of $R^1$ and $R^2$ is independently and optionally substituted at each substitutable position with up to 3 substituents independently selected from J;
$R^3$ and $R^{3'}$ are independently hydrogen or (C1-C12)-aliphatic, wherein any hydrogen is optionally replaced with halogen; wherein any terminal carbon atom of $R^3$ is optionally substituted with sulfhydryl or hydroxy; or $R^3$ is phenyl or —$CH_2$-phenyl, wherein said phenyl group is optionally substituted with up to 3 substituents independently selected from J; or
$R^3$ and $R^{3'}$ together with the atom to which they are bound is a 3- to 6-membered ring having up to 2 heteroatoms selected from N, NH, O, SO, and $SO_2$; wherein the ring has up to 2 substituents selected independently from J;
$R^4$ and $R^{4'}$ are independently:
hydrogen-,
(C1-C12)-aliphatic-,
(C3-C10)-cycloalkyl- or -cycloalkenyl-,
(C3-C10)-cycloalkyl-(C1-C12)-aliphatic-,
(C6-C10)-aryl-,
(C3-C10)-heterocyclyl-; or
(C5-C10)-heteroaryl-;
wherein up to two aliphatic carbon atoms in $R^4$ and $R^{4'}$ may be replaced by a heteroatom selected from O, N, S, SO, and $SO_2$;
wherein each of $R^4$ and $R^{4'}$ is independently and optionally substituted with up to 3 substituents independently selected from J;

W is:

wherein
Y is —CO$_2$H, a derivative of —CO$_2$H, or a bioisostere of —CO$_2$H;
each R$_6$ is independently:
  hydrogen-,
  (C1-C12)-aliphatic-,
  (C6-C10)-aryl-,
  (C6-C10)-aryl-(C1-C12)aliphatic-,
  (C3-C10)-cycloalkyl- or cycloalkenyl-,
  [(C3-C10)-cycloalkyl- or cycloalkenyl]-(C1-C12)-aliphatic-,
  (C3-C10)-heterocyclyl-,
  (C3-C10)-heterocyclyl-(C1-C12)-aliphatic-,
  (C5-C10)heteroaryl-, or
  (C5-C10)heteroaryl-(C1-C12)-aliphatic-, or
    two R$_6$ groups, which are bound to the same nitrogen atom, form together with that nitrogen atom, a (C3-C10)-heterocyclic ring;
    wherein R$_6$ is optionally substituted with up to 3 J substituents;
  wherein each R$_8$ is independently —OR; or the R$_8$ groups together with the boron atom, is a (C3-C10)-membered heterocyclic ring having in addition to the boron up to 3 additional heteroatoms selected from N, NH, O, SO, and SO$_2$;
T is:
  (C1-C12)-aliphatic-;
  (C6-C10)-aryl-,
  (C6-C10)-aryl-(C1-C12)aliphatic-,
  (C5-C10)heteroaryl-, or
  (C5-C10)heteroaryl-(C1-C12)-aliphatic-;
    wherein each T is optionally substituted with up to 3 J substituents; and
    wherein up to 3 aliphatic carbon atoms in T may be replaced by a heteroatom selected from O, N, NH, S, SO, or SO$_2$ in a chemically stable arrangement;
    provided that if T is pyrrole, the pyrrole is not substituted at the 3-position with J, with J being —C(O)R', —C(O)C(O)R', —C(O)CH$_2$C(O)R', —C(S)R', —C(S)OR', —C(O)OR', —C(O)C(O)OR', —C(O)C(O)N(R')$_2$, —C(O)N(R')$_2$, —C(S)N(R')$_2$, —C(=NH)N(R)$_2$, —C(O)N(OR')R', —C(=NOR')R';
J is halogen, —OR', —NO$_2$, —CN, —CF$_3$, —OCF$_3$, —R', oxo, thioxo, 1,2-methylenedioxy, 1,2-ethylenedioxy, =N(R'), =N(OR'), —N(R$^1$)$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(S)OR', —C(O)OR', —C(O)C(O)OR', —C(O)C(O)N(R)'$_2$, —OC(O)R', —C(O)N(R')$_2$, —OC(O)N(R)$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR)$_2$, —P(O)(R')$^2$, —P(O)(OR')$_2$, or —P(O)(H)(OR');

R' is:
  hydrogen-,
  (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, or
  (C5-C10)-heteroaryl-(C1-C12)-aliphatic-;
    wherein R' is optionally substituted with up to 3 J groups;
  wherein two R' groups bound to the same atom form a 3- to 10-membered aromatic or non-aromatic ring having up to 3 heteroatoms independently selected from N, O, S, SO, or SO$_2$, wherein said ring is optionally fused to a (C6-C10)aryl, (C5-C10)heteroaryl, (C3-C10)cycloalkyl, or a (C3-C10)heterocyclyl, wherein any ring has up to 3 substituents selected independently from J.

2. The compound according to claim 1, wherein Ar is phenyl, pyridyl, quinolinyl, pyrimidinyl, or naphthyl, wherein each group is optionally substituted with 1, 2, or 3 J groups.

3. The compound according to claim 1, wherein Ar is

-continued

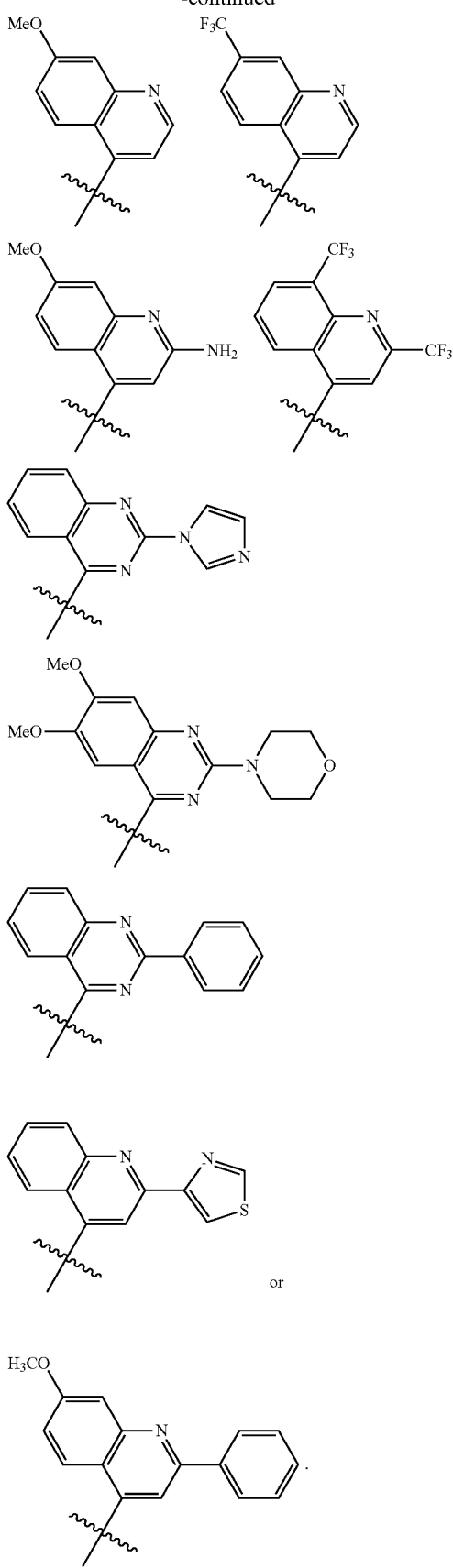

4. The compound according to claim 1, wherein Ar is:

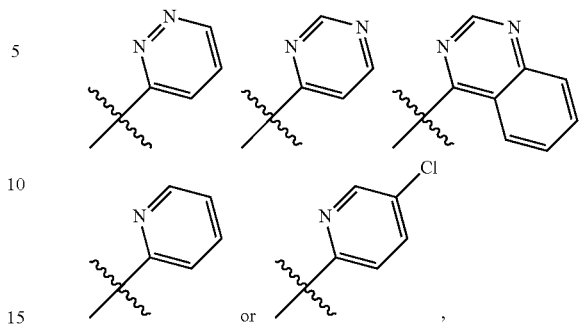

5. The compound according to claim 1, wherein Ar is a 6 or a 10-membered aromatic ring having 0, 1, or 2 nitrogen heteroatoms, wherein 1, 2, or 3 ring atoms are optionally and independently substituted with J.

6. The compound according to any one of claims 1-5, wherein each J group on Ar is independently OR', $NO_2$, CN, $CF_3$, $OCF_3$, R', COR', C(O)OR', C(O)N(R')$_2$, $SO_2$R', $SO_2$N(R')$_2$, 1,2-methylenedioxy, 1,2-ethylene dioxy, or NR'C(O)OR', NR'$SO_2$R'.

7. The compound according to any one of claims 1-5, wherein each J group on Ar is independently OR', halogen, CN, $CF_3$, R', or COR'.

8. The compound according to any one of claims 1-5, wherein each J group on Ar is independently halo, trifluoromethyl, methyl, or $NO_2$.

9. The compound according to any one of claims 1-5, wherein W is:

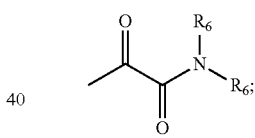

wherein the $NR^6R^6$ is —NH—(C1-C6 aliphatic), —NH—(C3-C6 cycloalkyl), —NH—CH(CH$_3$)-aryl, or —NH—CH(CH$_3$)-heteroaryl, wherein said aryl or said heteroaryl is optionally substituted with up to 3 halogens.

10. The compound according to any one of claims 1-5, wherein in the W, the $NR^6R^6$ is:

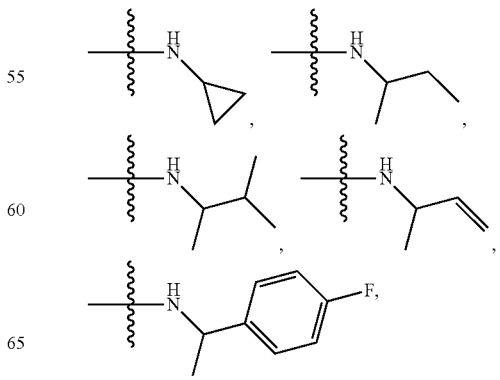

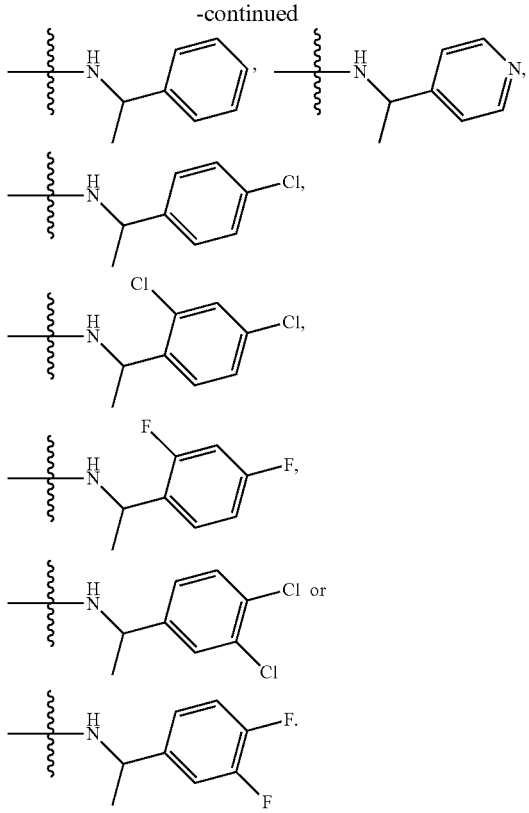

11. The compound according to any one of claims 1-5, wherein in the W, the NR⁶R⁶ is:

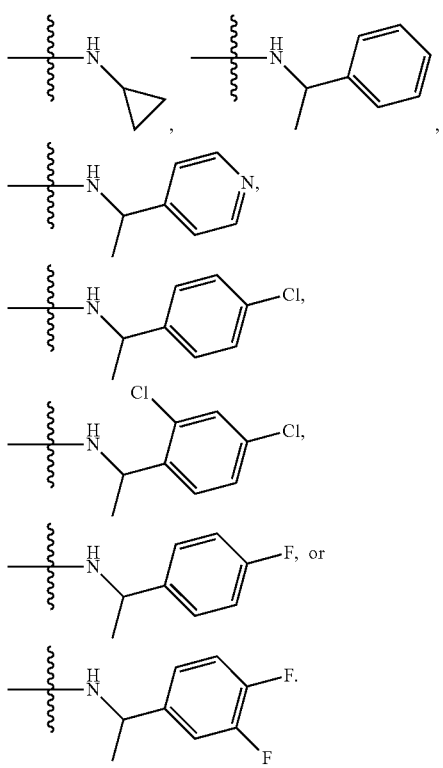

12. The compound according to any one of claims 1-5, wherein in the W, the NR⁶R⁶ is:

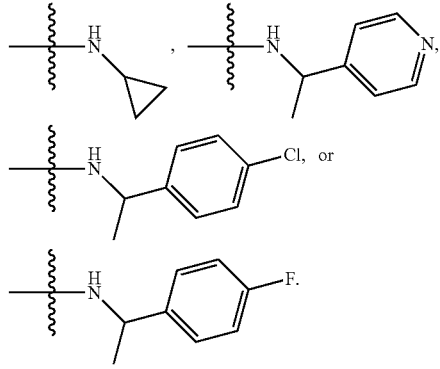

13. The compound according to any one of claims 1-5, wherein in the W, the NR⁶R⁶ is:

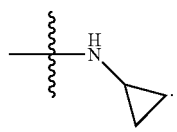

14. The compound according to any one of claims 1-5, wherein R³' is hydrogen and R³ is:

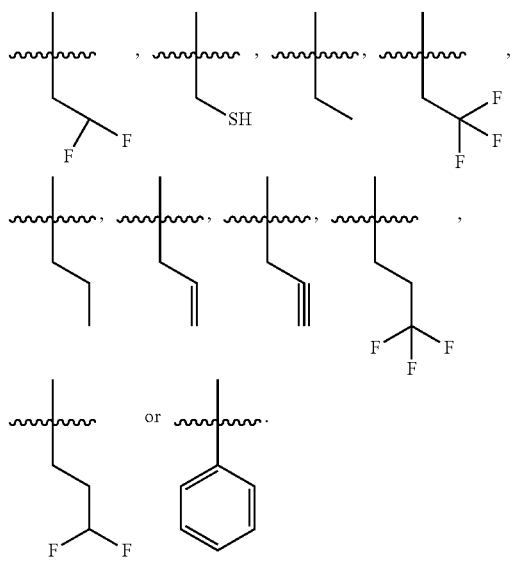

15. The compound according to any one of claims 1-5, wherein R³' is hydrogen and R³ is:

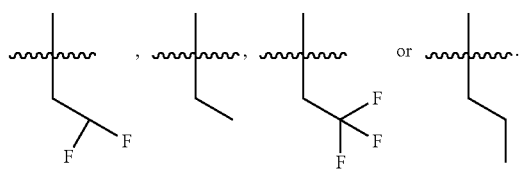

16. The compound according to any one of claims 1-5, wherein R² is:

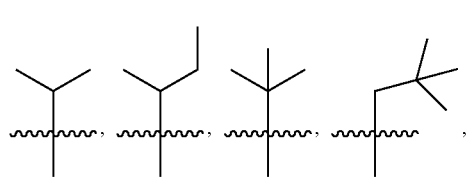

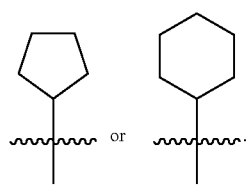

17. The compound according to claim 16, wherein R² is:

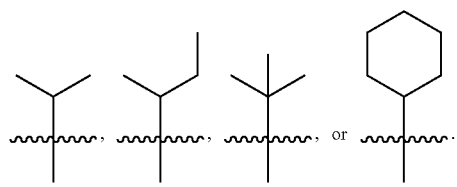

18. The compound according to claim 17, wherein R² is:

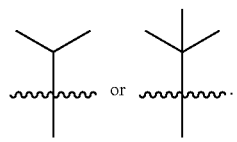

19. The compound according to any one of claims 1-5, wherein R¹ is:

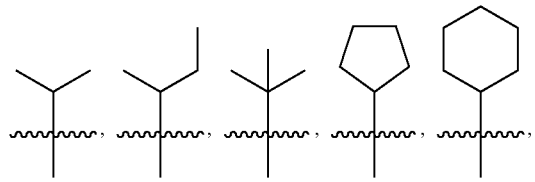

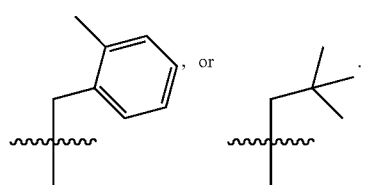

20. The compound according to claim 19, wherein R' is:

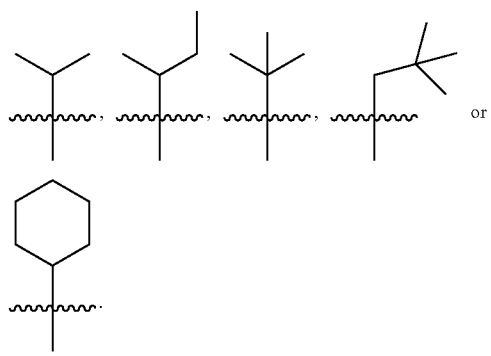

21. The compound according to claim 20, wherein R¹ is cyclohexyl.

22. The compound according to any one of claims 1-5, wherein T is (C6-C10)-aryl- or (C5-C10)heteroaryl-, wherein each T is optionally substituted with 1, 2, or 3 J substituents.

23. The compound according to any one of claims 1-5, wherein T is:

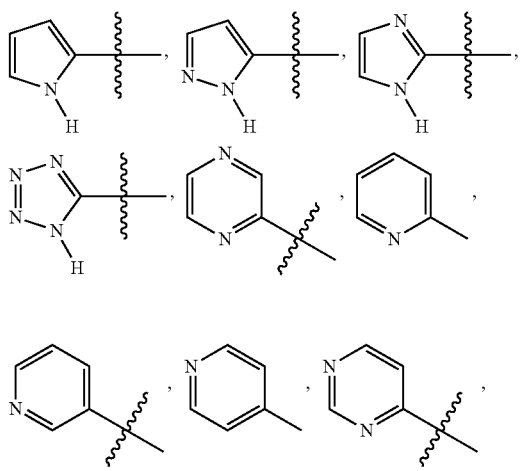

wherein each T group is optionally fused to a 5-membered or a 6-membered aryl or heteroaryl group.

24. The compound according to claim 23, wherein T is:

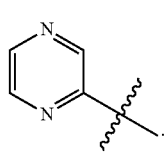

25. The compound according to claim 1 wherein, the compound is:
| No. | Structure |
|---|---|
| 1 | 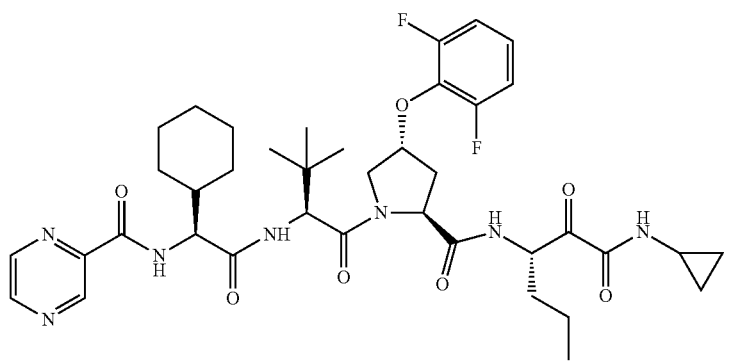 |
| 2 | 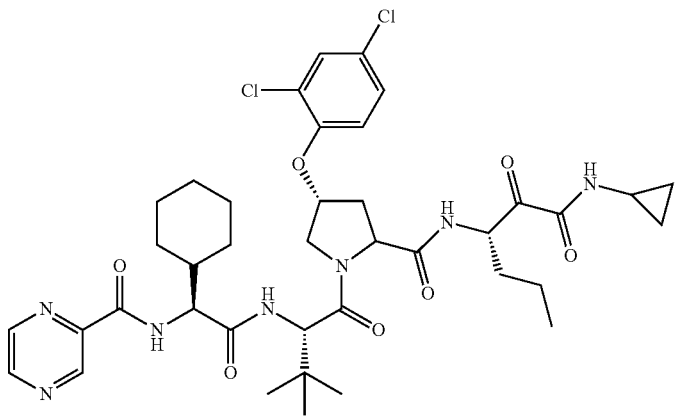 |
| 3 | 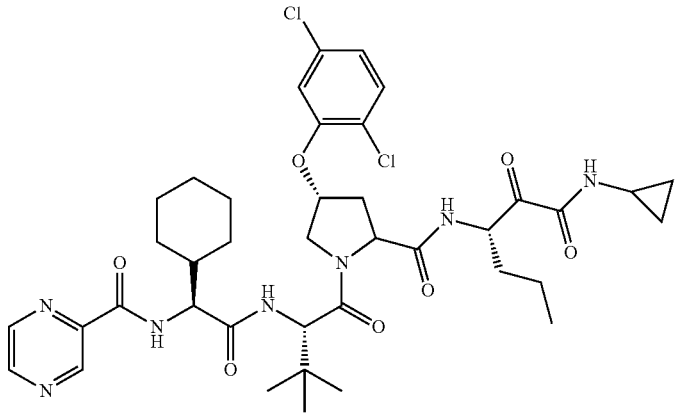 |

| No. | Structure |
|-----|-----------|
| 4 | 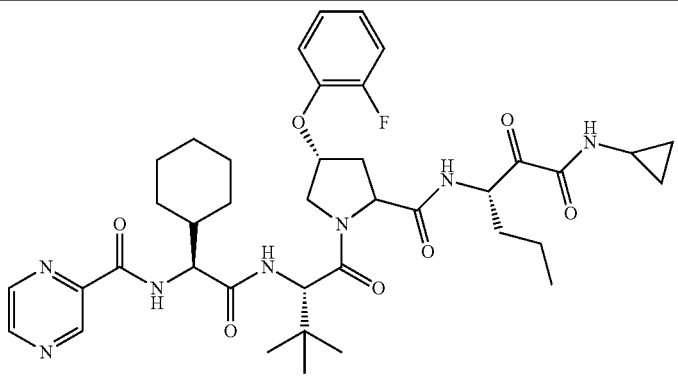 |
| 5 | 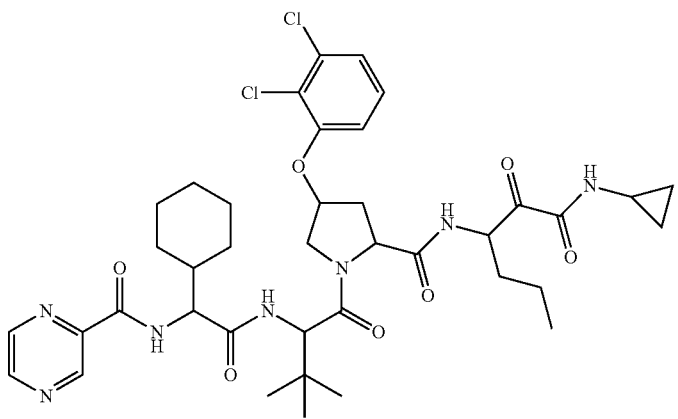 |
| 6 | 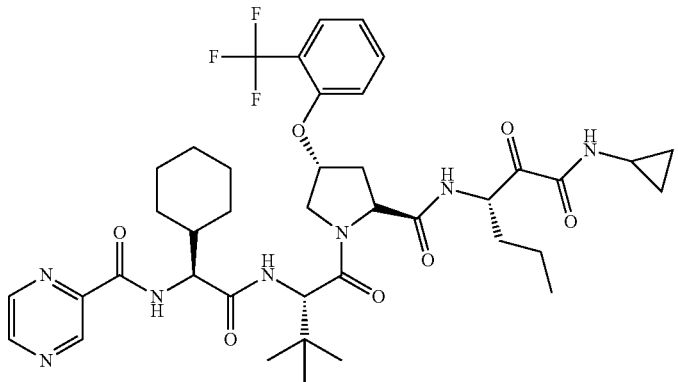 |
| 7 | 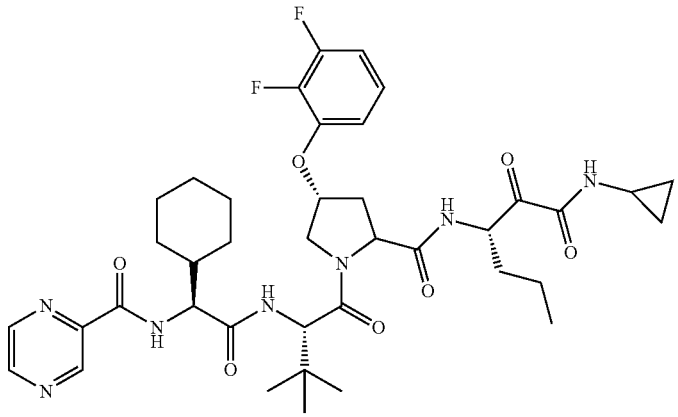 |

| No. | Structure |
|---|---|
| 8 | 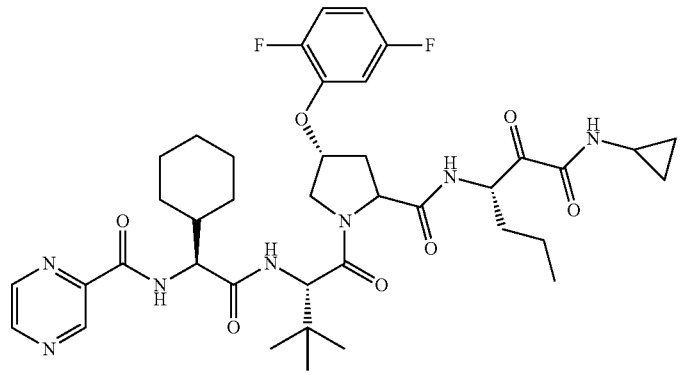 |
| 9 | 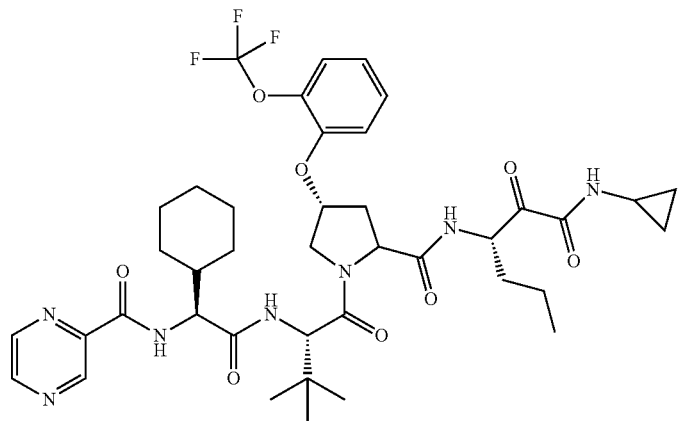 |
| 10 | 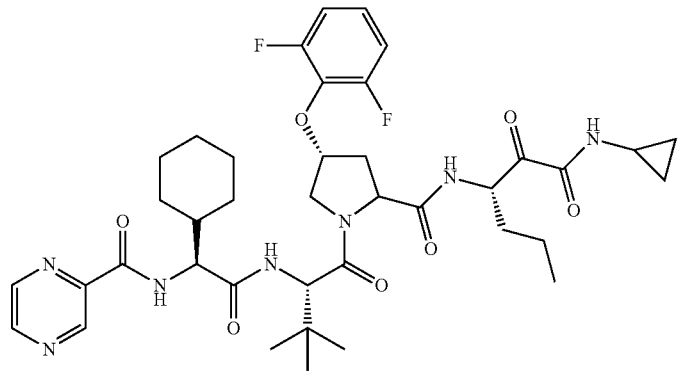 |

| No. | Structure |
| --- | --- |
| 11 | 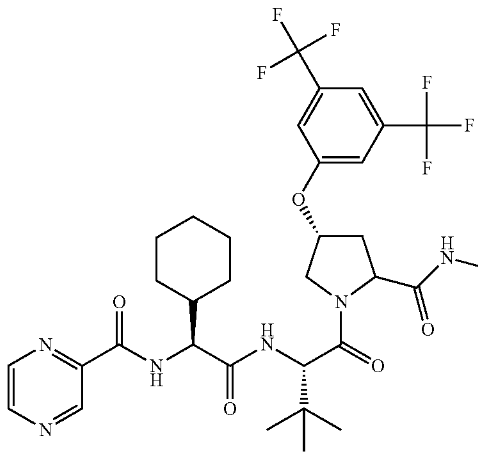 |
| 12 | 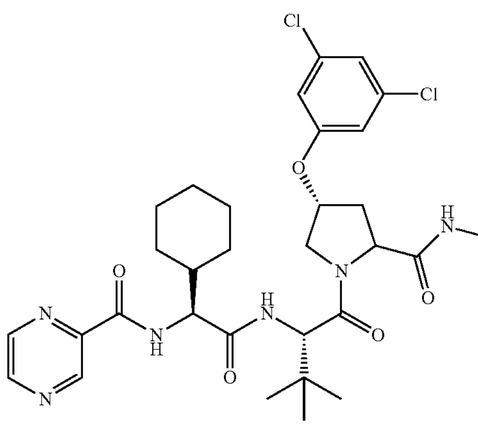 |
| 13 | 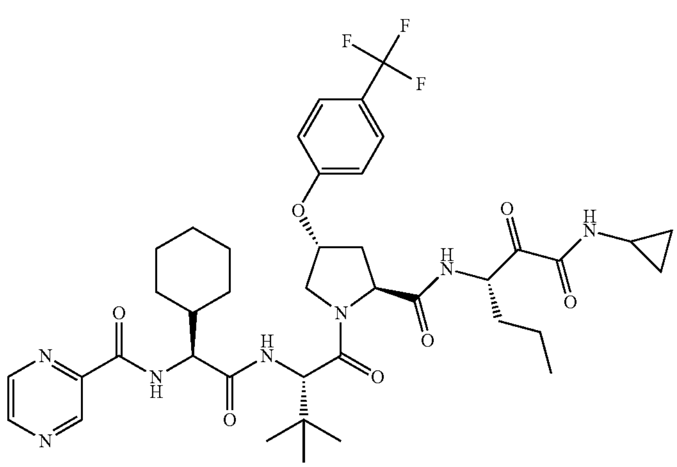 |

-continued

| No. | Structure |
|---|---|
| 14 | 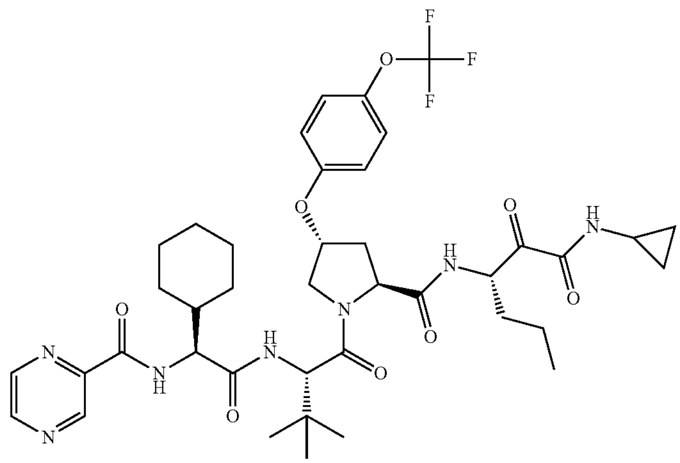 |
| 15 | 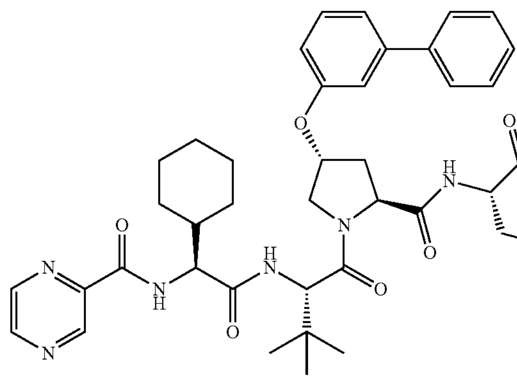 |
| 16 | 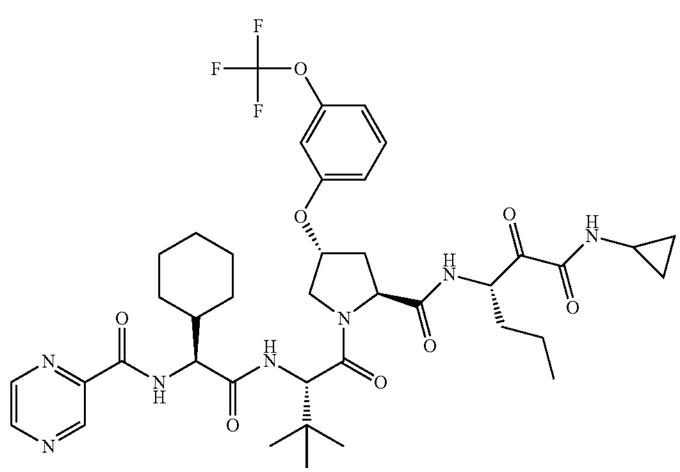 |

-continued

| No. | Structure |
|---|---|
| 17 | 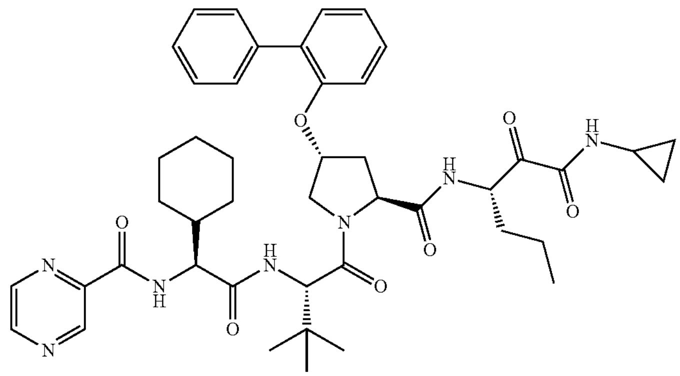 |
| 18 | 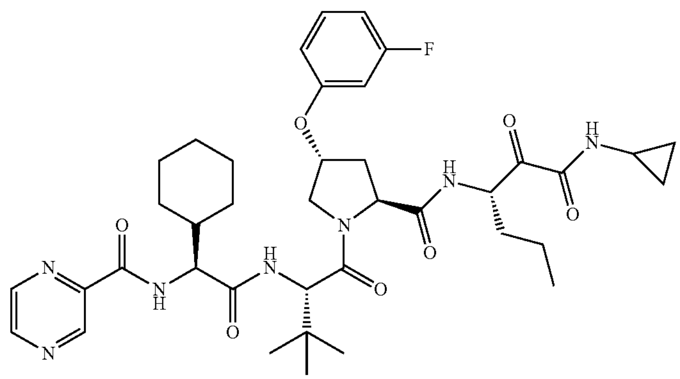 |
| 19 | 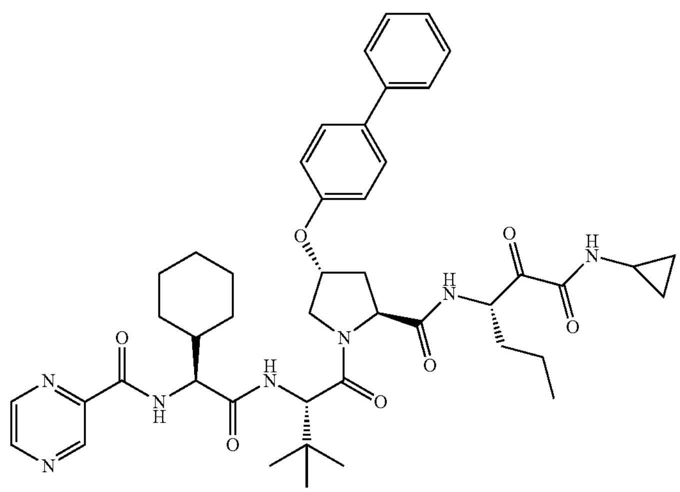 |
| 20 | 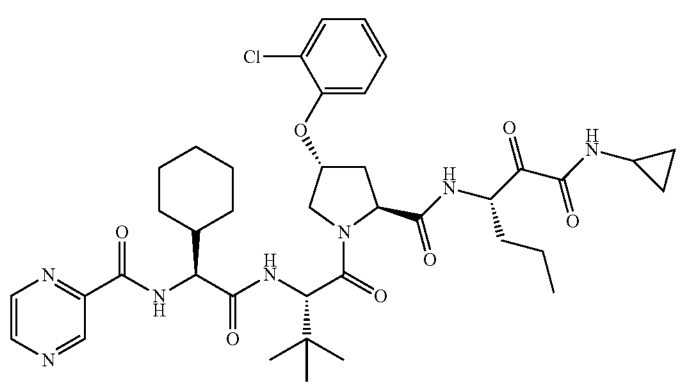 |

-continued
| No. | Structure |
|---|---|
| 21 | 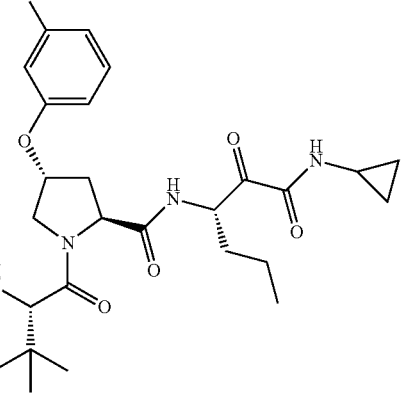 |
| 22 | 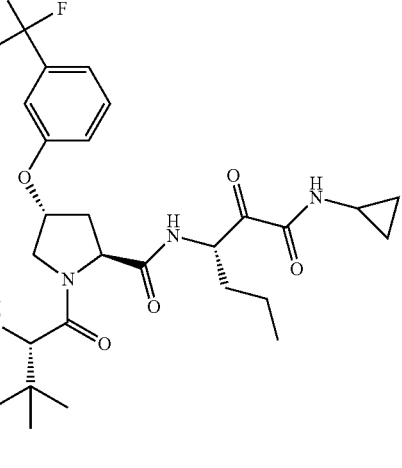 |
| 23 | 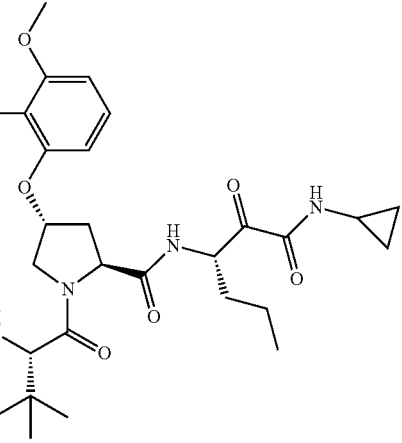 |

| No. | Structure |
|---|---|
| 24 | 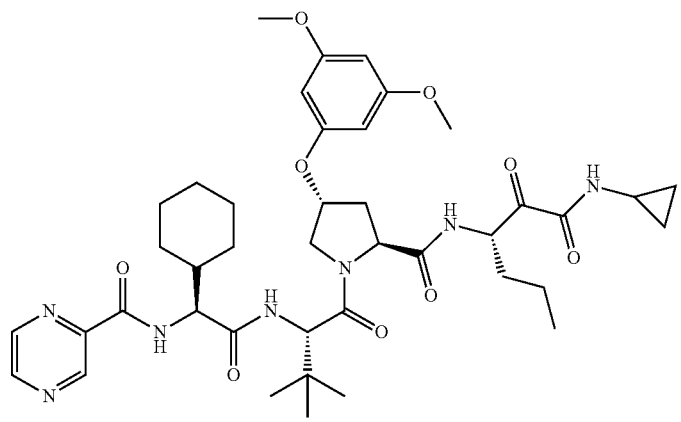 |
| 25 | 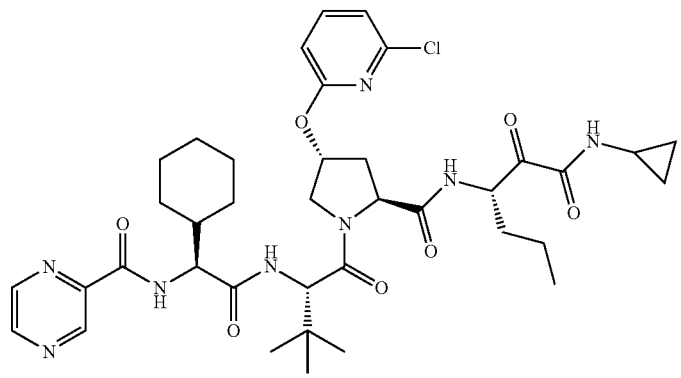 |
| 26 | 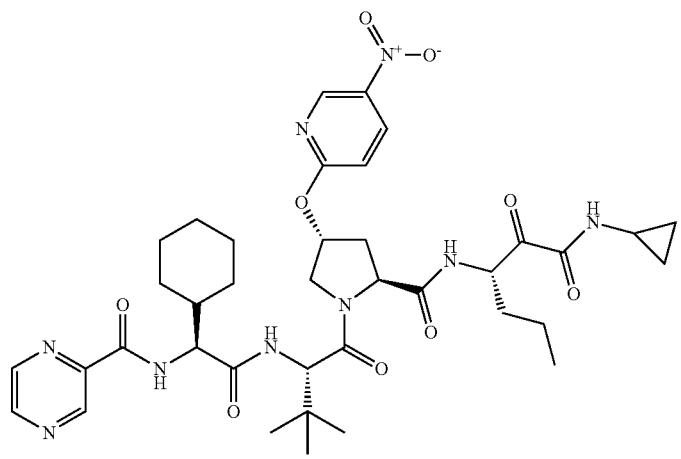 |

| No. | Structure |
|---|---|
| 27 | 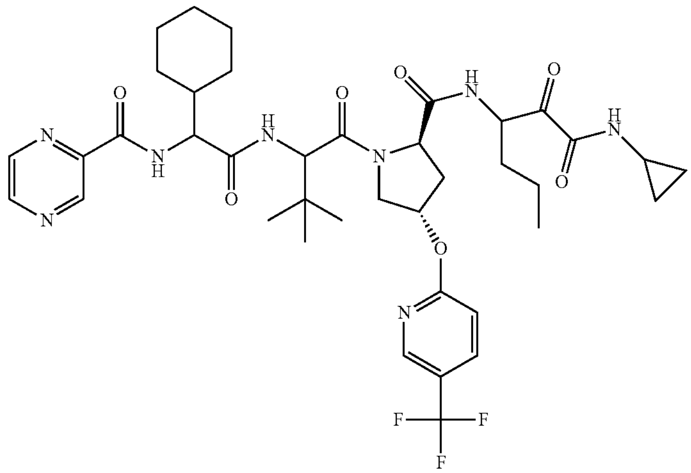 |
| 28 | 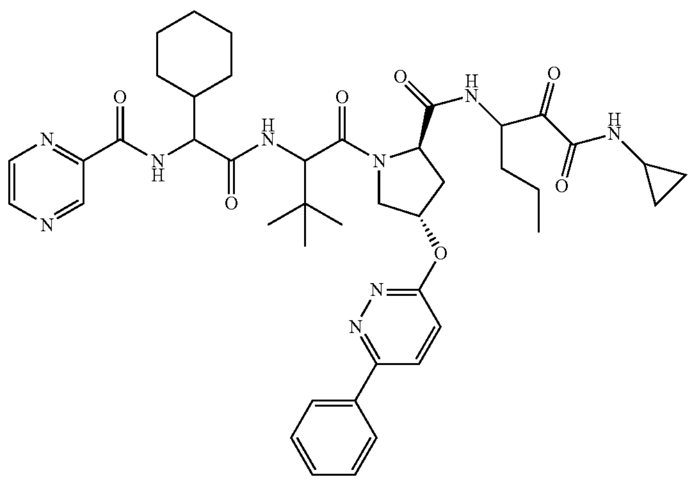 |
| 29 | 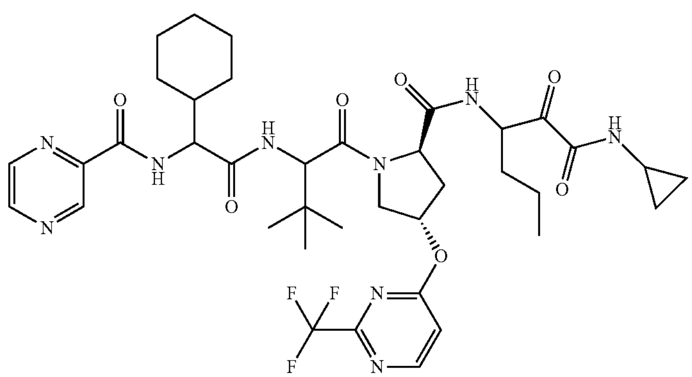 |

| No. | Structure |
|---|---|
| 30 | 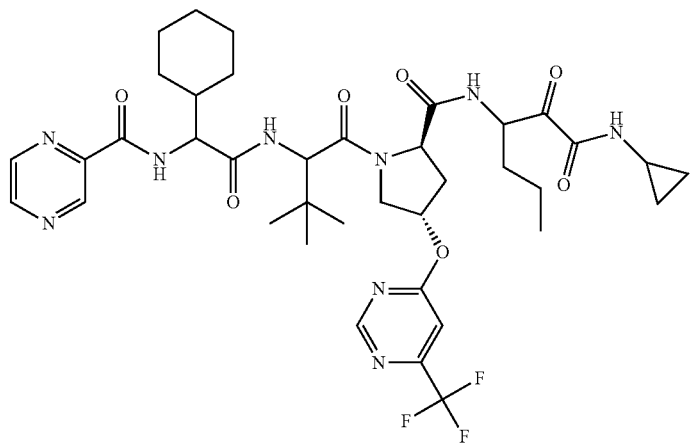 |
| 31 | 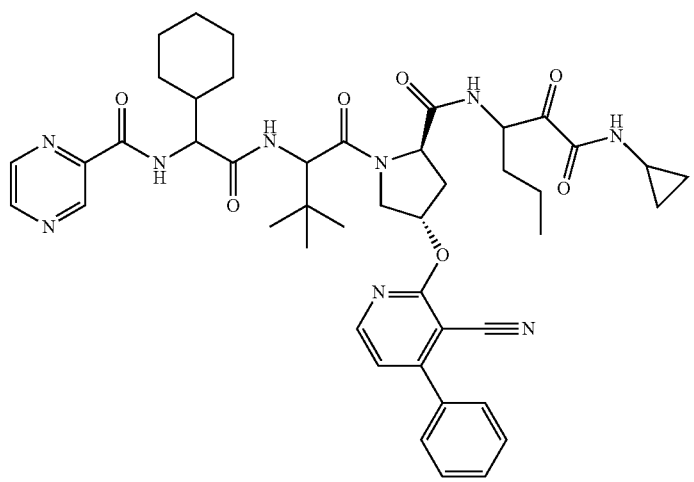 |
| 32 | 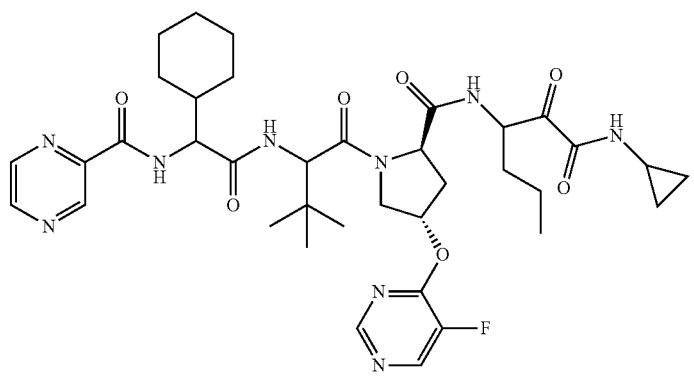 |

-continued
| No. | Structure |
|---|---|
| 33 | 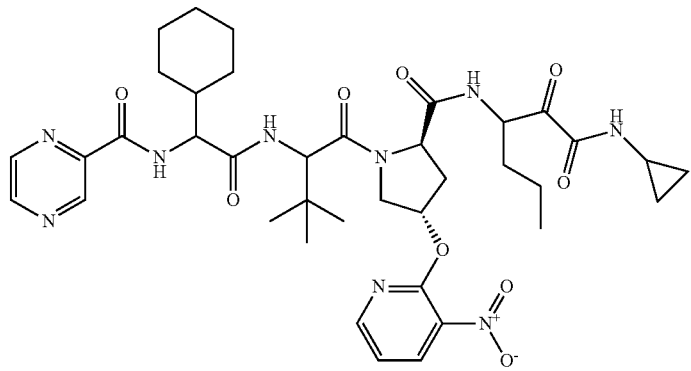 |
| 34 | 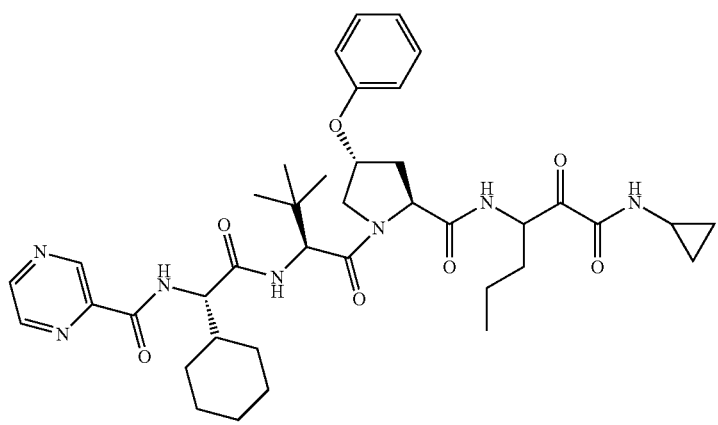 |
| 35 | 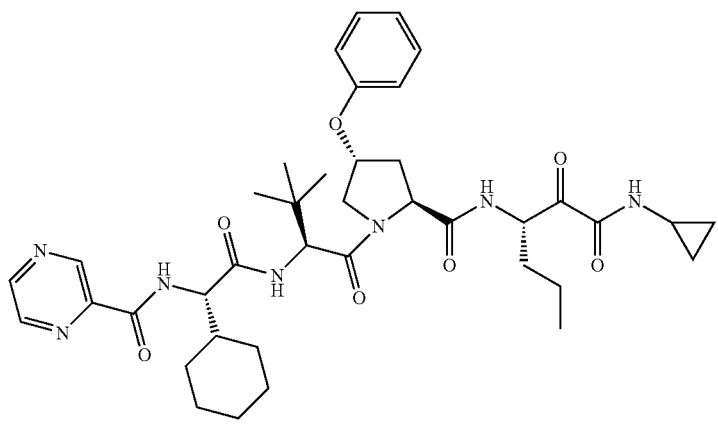 |

|No.|Structure|
|---|---|
|36|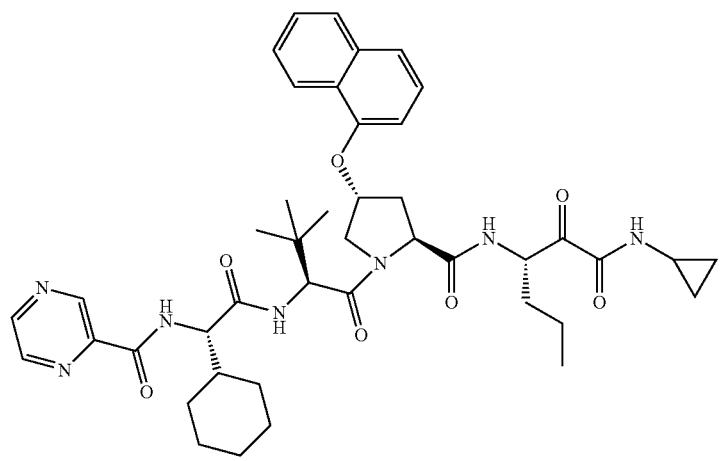|
|37|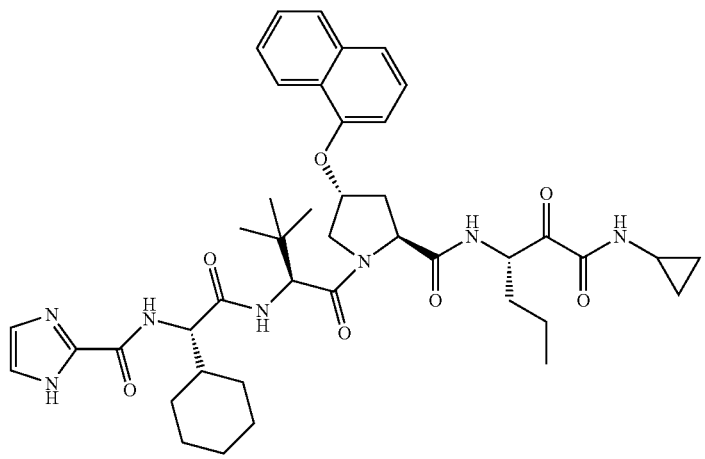|
|38|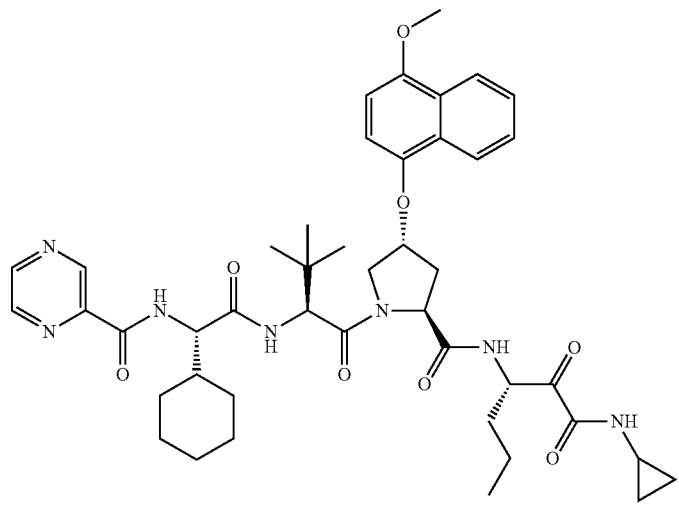|

| No. | Structure |
|---|---|
| 39 | 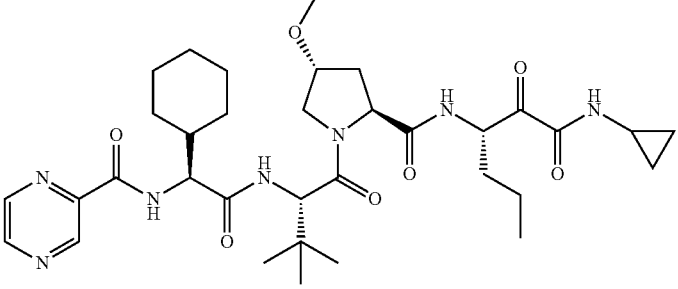 |
| 40 | 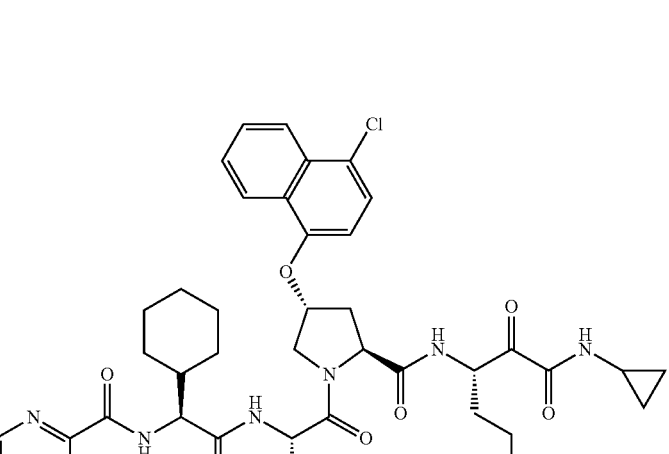 |
| 41 | 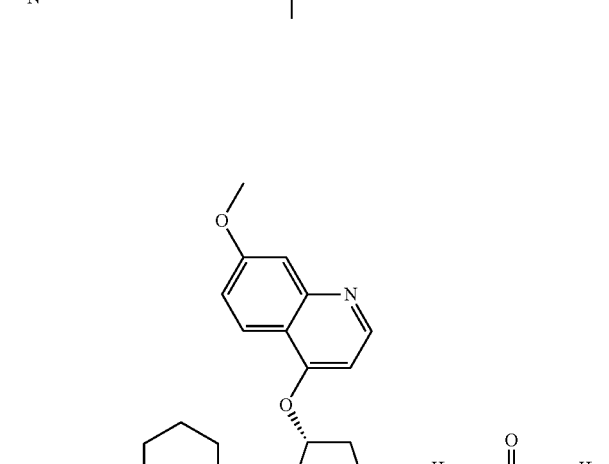 |

| No. | Structure |
|---|---|
| 42 | 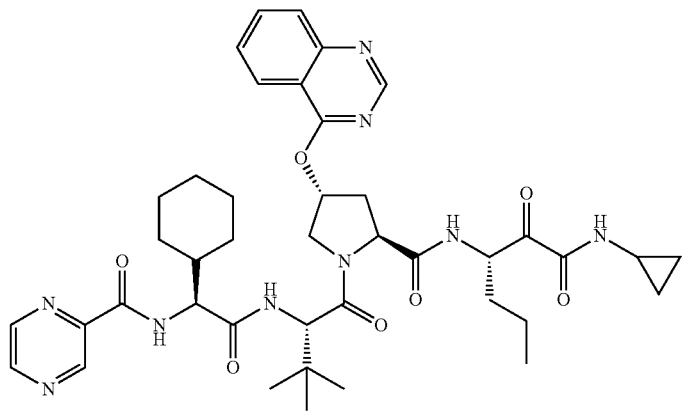 |
| 43 | 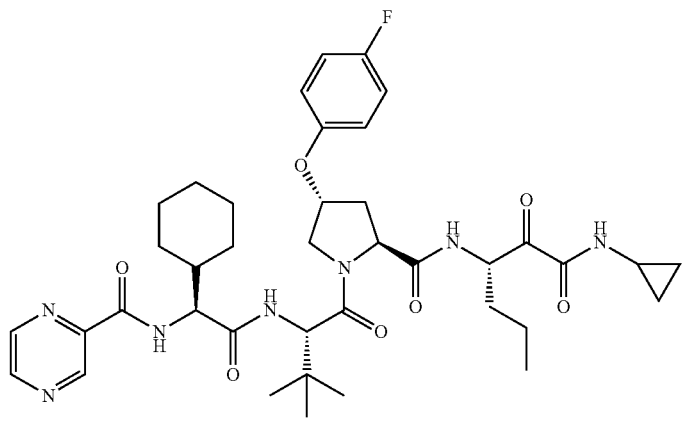 |
| 44 | 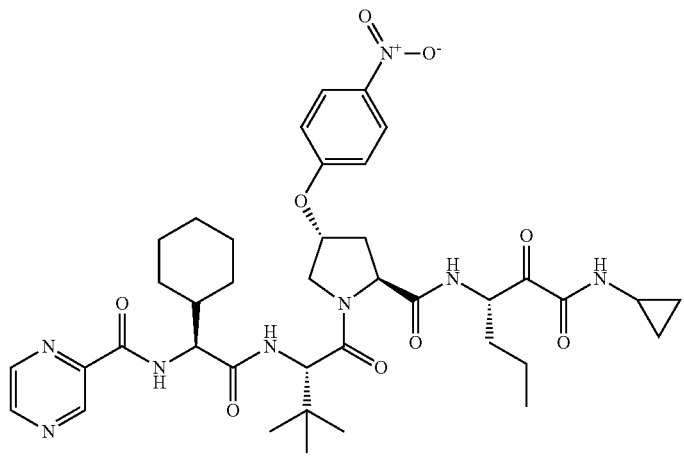 |

| No. | Structure |
|---|---|
| 45 | 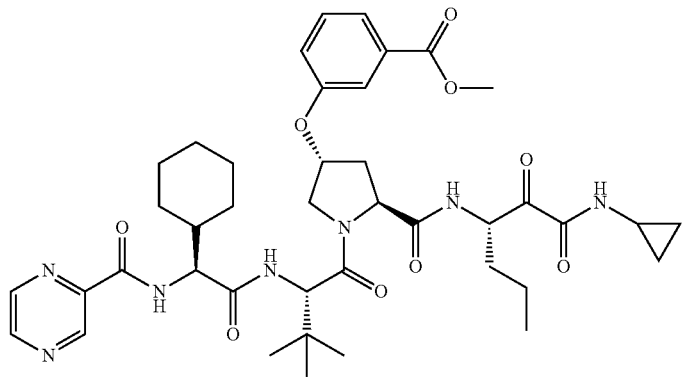 |
| 46 | 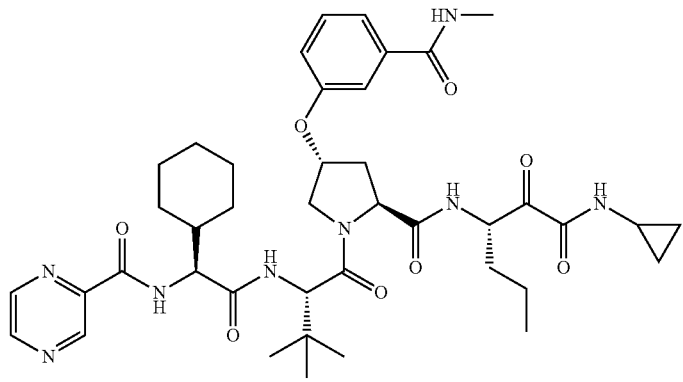 |
| 47 | 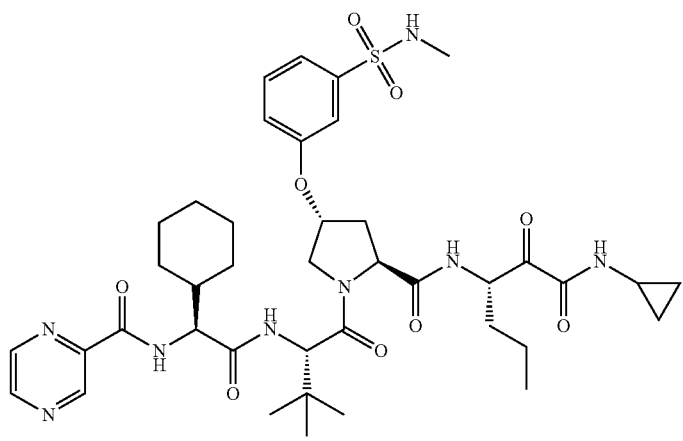 |

-continued
| No. | Structure |
|---|---|
| 48 | 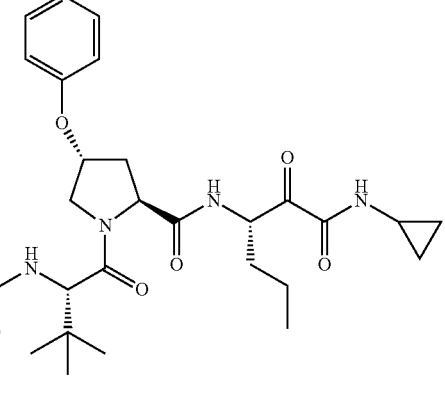 |
| 49 | 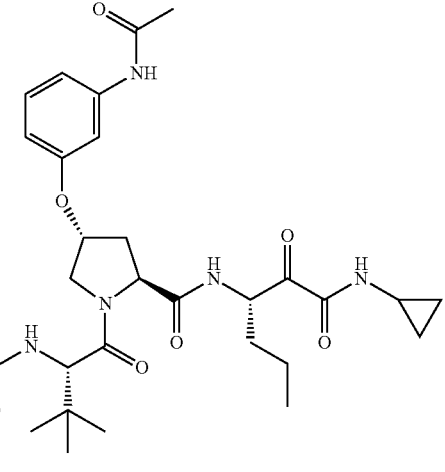 |
| 50 | 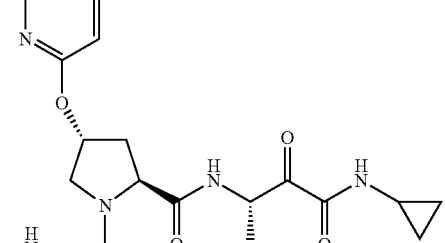 |

-continued
| No. | Structure |
|---|---|
| 51 | 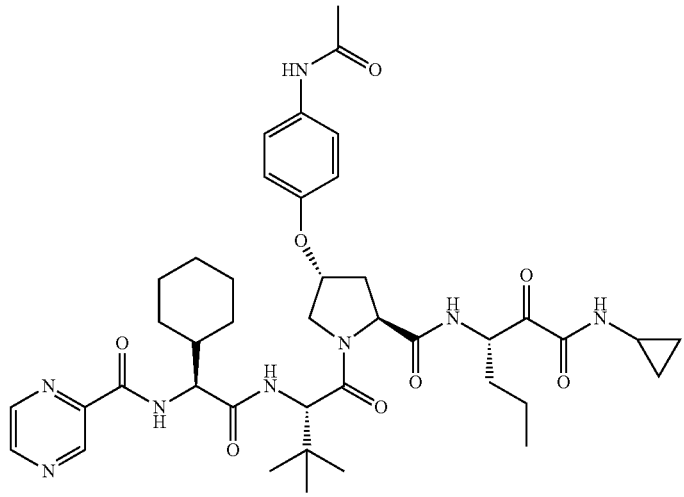 |
| 52 | 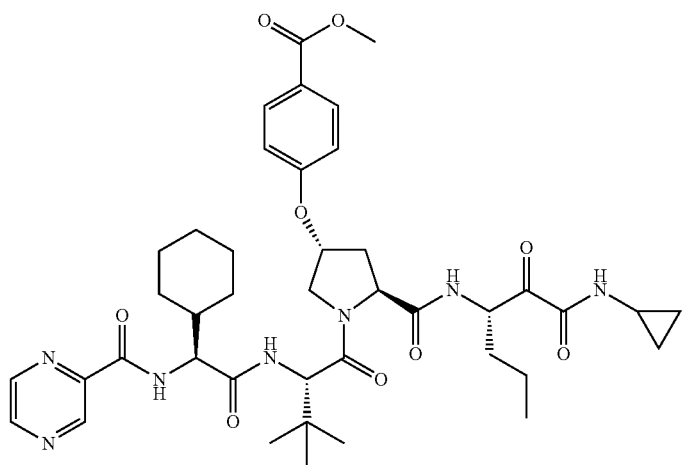 |
| 53 | 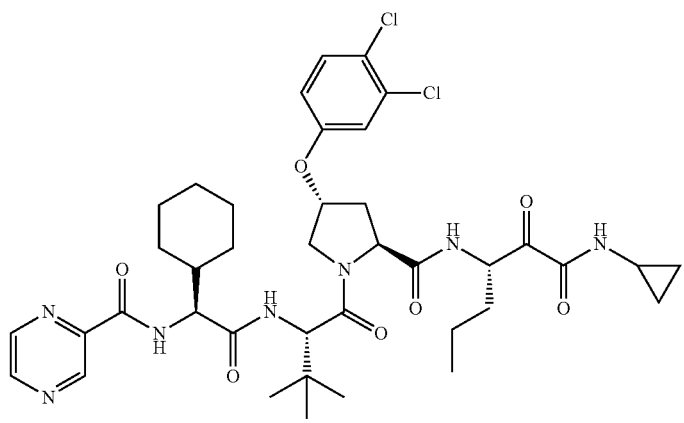 |

| No. | Structure |
|---|---|
| 54 | 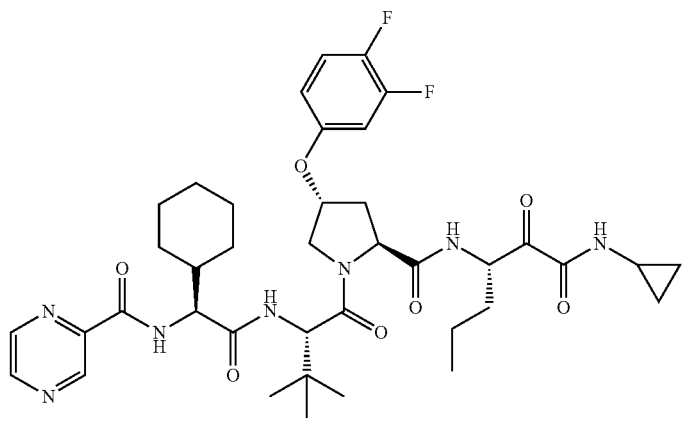 |
| 55 | 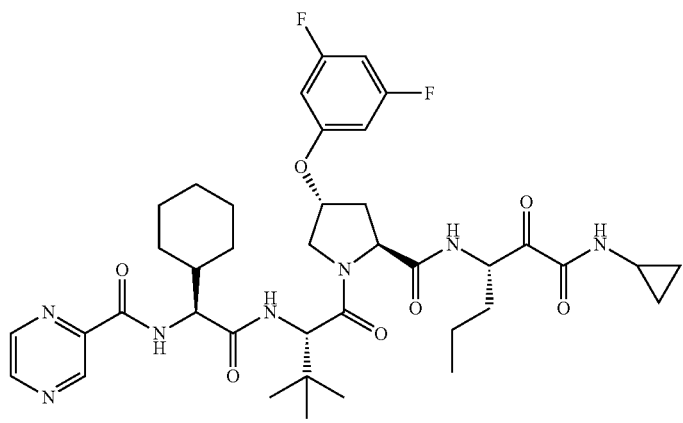 |
| 56 | 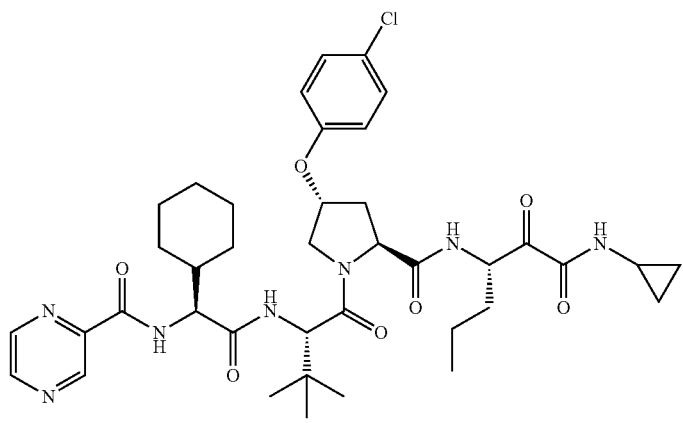 |

| No. | Structure |
|---|---|
| 57 | 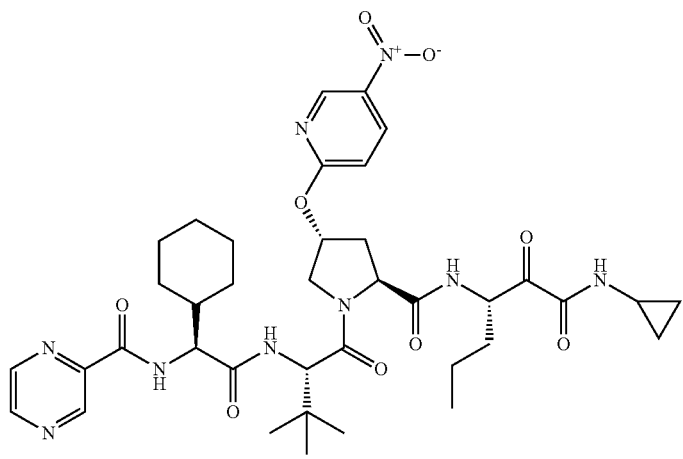 |
| 58 | 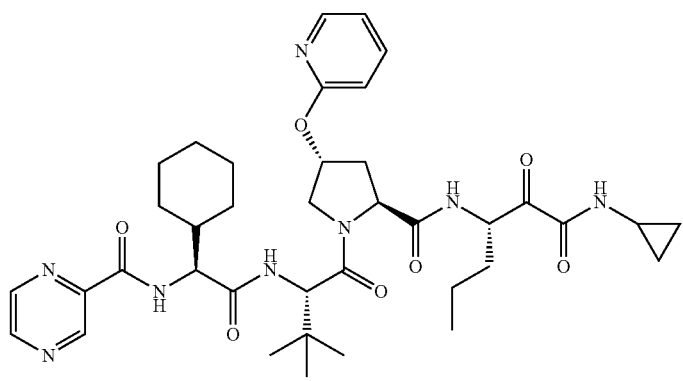 |
| 59 | 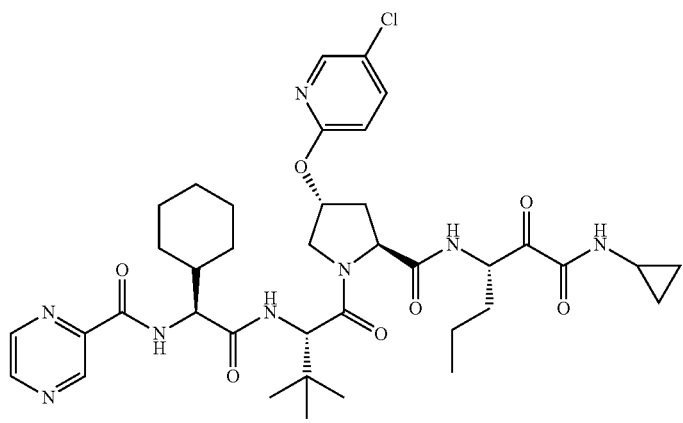 |

| No. | Structure |
|---|---|
| 60 | 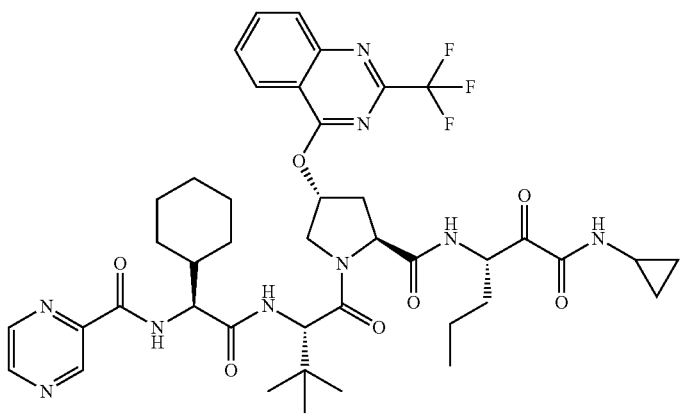 |
| 61 | 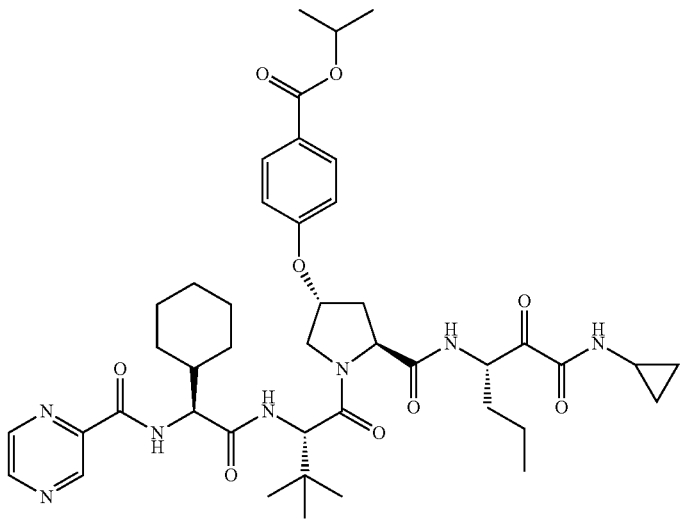 |
| 62 | 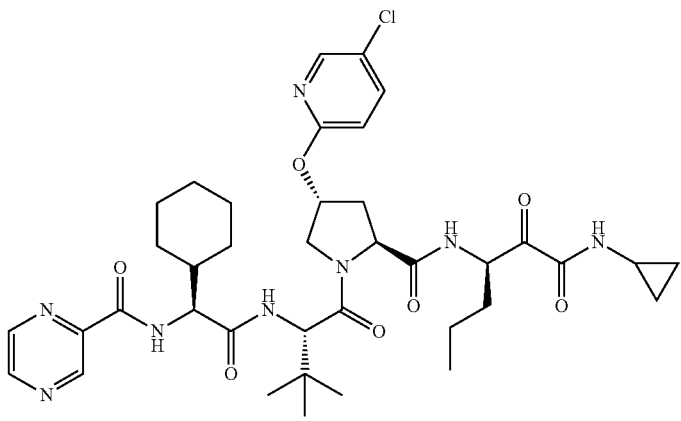 |

| No. | Structure |
|---|---|
| 63 | 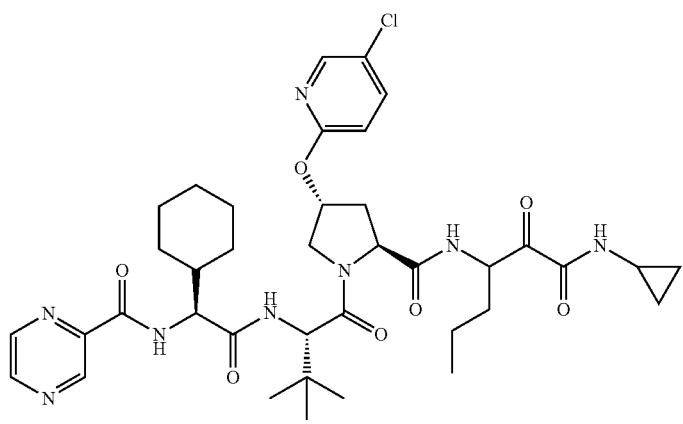 |
| 64 | 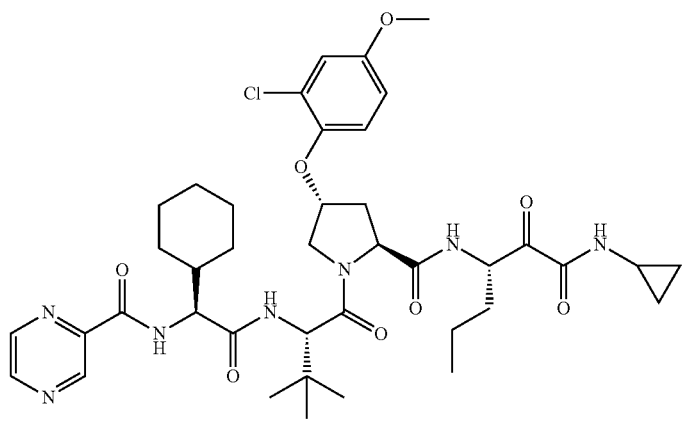 |
| 65 | 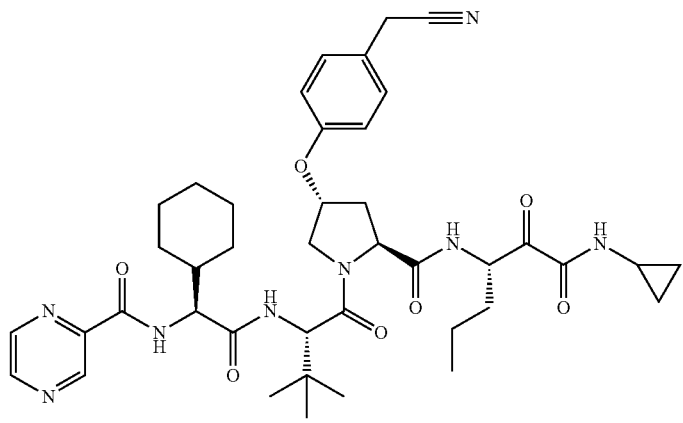 |

-continued
| No. | Structure |
|---|---|
| 66 | 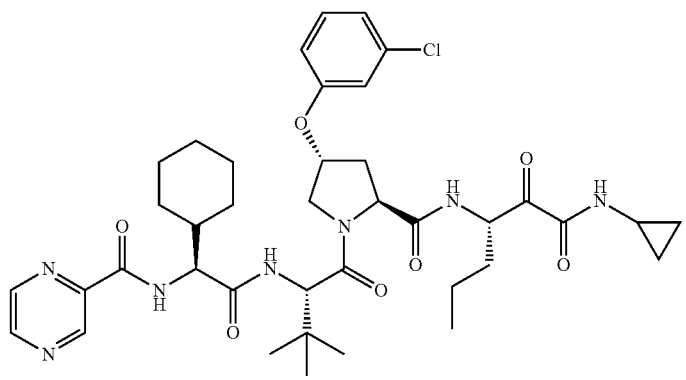 |
| 67 | 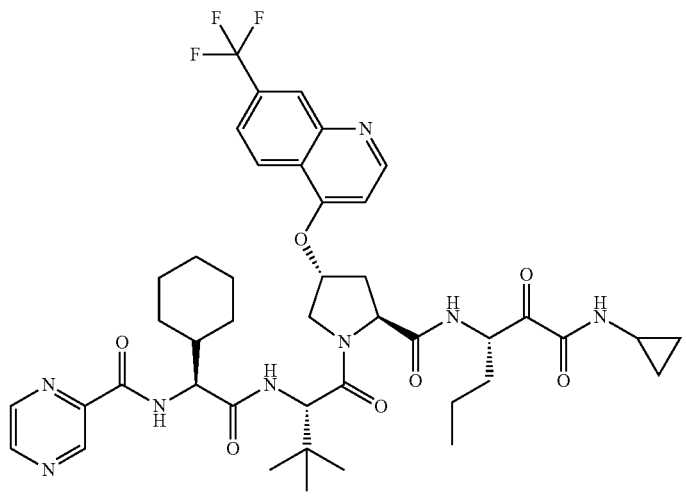 |
| 68 | 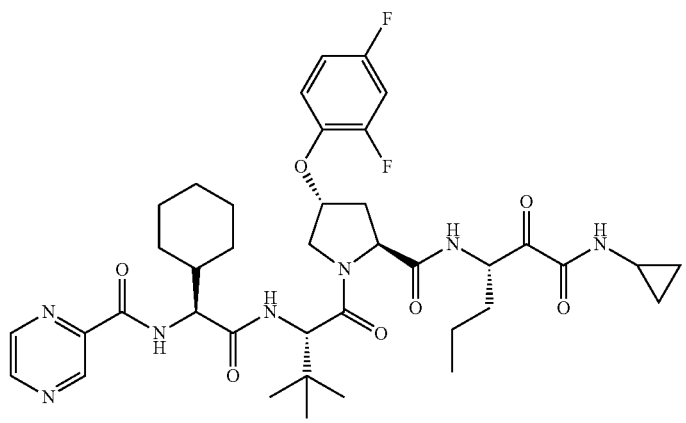 |

| No. | Structure |
|---|---|
| 69 | 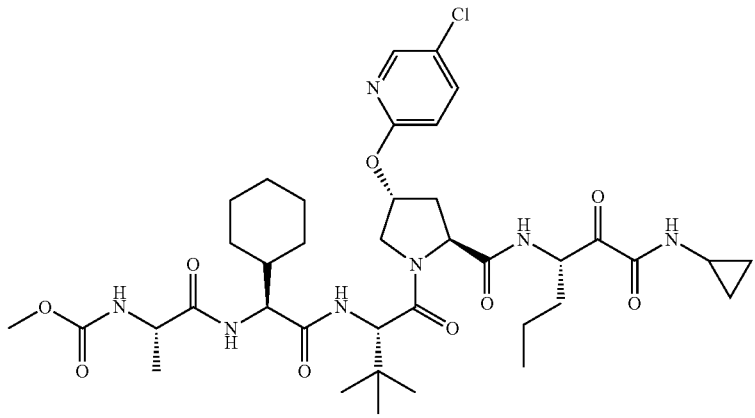 |
| 70 | 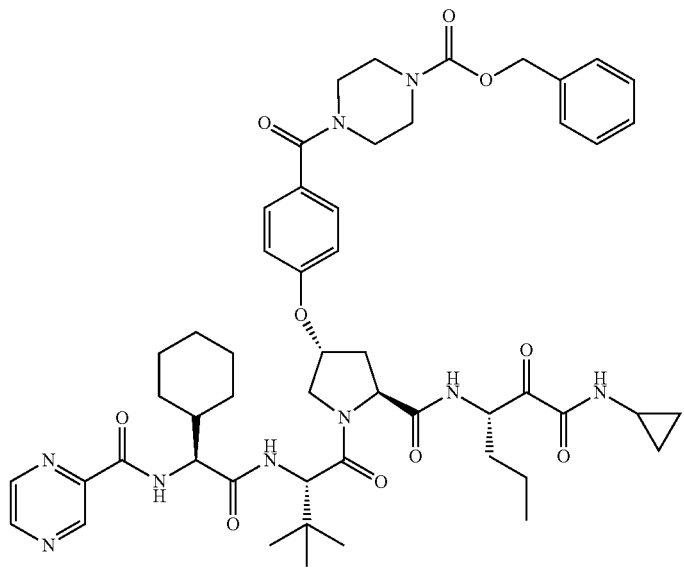 |
| 71 | 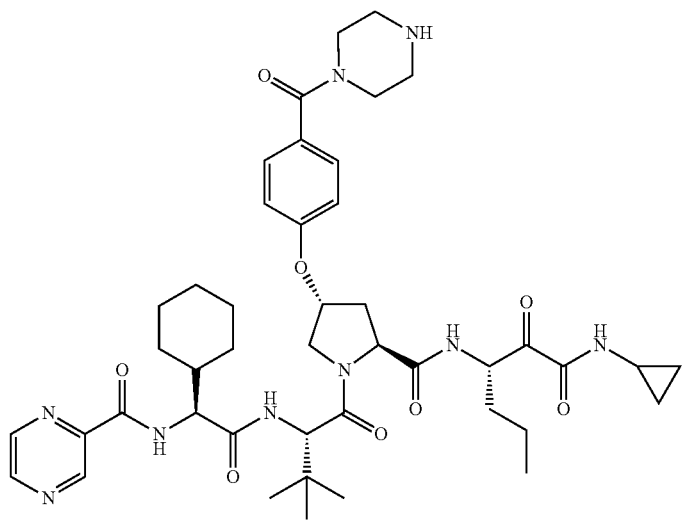 |

-continued
| No. | Structure |
|---|---|
| 72 | 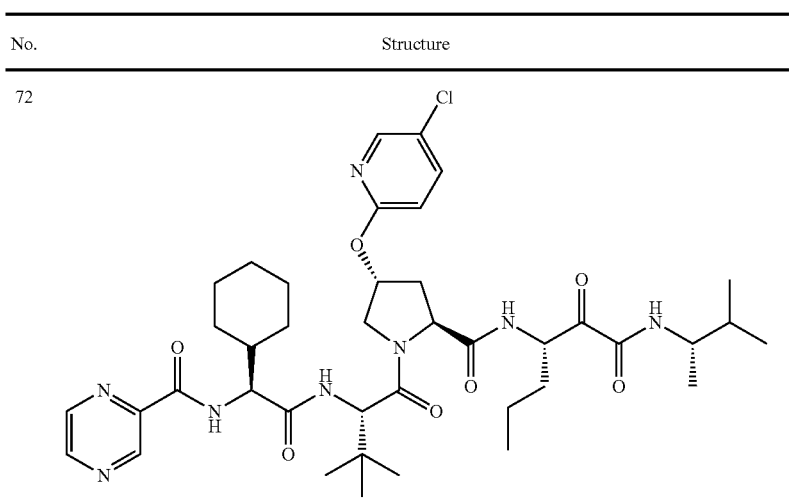 |
| 73 | 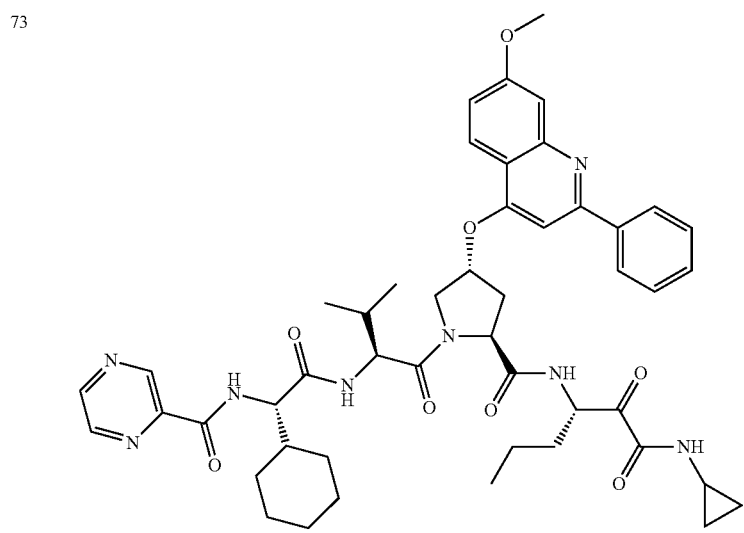 |
| 74 | 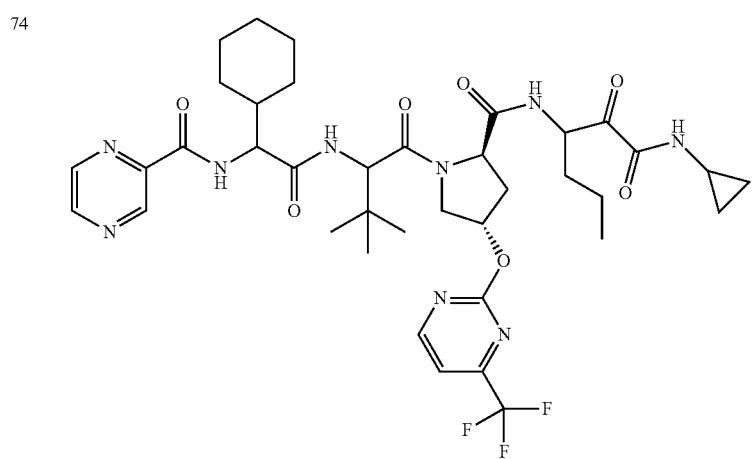 |

| No. | Structure |
|---|---|
| 75 | 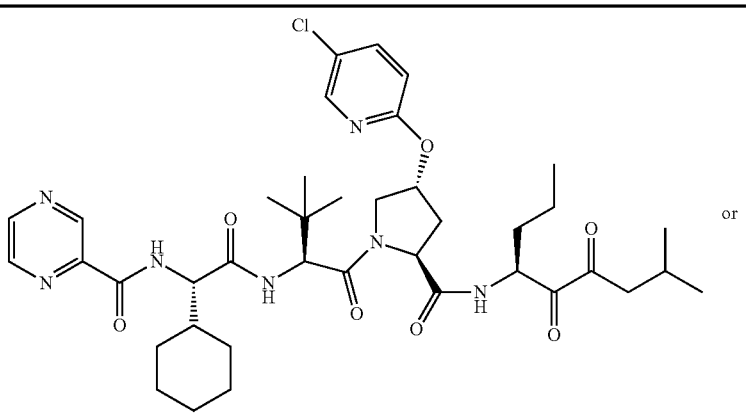 or |
| 76 | 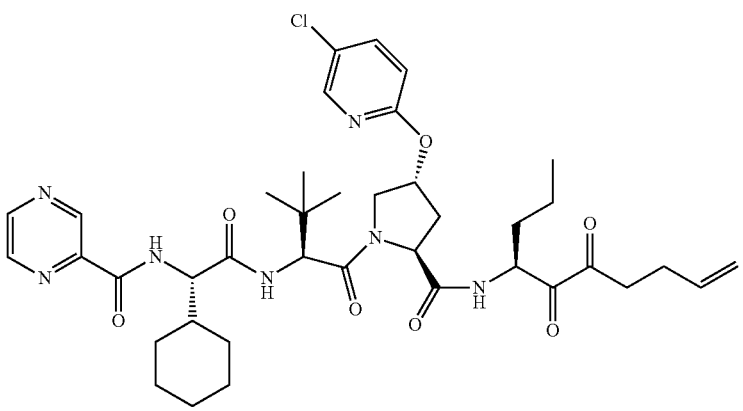 |

26. A composition comprising a compound according to any one of claims 1-25 or a pharmaceutically acceptable salt thereof, in an amount effective to inhibit a serine protease; and a acceptable carrier, adjuvant or vehicle.

27. The composition according to claim 26, wherein said composition is formulated for administration to a patient.

28. The composition according to claim 27, wherein said composition additionally comprises an agent selected from an immunomodulatory agent; an antiviral agent; an inhibitor of HCV protease, helicase, polymerase or metalloprotease; a cytochrome P-450 inhibitor; or combinations thereof.

29. The composition according to claim 28, wherein said immunomodulatory agent is α, β, or γ-interferon or thymosin; the antiviral agent is selected from ribavirin, amantadine, or telbivudine; or the inhibitor is selected from an inhibitor of HCV helicase, polymerase, or metalloprotease.

30. The composition according to claim 28 wherein said cytochrome P-450 inhibitor is ritonavir.

31. A method of inhibiting the activity of a serine protease comprising the step of contacting said serine protease with a compound according to any one of claims 1-25.

32. The method according to claim 31, wherein said protease is an HCV NS3 protease.

33. A method of treating an HCV infection in a patient comprising the step of administering to said patient a composition according to claim 26.

34. The method according to claim 33, comprising the additional step of administering to said patient an agent selected from an immunomodulatory agent; an antiviral agent; an inhibitor of HCV protease, helicase, polymerase, or metalloprotease; a cytochrome P-450 inhibitor; or combinations thereof; wherein said agent is administered to said patient as part of said composition according to claim 29 or as a separate dosage form.

35. The method according to claim 34, wherein said immunomodulatory agent is α, β, or γ-interferon or thymosin; said antiviral agent is ribavarin or, amantadine; or said inhibitor is selected from an inhibitor of HCV helicase, polymerase, or metalloprotease.

36. A method of eliminating or reducing HCV contamination of a biological sample or medical or laboratory equipment, comprising the step of contacting said biological sample or medical or laboratory equipment with a compound according to any one of claims 1-25.

37. The method according to claim 36, wherein said sample or equipment is selected from a body fluid, biological tissue, a surgical instrument, a surgical garment, a laboratory instrument, a laboratory garment, a blood or other body fluid collection apparatus; a blood or other bodily fluid storage material.

38. The method according to claim 37, wherein said body fluid is blood.

* * * * *